US011192915B2

United States Patent
Cummins et al.

(10) Patent No.: US 11,192,915 B2
(45) Date of Patent: Dec. 7, 2021

(54) SYNTHESIS OF POLYPHOSPHORYLATED MOLECULES FROM POLYPHOSPHATES

(71) Applicant: MASSACHUSETTS INSTITUTE OF TECHNOLOGY, Cambridge, MA (US)

(72) Inventors: Christopher C. Cummins, Dorchester, MA (US); Scott Shepard, Somerville, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/503,551

(22) Filed: Jul. 4, 2019

(65) Prior Publication Data

US 2020/0010500 A1     Jan. 9, 2020

Related U.S. Application Data

(60) Provisional application No. 62/693,975, filed on Jul. 4, 2018.

(51) Int. Cl.
| | |
|---|---|
| *C07H 19/20* | (2006.01) |
| *C07H 19/10* | (2006.01) |
| *C07F 9/09* | (2006.01) |
| *C07F 9/6574* | (2006.01) |

(52) U.S. Cl.
CPC ............ *C07H 19/20* (2013.01); *C07F 9/098* (2013.01); *C07F 9/65746* (2013.01); *C07H 19/10* (2013.01)

(58) Field of Classification Search
CPC ..... C07H 19/20; C07H 19/10; C07F 9/65746; C07F 9/098
USPC ...................................................... 536/26.26
See application file for complete search history.

(56) References Cited

U.S. PATENT DOCUMENTS

| | | |
|---|---|---|
| 8,614,312 B2 | 12/2013 | Peyrottes |
| 2009/0142849 A1 | 6/2009 | Yao |
| 2011/0118454 A1 | 5/2011 | Peyrottes |
| 2016/0067275 A1 | 3/2016 | Ayawane |

OTHER PUBLICATIONS

Gao et al. α-Amino acid behaves differently from β- or r-amino acids as treated by trimetaphosphate. Amino Acids (2008) 34: 47-53. (Year: 2008).*
Mohamady et al. Synthesis of Nucleoside Tetraphosphates and Dinucleoside Pentaphosphates via Activation of Cyclic Trimetaphosphate. Org. Lett., vol. 15, No. 11, p. 2612-2615, 2013. (Year: 2013).*
Campagne et al. (1H-Benzotriazol-1-yloxy)tris(dimethylamino)phosphonium Hexafluorophosphate- and (1H-Benzotriazol-1-yloxy)tripyrrolidinophosphonium Hexafluorophosphate-Mediated Activation of Monophosphonate Esters. J. Org. Chem. 1995, 60, 16, 5214-5223. (Year: 1995).*
International Search Report and Written Opinion for PCT/US2019/040662 dated Oct. 24, 2019.
PubChem. CID 193895.Aug. 9, 2005, pp. I-II . Retrieved from the Internet <URL: https:pubchem.ncbi.nlm.hin.gov/compound/193895>; p. 2, formula.
(Jiang, Y at al.) 'Dihydrogen Tetrametaphosphate, [P4012H2]2-: Synthesis, Solubilization In Organic Media, Preparation of its Anhydride [P4011 ]2- and Acdic Methyl Ester, and Conversion to Tetrametaphosphate Metal Complexes via Protonolysis'; Aug. 7, 2014, Journal of the American Chemical Society; vol. 136, Issue 34, pp. 11894-11897; abstract.

* cited by examiner

*Primary Examiner* — Yih-Horng Shiao
(74) *Attorney, Agent, or Firm* — Honigman LLP

(57) ABSTRACT

Metaphosphate compounds can directly phosphorylate other compounds to provide easy synthetic access to phosphorylated compounds, including cyclic phosphate compounds.

6 Claims, 32 Drawing Sheets

SYNTHESIS OF POLYPHOSPHORYLATED MOLECULES FROM POLYPHOSPHATES

PRIORITY CLAIM

The application claim priority from U.S. Provisional Patent Application No. 62/693,975, filed Jul. 4, 2018, which is incorporated by reference in its entirety.

GOVERNMENT SPONSORSHIP

This invention was made with Government support under Grant No. CHE1305124 awarded by the National Science Foundation. The Government has certain rights in the invention.

FIELD OF THE INVENTION

The invention relates to phosphorylation of molecules.

BACKGROUND

Phosphorylation chemistry is key to the synthesis of biomolecules and regulation of cellular processes. See, Cohen, P. *Nature Cell Biology* 2002, 4, E127-E130, which is incorporated by reference in its entirety. Furthermore, many biomolecules contain long polyphosphate chains. Adenosine triphosphate (ATP), one of the most well-known organic polyphosphates, is involved in hundreds of biological processes including neurotransmission, biochemical transport, and synthesis of DNA, proteins, and other biomolecules. See, Burnstock, G. *Trends in Pharmacological Sciences* 2006, 27, 166-176; and Hara, K. Y.; Kondo, A. *Microbial Cell Factories* 2015, 14,198, each of which is incorporated by reference in its entirety. Due to its prevalence, ATP can be isolated on a commercial scale from a variety of biological sources. See, Lautenschlager, C. L.; Lindner, F. No Title. 1943; and Nakajima, S.; Okuyama, G. *Adenosine triphosphate from marine animals*, 1959, each of which is incorporated by reference in its entirety. However, for many polyphosphorylated biomolecules relevant to biochemical and pharmacological research, there is no readily available biological source, requiring intensive synthesis. See, Jessen, H. J.; Ahmed, N.; Hofer, A. *Org. Biomol. Chem.* 2014, 12, 3526-3530, which is incorporated by reference in its entirety. Furthermore, no single phosphorylation method is acceptable for all desirable biological substrates, and the most advanced methods require tedious iterative steps of coupling, oxidation, and deprotection. Burgess, K.; Cook, D. *Chemical Reviews* 2000, 100, 2047-2060, which is incorporated by reference in its entirety. As a result, even relatively common nucleoside triphosphates are extremely expensive from commercial sources. Guanosine triphosphate, for example, is sold by Sigma-Aldrich for approximately $600 per gram compared to $2 per gram for free guanosine. Di- or tetraphosphorylated molecules are often even more expensive, and for specialized phosphorylated molecules there is often no commercial source.

Traditional routes to triphosphorylated molecules involve coupling pyrophosphate to monophosphorylated substrates. See, Baddiley, J.; Michelson, A. M.; Todd, A. R. *Nature* 1948, 161, 761-762 which is incorporated by reference in its entirety. However, this strategy suffers from the need for monophosphorylated starting material and often employs expensive silver salts. More recently, a variety of methods and reagents have been developed to monophosphorylate suitably nucleophilic substrates, often employing dicyclohexylcarbodiimide (DCC) as a coupling reagent. See, Nussbaum, A. L.; Tiberi, R. *Journal of the American Chemical Society* 1965,87, 2513-2514, which is incorporated by reference in its entirety. Furthermore, this strategy has been extended in iterative steps to the synthesis of polyphosphates, but with every additional step the cost of synthesis increases dramatically. Furthermore, no iterative method is general to all substrates due to the possibility of incompatible functional groups. See, Burgess, K.; Cook, D. *Chemical Reviews* 2000, 100, 2047-2060; and Moffatt, J. *Sugar nucleotide synthesis by the phosphoromorpholidate procedure;* 1966; pp 136-142, each of which is incorporated by reference in its entirety.

SUMMARY

In one aspect, a method of polyphosphorylating a compound can include contacting the compound with an activated polyphosphate, wherein the compound includes a nucleophilic group.

In another aspect, a compound can include a triphosphorylated or tetraphosphorylated compound, wherein the triphosphorylated or tetraphosphorlyated compound includes a cyclic phosphate. The triphosphorylated or tetraphosphorylated compound can be synthesized in a single step.

In another aspect, a compound can include a trimetaphosphate 7-azabenzotriazole phosphoester, a trimetaphosphate benzotriazol-1-yl-oxy phosphoester or tetraphosphorylating agent anhydride $[P_4O_{11}]^{2-}$.

In another aspect, a method of polyphosphorylating a compound can include contacting monohydrogen tetrametaphosphate with a protein coupling agent to form an activated polyphosphate and contacting the activated polyphosphate with the compound. The protein coupling agent can be PyAOP, PyBOP, PyBrOP, PyOxim, or HATU.

In certain embodiments, the activated polyphosphate can be a triphosphate or a tetraphosphate, optionally, a cyclic phosphate.

In another aspect, the activated polyphosphate can be a phosphorus ylide.

In certain embodiments, the activated polyphosphate can be an N-oxy-amino polyphosphate ester.

In certain embodiments, the activated polyphosphate can be a trimetaphosphate 7-azabenzotriazole phosphoester or a trimetaphosphate benzotriazol-1-yl-oxy phosphoester or tetraphosphorylating agent anhydride $[P_4O_{11}]^{2-}$.

In certain embodiments, the compound can be HNuc, wherein –Nuc includes an oxo, amino, or thio group.

In certain embodiments, the compound can be a biochemical substrate, for example, a nucleoside, an amino acid, a sugar, and a fatty acid.

In certain embodiments, the compound can be monohydrogen tetrametaphosphate.

In certain embodiments, the compound can be a carbonyl-containing compound.

Other aspects, embodiments, and features will be apparent from the following description, the drawings, and the claims.

DETAILED DESCRIPTION

Figure 1:
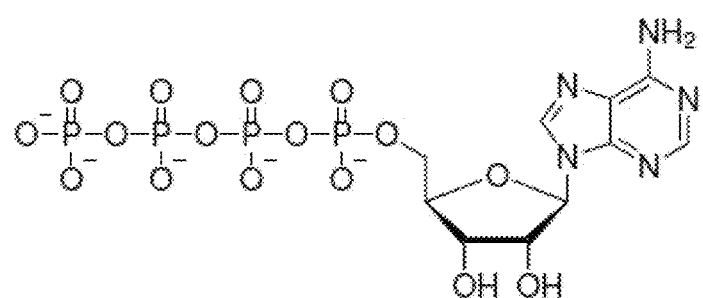
FIG. 1 shows adenosine 5'-tetraphosphate.

In general, a method of polyphosphorylating a compound can include contacting monohydrogen tetrametaphosphate with a protein coupling agent to form an activated polyphosphate and contacting the activated polyphosphate with the compound. Unexpectedly, polyphosphorylation can be accomplished in a single single synthetic step.

Phosphorylation chemistry is key to the synthesis of nucleoside triphosphates and their analogs. See, Monir-Vaghefi, S.-M., *Nucleoside Triphosphates and Their Analogs Chemistry, Biotechnology, and Biological Applications*. Taylor & Francis, 2005, which is incorporated by reference in its entirety. In a direct quote from a recent book on the topic, "No satisfactory protocol exists for preparing all nucleoside triphosphates. The field can benefit from some research innovations for preparation of these important molecules. For example, no procedures will allow for direct one-step triphosphorylation or synthesis of a diverse set of nucleoside triphosphates via a combinatorial or parallel synthesis." Enabling new methodology can make possible facile, direct tri- and tetra-phosphorylation.

Phosphorylation chemistry is also key to the synthesis of phosphorylated amino acids and peptides. See, Hauser, A.; Penkert, M.; Hackenberger, C. P. R., Chemical approaches to investigate labile peptide and protein phosphorylation. *Accounts of Chemical Research* 2017, 50, 1883-1893, which is incorporated by reference in its entirety. There is an underdeveloped level of knowledge concerning phosphorylated nucleophilic amino acids other than Ser, Thr, and Tyr because they have limited chemical and thermal stability. Conventional protocols often contain at least one step of applying acidic conditions under which the phosphate group would be cleaved off. Anhydride formation of Glu and Asp are known, but no recent synthetic or proteomic approaches have been reported. No reports on novel synthetic approaches for pAsp or pGlu have been published recently.

Novel reagents and methodologies can be developed for direct tri- and tetraphosphorylation and envision applications to the phosphorylation of a range of substrates including nucleosides, lipids, and amino acids. The approach differs from existing ones in several respects. While typical approaches to nucleoside triphosphates (NTPs) involve phosphorylation of a nucleoside monophosphate (NMP), the approach is to effect chemoselective direct tri- or tetraphosphorylation of an unprotected nucleoside using reagents have been recently synthesized and characterized. Another distinction of the methodology is the use of lipophilic counter-cations for the polyanionic oligophosphate groups in the reagents and products, enabling them to be utilized in polar, aprotic media, thus maximizing the lifetime of sensitive linkages.

Examples of biological roles for tetraphosphates are beginning to be elucidated, making access to routes for direct tetraphosphorylation increasingly valuable. For example, uridine adenosine tetraphosphate (Up4A) has been shown to be a neurogenic P2Y1 receptor activator in the gut. See, Durnin, L.; Hwang, S. J.; Kurahashi, M.; Drumm, B. T.; Ward, S. M.; Sasse, K. C.; Sanders, K. M.; Mutafova-Yambolieva, V. N., Uridine adenosine tetraphosphate is a novel neurogenic p2y1 receptor activator in the gut. *Proc. Natl. Acad. Sci. U.S.A.* 2014, 111, 15821-15826, which is incorporated by reference in its entirety. Up4A has also been identified as an endothelium derived relaxing factor implicated in vascular dysfunction targeted against hypertension and diabetes. See, Matsumoto, T.; Goulopoulou, S.; Taguchi, K.; Tostes, R. C.; Kobayashi, T., Constrictor prostanoids and uridine adenosine tetraphosphate: vascular mediators and therapeutic targets in hypertension and diabetes. *Br. J. Pharmacol.* 2015, 172, 3980-4001, which is incorporated by reference in its entirety. Diadenosine tetraphosphate (Ap4A) was discovered over 50 years ago, and its intracellular concentration increases upon exposure to stress conditions, but its cellular functions are still enigmatic and an active area of investigation.5 Ap4A is present in the eye and is considered a potential therapeutic nucleotide for the treatment of glaucoma. See, Fonseca, B.; Martí nez-Águila, A.; de Lara, M. J. P.; Pintor, J., Diadenosine tetraphosphate as a potential therapeutic nucleotide to treat glaucoma. *Purinergic Signaling* 2016, 13, 171-177, which is incorporated by reference in its entirety.

A recent review article on chemical and enzymatic synthesis of nucleoside tetraphosphates points out that chemical synthesis enables the carrying out of structure-activity relationship studies by affording access to a diverse array of structures, but that current methods are challenging and often entail multiple stages of protection/deprotection. See, Kore, A. R.; Yang, B.; Srinivasan, B.; Conrad, R., Chemical and enzymatic synthesis of nucleoside tetraphosphates. *Curr. Org. Chem.* 2014, 18, 1621-1650, which is incorporated by reference in its entirety. In contrast, enzymatic synthesis allows for a targeted reaction without the need for protecting group chemistry, but is limited in its substrate specificity and can be prohibitively expensive for large-scale production. In view of such limitations, it is possible to target chemoselective, scalable chemical methods for direct tetraphosphorylation that may be accomplished without the need for protecting group chemistry.

Adenosine 5'-tetraphosphate (A4P, FIG. 1) in 1953 was shown to be a significant fraction of commercial ATP preparations coming from ox muscle. See, Marrian, D. H., A new adenine nucleotide 1953, 12, 492. URL http://www.sciencedirect.com/science/article/pii/0006300253901760, which is incorporated by reference in its entirety. At the time, this new adenosine nucleotide appeared likely to be naturally occurring but its significance was unknown. In a report two years later, adenosine tetraphosphate was isolated from horse muscle, confirming and extending the original report by Marrian. See, Lieberman, I., Identification of adenosine tetraphosphate from horse muscle1. *J. Am. Chem. Soc.* 1955, 77, 3373-3375, which is incorporated by reference in its entirety. Following the observation that adenosine tetraphosphate appeared to be inactive as a phosphate donor in some of the well-known ATP reactions, Lieberman suggested that it has some special biological role while noting that the structural problem remains as to whether the tetraphosphate residue is linear or cyclic.

Figure 2:
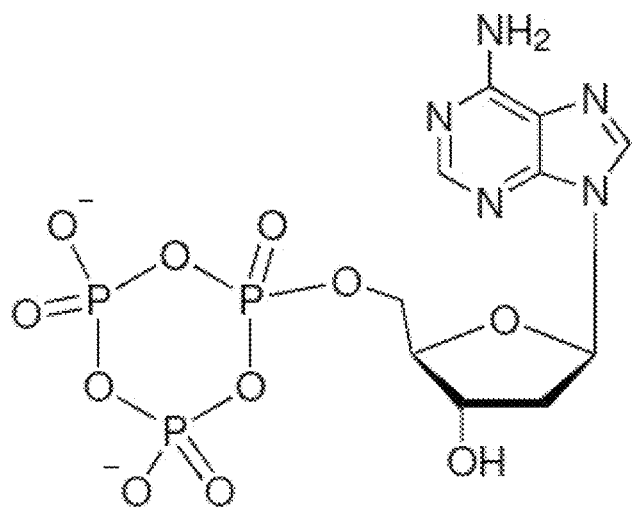
FIG. 2 shows an example of a nucleoside cyclic trimetaphosphate with deoxyadenosine as the nucleoside.

In developing a nucleoside phosphorylation procedure in which all reagents could be soluble and the mixture homogeneous, Khorana utilized trialkylammonium salts in order to enhance solubilities of phosphoric acid esters in anhydrous solvents. Anhydrous pyridine emerged as the preferred medium typically with two equivalents of tri-n-butylamine added to solubilize the orthophosphoric acid component. The conditions arrived at ultimately provided the desired triphosphate as the major product for several different nucleosides. To explain this kinetic selectivity, Khorana advanced the attractive hypothesis that a cyclic metaphosphate ester (see example in FIG. 2) may exist in the reaction medium as a stable species, only to undergo hydrolysis during the aqueous workup to afford the linear triphosphate as the final product. See, Smith, M.; Khorana, H. G., Nucleoside polyphosphates. vi.1 an improved and general method for the synthesis of ribo- and deoxyribonucleoside 5'-triphosphates. *J. Am. Chem. Soc.* 1958, 80, 1141-1145, which is incorporated by reference in its entirety. To date, it appears that such a nucleoside cyclic trimetaphosphate has never been isolated and structurally characterized.

Chemists have been attempting to triphosphorylate nucleosides and other alcohols ever since the early work by Khorana, recognizing that the trisodium salt of trimetaphosphate is readily commercially available and inexpensive. However, most of the successful approaches involved the initial synthesis of a monophosphorylated substrate followed by coupling in some manner with pyrophosphate to provide the desired linear triphosphate. Trimetaphosphate, until recently, has not emerged as an effective reagent for direct triphosphorylation. Mohamady and Taylor recently reported a protocol utilizing the tetrabutylammonium salt of trimetaphosphate together with mesitylenesulfonyl chloride in the presence of DABCO in pyridine as effective for the triphosphorylation of nucleosides bearing OH protecting groups. See, Mohamady, S.; Taylor, S. D., Synthesis of nucleoside triphosphates from 2'-3'-protected nucleosides using trimetaphosphate. *Org. Lett.* 2016, 18, 580-583, which is incorporated by reference in its entirety.

ATP, GTP, and related triphosphorylated nucleosides are essential to regulation of cell function, and the importance of understanding their biosynthesis as well as developing efficient laboratory syntheses has been appreciated for decades. See, Cohen, P., The origins of protein phosphorylation. *Nat. Cell Biol.* 2002, 4, E127-E130 and Boyer, P. D., THE ATP SYNTHASE—a SPLENDID MOLECULAR MACHINE. *Annu. Rev. Biochem.* 1997, 66,717-749, each of which is incorporated by reference in its entirety. Furthermore, phosphate is ubiquitous as a functional group in biology, and the phosphorylation of amino acids, sugars, and proteins have all been studied as possible regulatory mechanisms. See, Hunter, T., Protein kinases and phosphatases: The yin and yang of protein phosphorylation and signaling. *Cell* 1995, 80, 225-236 and Bontemps, F.; Hue, L.; Hers, H.-G., Phosphorylation of glucose in isolated rat hepatocytes. sigmoidal kinetics explained by the activity of glucokinase alone. *Biochem. J.* 1978, 174, 603-611, each of which is incorporated by reference in its entirety. Thus, many synthetic methods have been developed for both mono and poly phosphorylation. See, Burgess, K.; Cook, D., Syntheses of nucleoside triphosphates. *Chem. Rev.* 2000, 100, 2047-2060 and McMurray, J. S.; Coleman, D. R.; Wang, W.; Campbell, M. L., The synthesis of phosphopeptides. *Biopolymers* 2001, 60, 3-31, each of which is incorporated by reference in its entirety. However, even the most advanced polyphosphorylation strategies currently require iterative procedures with multiple steps of oxidation and deprotection as well as harsh reagents. See, Jessen, H. J.; Ahmed, N.; Hofer, A., Phosphate esters and anhydrides—recent strategies targeting nature's favoured modifications. *Org. Biomol. Chem.* 2014, 12, 3526-3530, which is incorporated by reference in its entirety. The novel approaches to polyphosphorylation described herein utilizing metaphosphates solubilized in polar, aprotic organic media by use of lipophilic countercations together with peptide coupling reagents, and complemented by a novel anhydride strategy, promises a significant improvement over existing methods in the ease and efficiency of the overall procedure and work-up.

The potential to effect triphosphorylation in one step from a suitable substrate and trimetaphosphate has been realized for decades. See, Trowbridge, D. B.; Yamamoto, D. M.; Kenyon, G. L. *Journal of the American Chemical Society* 1972, 94, 3816-3824, which is incorporated by reference in its entirety. However, no high yielding procedures for this transformation and biological substrates has been reported until recently, due to inherent limitations of solubility and water sensitivity. Only two reports effecting polyphosphorylation of nucleosides directly from trimetaphosphate have been published. See, Mohamady, S.; Taylor, S. D. *Organic Letters* 2013, 15, 2612-2615; and Mohamady, S.; Taylor, S. D. *Organic Letters* 2016, 18, 580-583, each of which is incorporated by reference in its entirety. These reports demonstrate a significant reduction in the number of steps required to synthesize these molecules, but they are still very limited. The authors only demonstrate reactions with a few specific protected substrates, and their reactions lead to a variety of products. Purification therefore requires an additional step of reverse phase chromatography, a costly addition. Aspects of the invention demonstrate a direct synthesis of triphosphorylated molecules directly from trimetaphosphate with simple isolation and purification. Furthermore, the strategy may be extended to a variety of phosphate substrates to synthesize polyphosphorylated molecules of any desired phosphate chain length with ease.

Phosphorylation chemistry is key to the synthesis of biomolecules and regulation of cellular processes. See, Cohen, P. *Nature Cell Biology* 2002, 4, E127-E130, which is incorporated by reference in its entirety. Accordingly, a variety of synthetic methods have been established to produce phosphorylated species for scientific research without the need for isolation from biological sources. See, Burgess, K.; Cook, D. *Chemical Reviews* 2000, 100, 2047-2060; and McMurray, J. S.; Coleman, D. R.; Wang, W.; Campbell, M. L. *Biopolymers* 2001, 60, 3-31, each of which is incorporated by reference in its entirety. Phosphorylated biomolecules often contain linear phosphate chains, such as in ubiquitous adenosine triphosphate (ATP), yet the vast majority of synthetic phosphorylation strategies effect the addition of only one phosphate unit. Therefore, the synthesis of polyphosphorylated species requires iterative steps of coupling, oxidation, and deprotection, greatly increasing the cost of such molecules. See, Jessen, H. J.; Ahmed, N.; Hofer, A. *Org. Biomol. Chem.* 2014, 12, 3526-3530, which is incorporated by reference in its entirety. A simple, efficient, and scalable synthesis of triphosphorylated species directly from trimetaphosphate using a common peptide coupling reagent, 7-azabenzotriazol -1-yloxy)tripyrrolidinophosphonium hexafluorophosphate (PyAOP) is reported. See, Carpino, L. A.; El-Faham, A.; Minor, C. A.; Albericio, F. *Journal of the Chemical Society, Chemical Communications* 1994, 201, which is incorporated by reference in its entirety.

Trimetaphosphate, 1, hydrolyzes to linear triphosphate. Therefore, it was hypothesized that alcoholysis of this molecule would lead to triphosphorylated molecules in one step as early as the 1960s. See, Feldmann, W. *Chemische Berichte* 1966, 99, 3251-3259; and Trowbridge, D. B.; Yamamoto, D. M.; Kenyon, G. L. *Journal of the American Chemical Society* 1972, 94, 3816-3824, each of which is incorporated by reference in its entirety. However, attempts to achieve this transformation suffered from rampant hydrolysis and low yields. Therefore this strategy was seemingly abandoned until a recent report by Taylor. See, Mohamady, S.; Taylor, S. D. *Organic Letters* 2016, 18, 580-583 and Mohamady, S.; Taylor, S. D. *Organic Letters* 2013, 15, 2612-2615, each of which is incorporated by reference in its entirety. The authors present a synthesis of several 2',3' diprotected nucleosides directly from the tetra-n-butylammonium salt of trimetaphosphate in what is the first practical synthesis of triphosphorylated molecules directly from trimetaphosphate. Therefore, this report is a significant improvement over the previously established iterative methods of polyphosphorylation. See, Jessen, H. J.; Ahmed, N.; Hofer, A. *Org. Biomol. Chem.* 2014, 12, 3526-3530, which is incorporated by reference in its entirety. However, this method can be significantly improved. The reported procedure is only demonstrated for alcoholic substrates, requires protected nucleosides, is of low activity, and requires ion exchange chromatography in the work-up. Furthermore, the mechanism of this phosphorylation strategy is not well understood.

Our group, and others, have recently advanced the chemistry of metaphosphates, particularly as ligands for transition metal complexes, by solubilization in polar aprotic organic media utilizing the lipophilic bis(triphenylphosphine)iminium (PPN) cation. See, Jiang, Y.; Chakarawet, K.; Kohout, A. L.; Nava, M.; Marino, N.; Cummins, C. C. *Journal of the American Chemical Society,* 2014, 136, 11894-11897; Klemperer, W. G.; Main, D. J. *Inorganic Chemistry* 1990, 29, 2355-2360; Chakarawet, K.; Knopf, I.; Nava, M.; Jiang, Y.; Stauber, J. M.; Cummins, C. C. *Inorganic Chemistry* 2016, 55, 6178-6185; Stauber, J. M.; Cummins, C. C. *Inorganic Chemistry* 2017, 56, 3022-3029; and Stauber, J. M.; Zhang, S.; Gvozdik, N.; Jiang, Y.; Avena, L.; Stevenson, K. J.; Cummins, C. C. *Journal of the American Chemical Society* 2018, 140, 538-541, each of which is incorporated by reference in its entirety. Furthermore, the resulting species are highly crystalline and amenable to purification by crystallization. Additionally, PPN cations are facilely exchanged for alkali metals by treating them with triflate salts, thereby eliminating the need for any column chromatography. To further advance the investigation of metaphosphates, attempts were made to functionalize these molecules with organic fragments. However, a review of existing phosphorylation chemistry did not provide a satisfactory route to the desired compounds.

One of the first attempts to activate trimetaphosphate towards nucleophilic attack was by conversion to an acyl or triflyl phosphate by reaction with acetic anhydride or triflic anhydride, but appreciable reactivity with either of these reagents was not observed. See, Avison, A. W. D. *Journal of the Chemical Society (Resumed)*, 1955, 732, which is incorporated by reference in its entirety. Secondly, phosphate chloride generation by reaction with thionyl chloride was attempted, but this generated only insoluble species. See, Wyatt, P.; Eley, H.; Charmant, J.; Daniel, B. J.; Kantacha, A., European Journal of Organic Chemistry 2003, 2003, 4216-4226, which is incorporated by reference in its entirety. Lastly, synthesis of a phosphoramidate was attempted, as these species are commonly employed in monophosphorylation and facilely synthesized from dicyclohexylcarbodiimide (DCC) and a suitable amine. See, Moffatt, J. *Sugar nucleotide synthesis by the phosphoro morpholidate procedure;* 1966; pp 136-142, which is incorporated by reference in its entirety. This reaction however, produced only an N-phosphoryl urea, which is not an active phosphorylating agent, in analogy to N-acyl ureas when DCC is used for peptide coupling. See, Glonek, T.; Kleps, R. A.; Van Wazer, J. R.; Myers, T. C., *Bioinorganic Chemistry* 1976, 5, 283-310 and Carpino, L. A. *Journal of the American Chemical Society* 1993, 115, 4397-4398, which is incorporated by reference in its entirety.

Figure 23:
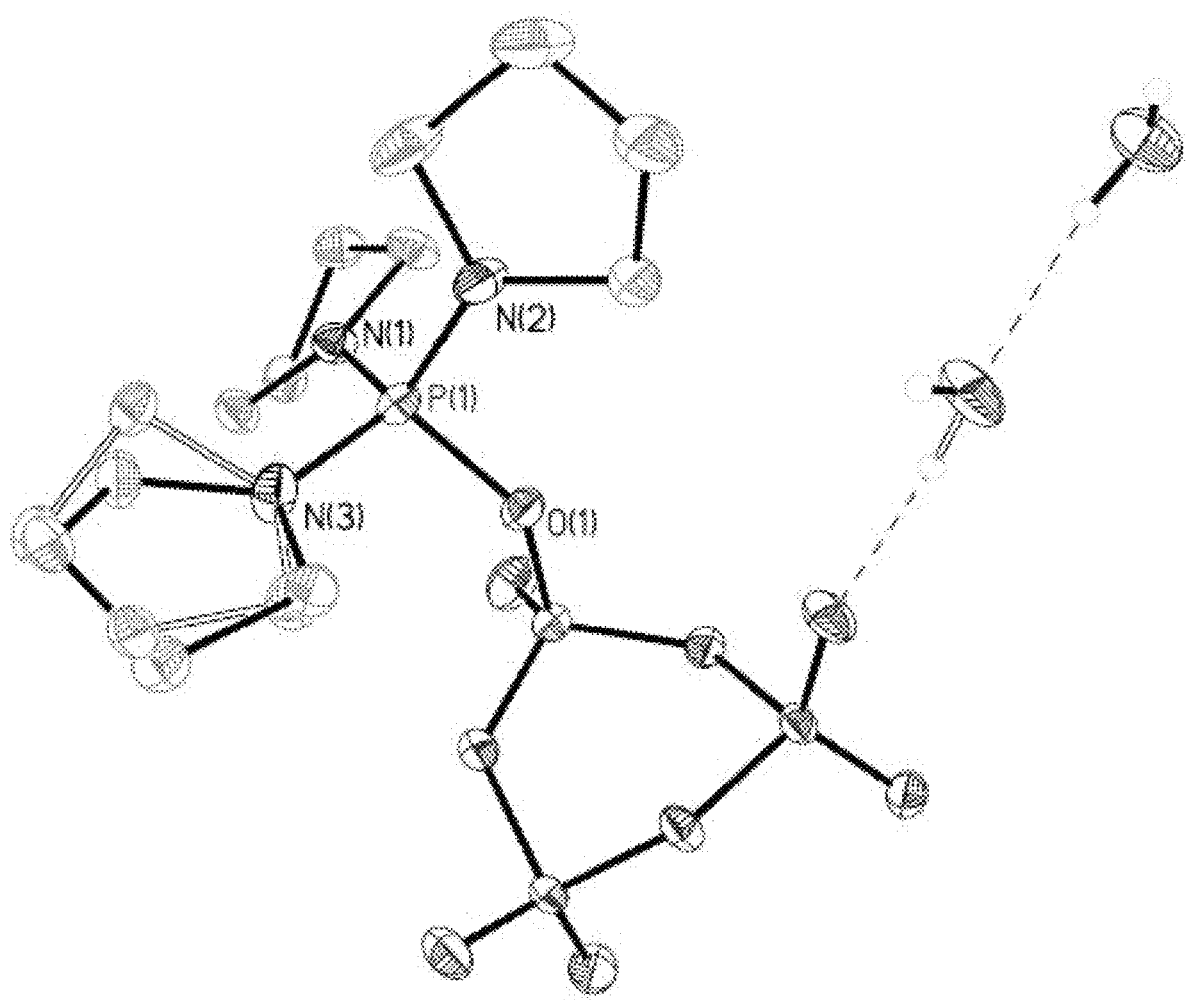
FIG. 23 shows a single Crystal X-ray Structure of 2 with Thermal Ellipsoids set at 50% and the PPN Counterion and Most Hydrogens Omitted for Clarity.

Noting the similarity between phosphates and carboxylates, it was therefore hoped that more advanced peptide coupling reagents, which do not suffer from this rearrangement, might be utilized to create phosphoesters activated for nucleophilic attack. See, Al-Warhi, T. I.; Al-Hazimi, H. M.; El-Faham, A. *Journal of Saudi Chemical Society* 2012, 16, 97-116, which is incorporated by reference in its entirety. Indeed, treating $P_3O_9$ with PyAOP generated a new species, 2. A single crystal X-ray diffraction study and heteronuclear NMR determined the structure to be a trimetaphosphate ring bound to a phosphonium moiety (FIG. 23). Furthermore, initial studies demonstrated this species to be an active trimetaphosphorylation reagent.

Figure 21:
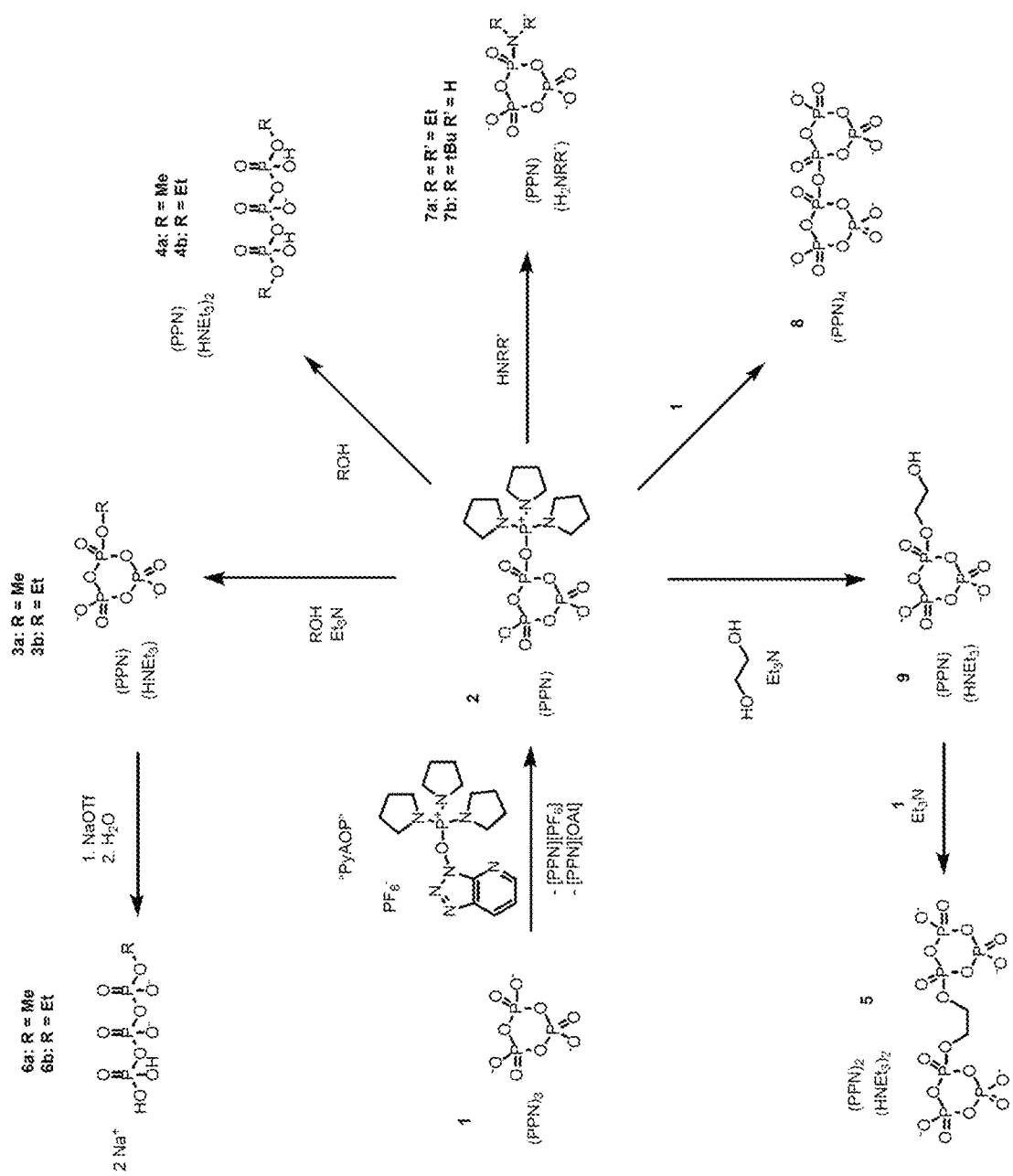
FIG. 21 shows an overall scheme.

In one aspect, this invention describes a method of producing polyphosphorylated molecules directly from polyphosphates and nucleophilic substrates utilizing phosphonium based peptide coupling reagents such as (7-azabenzotriazol-1-yloxy)tripyrrolidinophosphoniumhexafluorophosphate (PyAOP). Central to this invention is the new compound $[PPN][P_3O_9P(NC_4H_8)_3]\cdot 2H_2O$, 2, formed by treating trimetaphosphate, 1, with PyAOP. This compound reacts with nucleophiles such as alcohols, amines, and phosphates to generate new polyphosphorylated molecules (FIG. 21).

Importantly, not only can one deliver improved methods for tri and tetraphosphorylation, but also one can provide thorough characterization of the structure and properties of the active phosphorylating agent(s). This is prioritized so as to provide not only practical methodologies for attaching polyphosphate residues to targets of interest, but also to facilitate structure-activity/selectivity relationships needed to understand the functional group selectivities of the systems under investigation. One can also aim to deliver detailed information on phosphorylated products such as the one proposed by Khorana (FIG. 2), containing still intact tri and tetraphosphate rings to permit, for the first time, a thorough evaluation of such intriguing substances.

It is possible to eliminate the requirement for an already monophosphorylated starting material in the synthesis of tri and tetra-phosphorylated substrates. A broad substrate scope can be targeted in developing reagents to tri- and tetra-phosphorylate various protic nucleophiles. A major aspect of the innovation is putting together reagents from modern peptide-coupling chemistry together with the polyanionic trimetaphosphate and tetrametaphosphate rings that are solubilized in polar, aprotic media using lipophilic organic cations. In the particular case of the tetrametaphosphate system, a reagent has been developed that is the anhydride of dihydrogen tetrametaphosphate and have demonstrated that it is active for tetraphosphorylation of simple substrates.

Initial studies suggest that the new methodology, is superior to previous phosphorylation procedures due to its simplicity. Summarized as a one-pot procedure in FIG. 3, the protocol consists of (i) activation of trimetaphosphate using a peptide coupling reagent such as PyAOP, followed by (ii) addition of a protic nucleophile (HNuc) such as an alcohol, an amine, a thiol, or a carboxylic acid; preliminary results suggest that all such functional groups are amenable to the reaction and that the crystalline salts having the general formula $[PPN]_2[P_3O_8Nuc]$ (PPN=bis(triphenylphosphine) iminium) may be obtained in pure form sans chromatography. After purification, the PPN cations can be trivially exchanged for biologically relevant cations by addition of alkali metal or ammonium triflate salts to an acetonitrile solution of the product, resulting in immediate precipitation of the desired product. Furthermore, the methodology has strong potential applicability beyond the synthesis of nucleoside triphosphates.

Figure 3:
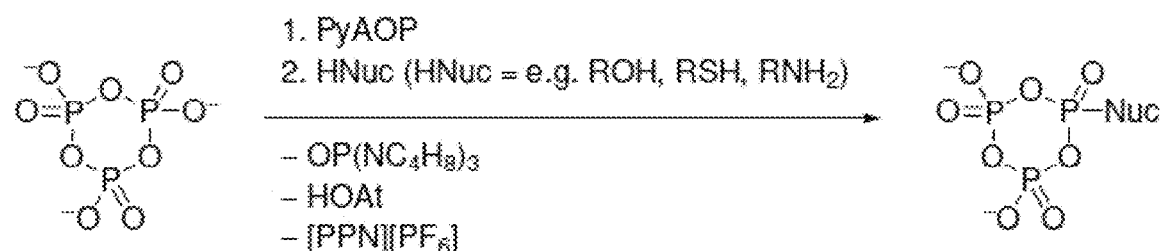
FIG. 3 shows an example of a generalized one-pot procedure for triphosphorylation using trimetaphosphate and a peptide coupling reagent.

Based upon examples from preliminary results (see below in Approach) and a seminal publication in which the synthesis and characterization of the anhydride tetraphosphorylating agent $[P_4O_{11}]^{2-}$ is described (see, Jiang, Y.; Chakarawet, K.; Kohout, A. L.; Nava, M.; Marino, N.; Cummins, C. C., Dihydrogen tetrametaphosphate, $[P_4O_{12}H_2]^{2-}$: Synthesis, solubilization in organic media, preparation of its anhydride $[P4O_{11}]^{2-}$ and acidic methyl ester, and conversion to tetrametaphosphate metal complexes via protonolysis. *J. Am. Chem. Soc.* 2014, 136, 11894-11897, which is incorporated by reference in its entirety) the first of two envisioned general strategies for direct tetraphosphorylation of protic nucleophiles HNuc using the anhydride $[P_4O_{11}]^{2-}$ in polar aprotic organic media (FIG. 4) is advanced; this strategy is dubbed "tet1" to distinguish it from the one to be described below, "tet2" that utilizes peptide coupling reagents. Generalized route "tet2" likewise aims for a one-pot procedure to initially generate the functionalized tetrametaphosphate $[P_4O_{12}At]^{3-}$ by reaction of tetrametaphosphate with the phosphonium-based peptide coupling reagent PyAOP, followed by addition of HNuc to afford the tetraphosphorylated product $[P_4O_{11}Nuc]^{3-}$ (FIG. 5). This is directly analogous to the one-pot procedure indicated above for triphosphorylation (FIG. 3).

Although this last topic has placed the emphasis on the specific peptide coupling agents HOAt and PyAOP, many other options are currently available (see for example FIG. 15) and will be investigated as needed in the event these specific ones present unanticipated obstacles.

Triphosphorylation

Methodologies for functionalizing trimetaphosphate are almost nonexistent. See, Mohamady, S.; Taylor, S. D., Synthesis of nucleoside triphosphates from 2'-3'-protected nucleosides using trimetaphosphate. *Org. Lett.* 2016, 18, 580-583, which is incorporated by reference in its entirety. Thus, this interesting moiety has been underutilized both in synthetic chemistry and biochemical applications. However, incorporation of trimetaphosphate into biomolecules is a desirable synthetic target due to its facile hydrolysis to linear triphosphate, a ubiquitous functional group in biology. See, Shen, C. Y., Alkaline hydrolysis of sodium trimetaphosphate in concentrated solutions and its role in built detergents. *Industrial & Engineering Chemistry Product Research and Development* 1966, 5, 272-276, which is incorporated by reference in its entirety. Attempts to directly generate linear triphosphate esters directly from trimetaphosphate were reported as early as the 1960s. See, Feldmann, W., Zur chemie der kondensierten phosphate and arsenate, 1. die phenolyse des trimetaphosphats. Über das monophenyltriphosphat. *Chem. Ber.* 1966, 99, 3251-3259 and Trowbridge, D. B.; Yamamoto, D. M.; Kenyon, G. L., Ring openings of trimetaphosphoric acid and its bismethylene analog. syntheses of adenosine 5'-bis(dihydroxyphosphinylmethyl) phosphinate and 5'-amino-5'-deoxyadensoine 5'-triphosphate. *J. Am. Chem. Soc.* 1972, 94, 3816-3824, each of which is incorporated by reference in its entirety. However, trimetaphosphate does not cleanly react with alcohols, and the pursuit of this methodology was seemingly abandoned. The lack of subsequent literature employing this strategy is surprising, as the reverse reaction, carbodiimide mediated cyclization of the linear triphosphate of ATP to trimetaphosphate is known and has been used to synthesize linear nucleotide tetra and pentaphosphates. See, Hampton, A.; Kappler, F.; Picker, D., Species- or isozyme-specific enzyme inhibitors. 4. design of a two-site inhibitor of adenylate kinase with isozyme selectivity. *J. Med. Chem.* 1982, 25, 638-644, which is incorporated by reference in its entirety. However, the recent solubilization of metaphosphates in aprotic organic media using lipophilic organic cations coupled with the development of powerful peptide coupling reagents opens new avenues for employing trimetaphosphate in phosphorylation. See, Jiang, Y.; Chakarawet, K.; Kohout, A. L.; Nava, M.; Marino, N.; Cummins, C. C., *J. Am. Chem. Soc.* 2014, 136, 11894-11897, Klemperer, W. G.; Main, D. J., *Inorg. Chem.* 1990, 29, 2355-2360, and Carpino, L. A., *J. Am. Chem. Soc.* 1993, 115, 4397-4398, each of which is incorporated by reference in its entirety.

Figure 6:
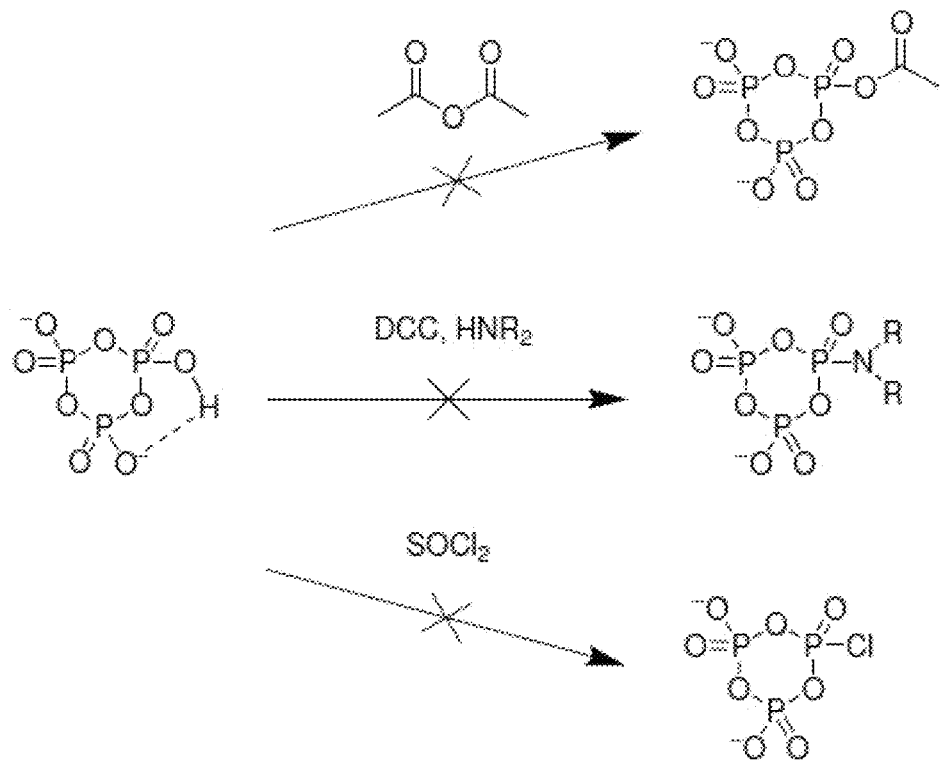
FIG. 6 shows an unsuccessful approaches to trimetaphosphate activation.

In the preliminary investigation of $[PPN]_3[P_3O_9]$ reactivity, a method to functionalize trimetaphosphate with organic residues was sought, but a survey of existing monophosphorylation strategies proved unsatisfactory. Phosphates have previously been activated towards nucleophilic attack via functionalization with a good leaving group. Acetyl phosphates have been employed for this purpose and are routinely synthesized by reaction of phosphates with acetic anhydride. See, Avison, A. W. D., The synthesis of acyl phosphates in aqueous solution. *Journal of the Chemical Society (Resumed)* 1955, page 732, which is incorporated by reference in its entirety. However, neither $[PPN]_3[P_3O_9]$ nor $[PPN]_2[P_3O_9H]$ was found to react appreciably with acetic anhydride, even in the presence of esterification catalysts such as DMAP or at elevated temperatures (FIG. 6). Furthermore, no reaction occurred when treating trimetaphosphate with the much more active triflic anhydride, therefore demonstrating that trimetaphosphate is an extremely poor nucleophile and difficult to functionalize.

Figure 7:
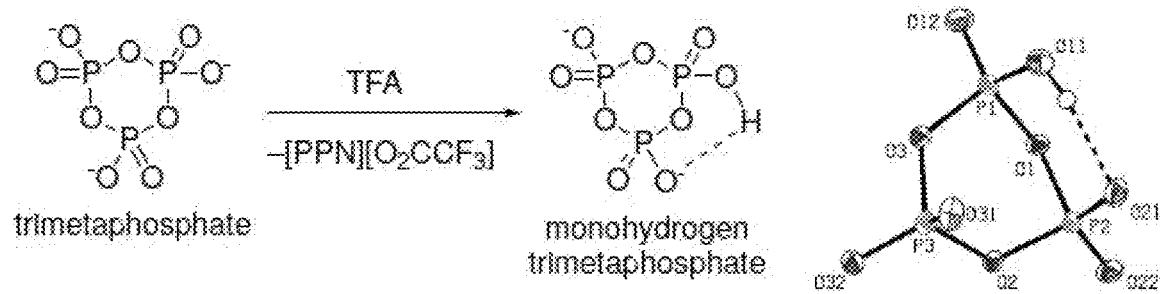
FIG. 7 shows a monohydrogen trimetaphosphate synthesis and thermal ellipsoid plot with PPN cations omitted for clarity.

The synthesis of a phosphoramidate was attempted, as such species have commonly long been employed as monophosphorylation reagents. Typically, phosphoramidates are facilely generated by reaction of a phosphoric acid with a carbodiimide and a suitable amine substrate, often under reflux conditions. However, treating the PPN salt of trimetaphosphate monoacid, $[PPN]_2[P_3O_9H]$ (FIG. 7) with DCC (FIG. 6) and various nucleophiles gave rapidly only a mixture of N-phosphoryl urea and an interesting product resulting from the dehydrative coupling of two trimetaphosphate rings, $[PPN]_4[P_6O_{17}]$. The phosphoramidate synthetic strategy is therefore unsuitable for functionalizing trimetaphosphate, due to the rapid rearrangement of O-phosphorylisourea, the proposed active species when this approach is utilized for monophosphorylation, to N-phosphorylurea, which is not an active phosphorylation reagent. See, Chakarawet, K.; Knopf, I.; Nava, M.; Jiang, Y.; Stauber, J. M.; Cummins, C. C., Crystalline metaphosphate acid salts: Synthesis in organic media, structures, hydrogen-bonding capability, and implication of superacidity. *Inorg. Chem.* 2016, 55, 6178-6185 and Glonek, T.; Kleps, R. A.; Van Wazer, J. R.; Myers, T. C., Carbodiimide-intermediated esterification of the inorganic phosphates and the effect of tertiary amine base. *Bioinorg. Chem.* 1976, 5, 283-310, each of which is incorporated by reference in its entirety. Even at high amine concentrations and low temperature, no targeted phosphoramidate was produced under the various conditions that were examined.

In another preliminary study trimetaphosphoryl chloride was targeted, as phosphate chlorides are known to react under mild conditions with alcohols in the presence of an amine base to generate the corresponding phosphoester. See, Hwang, Y.; Cole, P. A., Efficient synthesis of phosphorylated prodrugs with bis(POM)-phosphoryl chloride. *Org. Lett.* 2004, 6, 1555-1556, which is incorporated by reference in its entirety. A variety of reagents such as oxalyl chloride and thionyl chloride have been utilized to convert phosphoric acids into phosphate chlorides. See, Stowell, M. H.; Ueland, J. M.; McClard, R. W., The mild preparation of synthetically useful phosphonic dichlorides: Application to the synthesis of cyclic phosphonic diesters and diamides. *Tetrahedron Lett.* 1990, 31, 3261-3262 and Wyatt, P.; Eley, H.; Charmant, J.; Daniel, B. J.; Kantacha, A., Synthesis of racemic and enantiomerically pure (r,r,r)-tris(methylbenzyl)phosphane-x-ray crystal structures of the phosphane oxides and borane complexes. *Eur. J. Org. Chem.* 2003, 2003, 4216-4226, each of which is incorporated by reference in its entirety. However, treatment of the monoacid $[PPN]_2[P_3O_9H]$ with thionyl chloride produced only an insoluble precipitate (FIG. 6). The observed precipitation behavior can be ascribed to the formation of HCl which subsequently protonates any phosphate products, causing them to precipitate and remain insoluble in the aprotic organic media. Furthermore, this issue could not be remedied by the addition of amine bases to the reaction mixture, as the ammonium ions that form then exchange for the more soluble PPN cations and again cause all the phosphate species to precipitate from solution.

Figure 8:
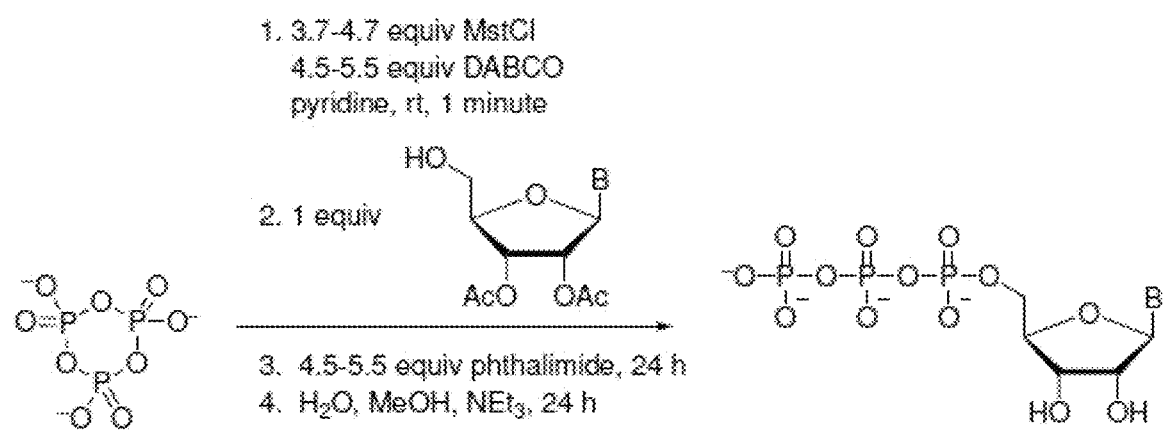
FIG. 8 shows a state of the art for direct triphosphorylation.

The only practical literature procedure for triphosphorylation with trimetaphosphate involves reaction of the TBA salt of trimetaphosphate with mesitylenesulfonyl chloride, followed by conversion to a phosphoramidate, and subsequent nucleophilic substitution by an alcohol (FIG. 8). See, Mohamady, S.; Taylor, S. D., Synthesis of nucleoside triphosphates from 2'-3'-protected nucleosides using trimetaphosphate. *Org. Lett.* 2016, 18, 580-583 and Mohamady, S.; Taylor, S. D., Synthesis of nucleoside tetraphosphates and dinucleoside pentaphosphates via activation of cyclic trimetaphosphate. *Org. Lett.* 2013, 15, 2612-2615, each of which is incorporated by reference in its entirety. The authors state that the DABCO used in the protocol of FIG. 8 may be acting as a general base, and/or may be reacting with the trimetaphosphate/MstCl adduct to give a reactive intermediate. Similarly, they are not clear on the role of the phthalimide, stating that it too may be forming an intermediate reactive enough to phosphorylate the OH groups. This relatively recent methodology has been used for the synthesis of both linear tri and tetraphosphate nucleotides, and it is a significant improvement over the most common methods employed to synthesize these classes of molecules, such as multistep reactions requiring protected nucleosides and harsh reagents such as phosphoryl chloride, $OPCl_3$. See, Ludwig, J.; Eckstein, F., Rapid and efficient synthesis of nucleoside 5'-0-(1-thiotriphosphates), 5'-triphosphates and 2',3'-cyclophosphorothioates using 2-chloro-4h-1,3,2-benzodioxaphosphorin-4-one. *J. Org. Chem.* 1989, 54, 631-635 and Mishra, N. C.; Broom, A. D., A novel synthesis of nucleoside 5'-triphosphates. *J. Chem. Soc., Chem. Commun.* 1991, pages 1276-1277, each of which is incorporated by reference in its entirety. However, this phosphorylation protocol is only applicable to 2',3' protected nucleosides. Thus, it requires a tedious multistep workup involving deprotection, purification by reverse-phase chromatography, and ion exchange chromatography to replace the TBA counterions with biologically relevant ammonium ions. Furthermore, the scope of the procedure is so far only demonstrated for alcoholic substrates. The trimetaphosphate phosphorylation protocol addresses and improves upon these concerns to provide a simple and efficient procedure to generate a wide variety of triphosphorylated molecules. It should be stressed that the procedure of FIG. 8 yields not only the depicted triphosphate product but also corresponding tetraphosphate and monophosphate products as components of the reaction mixture requiring separation by reverse-phase chromatography. Another point of contrast with the method is that the products are isolated with the cyclic phosphate still intact directly as crystalline salts with the lipophilic PPN counter cations. These are easily exchanged for cations, such as alkali metal or ammonium cations, as desired. The mild synthesis conditions will permit the properties of triphosphorylated compounds containing a still-intact trimetaphosphate ring to be studied for the first time, prior to hydrolysis to a linear form. The background in working with various metaphosphate ring sizes, solubilized in anhydrous polar aprotic media through the use of lipophilic counter ions, and in isolating them in pure form as crystalline salts, is what has helped prepare for the developments described herein. See, Jiang, Y.; Chakarawet, K.; Kohout, A. L.; Nava, M.; Marino, N.; Cummins, C. C., *J. Am. Chem. Soc.* 2014, 136, 11894-11897 and Chakarawet, K.; Knopf, I.; Nava, M.; Jiang, Y.; Stauber, J. M.; Cummins, C. C., *Inorg. Chem.* 2016, 55, 6178-6185, each of which is incorporated by reference in its entirety.

To develop an efficient methodology for triphosphorylation using trimetaphosphate, the need to mildly activate the phosphate towards nucleophilic attack and also the inherent similarities between the requirements for this reaction and those that have been developed in the field of peptide coupling were both recognized. The generation of an inactive N-phosphorylurea from the reaction of $[PPN]_2$ $[P_3O_9H]$ with DCC, described above, is directly analogous to the undesirable formation of an inactive N-acylurea when using DCC as a peptide coupling reagent. See, Glonek, T.; Kleps, R. A.; Van Wazer, J. R.; Myers, T. C., Carbodiimide-intermediated esterification of the inorganic phosphates and the effect of tertiary amine base. *Bioinorg. Chem.* 1976, 5, 283-310 and HOLMBERG, K.; HANSEN, B., ChemInform abstract: ESTER SYNTHESIS WITH DICYCLOHEXYL-CARBODIIMIDE IMPROVED BY ACID CATALYSTS. *Chemischer Informationsdienst* 1980, 11, each of which is incorporated by reference in its entirety. However, since the advent of DCC, a wide variety of efficient coupling reagents that do not suffer from this rearrangement have been developed for solid-phase peptide synthesis. See, Al-Warhi, T. I.;
Al-Hazimi, H. M.; El-Faham, A., Recent development in peptide coupling reagents. *Journal of Saudi Chemical Society* 2012, 16, 97-116, which is incorporated by reference in its entirety. Thus, phosphates may react with these reagents in the same fashion as carboxylates to generate active esters susceptible to nucleophilic attack.

Figure 9:
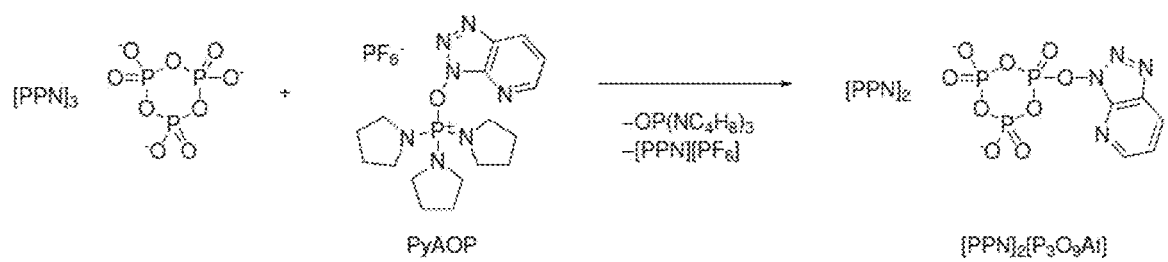
FIG. 9 shows an activation of trimetaphosphate using peptide coupling agent PyAOP: synthesis of new triphosphorylating agent $[PPN]_2[P_3O_9At]$.

Solubilization of metaphosphate ions in polar aprotic organic media can be achieved by utilizing lipophilic organic cations. See, Jiang, Y.; Chakarawet, K.; Kohout, A. L.; Nava, M.; Marino, N.; Cummins, C. C., *J. Am. Chem. Soc.* 2014, 136, 11894-11897 and Klemperer, W. G.; Main, D. J., *Inorg. Chem.* 1990, 29, 2355-2360, each of which is incorporated by reference in its entirety. Furthermore, a methodology was developed to protonate the inorganic rings and generate a library of crystalline metaphosphoric acid salts, thereby expanding the synthetic potential of these materials. See, Chakarawet, K.; Knopf, I.; Nava, M.; Jiang, Y.; Stauber, J. M.; Cummins, C. C., Crystalline metaphosphate acid salts: Synthesis in organic media, structures, hydrogen-bonding capability, and implication of superacidity. *Inorg. Chem.* 2016, 55, 6178-6185, which is incorporated by reference in its entirety. The initial studies focused on the utilization of these soluble metaphosphates as novel, all inorganic ligands for transition metal complexes. See, Stauber, J. M.; Cummins, C. C., Terminal titanyl complexes of tri- and tetrametaphosphate: Synthesis, structures, and reactivity with hydrogen peroxide. *Inorg. Chem.* 2017, 56, 3022-3029 and Stauber, J. M.; Zhang, S.; Gvozdik, N.; Jiang, Y.; Avena, L.; Stevenson, K. J.; Cummins, C. C., Cobalt and vanadium trimetaphosphate polyanions: Synthesis, characterization, and electrochemical evaluation for non-aqueous redox-flow battery applications. *J. Am. Chem. Soc.* 2018, 140, 538-541, each of which is incorporated by reference in its entirety. To advance the investigation of metaphosphates, it became desirable to functionalize these molecules, and, in the case of tetrametaphosphate, the anhydride $[P_4O_{11}]^{2-}$ serves as a reagent for direct tetraphosphorylation. However, no similarly straightforward route presented itself for triphosphorylation, despite this having obvious value as a synthetic target. Initial unsuccessful attempts to activate the acid $[P_3O_9H]^-$ to substitution using DCC, by analogy with the preparation of anhydride $[P_4O_{11}]^{2-}$, ultimately led us to the remarkable discovery that trimetaphosphate, as its PPN salt, reacts rapidly and quantitatively with phosphonium based peptide coupling reagents to give active phosphoesters (FIG. 9).

Synthesis of triphosphorylating agent $[P_3O_9At]^{2-}$

Experiments show that there is a slow (complete in 12-24 h at 25° C. in acetonitrile) but quantitative reaction between $[PPN]_3[P_3O_9]$ and the phosphonium based peptide coupling reagent PyAOP,25 (7-azabenzotriazol-1-yloxy)tripyrrolidinophosphonium hexafluorophosphate, to give a new species, which was assigned as the trimetaphosphate 7-azabenzotriazole phosphoester ($[PPN]_2[P_3O_9At]$, FIG. 9) based upon characterization by multinuclear NMR spectroscopy and mass spectrometry.

Although the PyAOP mediated coupling proceeds in one pot according to the general strategy for triphosphorylation of HNuc (FIG. 3), the active phosphoester intermediate, $[P_3O_9At]^{2-}$ can be isolated and fully characterized. Phosphoesters containing an intact trimetaphosphate ring are almost unknown, and full characterization of this molecule will provide insight into the development of even more potent phosphorylation reagents. See, Cramer, F.; Hettler, H., Zur chemie der "energiereichen phosphate", IV. ester der trimetaphosphorsaure. *Chem. Ber.* 1958, 91, 1181-1188, which is incorporated by reference in its entirety. As a PPN salt, the phosphoester $[P_3O_9At]^{2-}$ should crystallize well from an acetonitrile solution saturated with diethyl ether, when it is of high purity. If necessary, purification can be performed by sequential precipitations from acetonitrile/ diethyl ether, dichloromethane/diethyl ether, or cold acetone. The phosphoester will be characterized by a combination of $^1H$, $^{13}C$, and $^{31}P$ NMR spectroscopy, ESI Mass Spectrometry, Elemental Analysis, and X-ray crystallography. Of principal interest is the stability of this product under both hydrous and anhydrous conditions, as the active phosphoester bond may be prone to hydrolysis.

Figure 10:
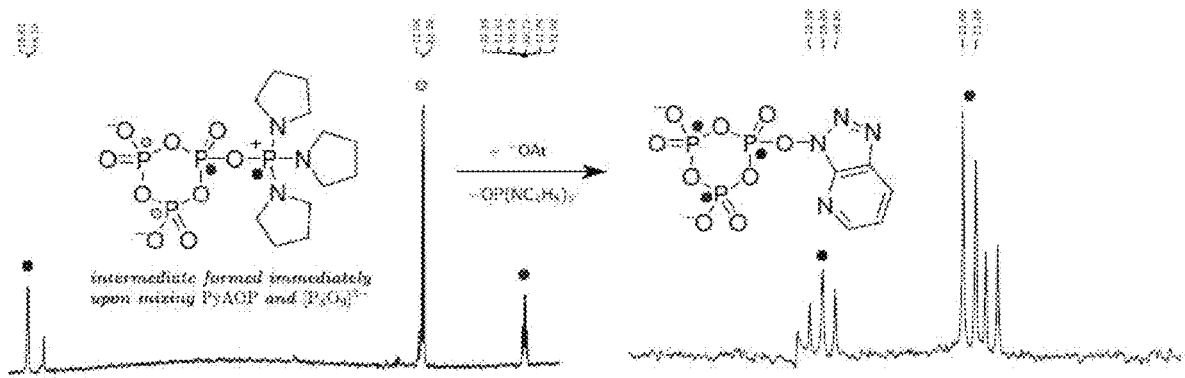
FIG. 10 shows $^{31}P$ NMR spectra showing conversion of initially formed $[P_3O_9P(NC_4H_8)_3]^-$ to $[P_3O_9At]^{2-}$.
Figure 11:
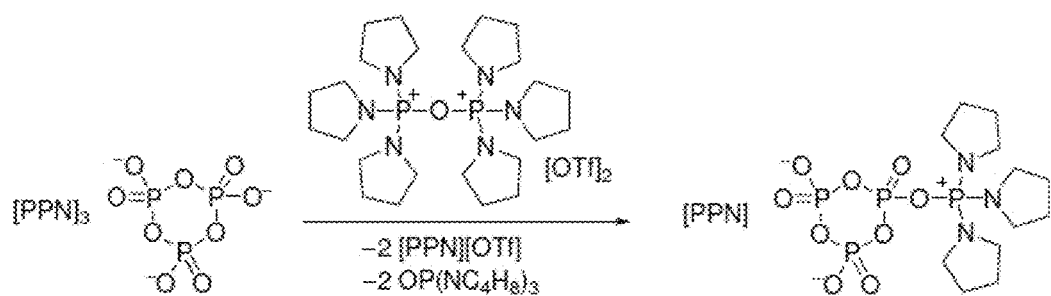
FIG. 11 shows independent generation of $[P_3O_9P(NC_4H_8)_3]^-$ using a phosphonium anhydride reagent in illustration of an alternative approach to activation of metaphosphate rings. See, Hendrickson, J. B.; Hussoin, M. S., Seeking the ideal dehydrating reagent. *J. Org. Chem.* 1987, 52, 4137-4139, which is incorporated by reference in its entirety.

The reaction of PyAOP with trimetaphosphate to generate the activated ester was discovered, $[P_3O_9At]^{2-}$ proceeds by way of an initially generated intermediate now assigned as $[P_3O_9P(NC_4H_8)_3]^-$. The assignment is based upon the $^{31}P$ NMR multiplets observed for this species in a 1:2:1 ratio (FIG. 10). In order to verify this assignment, this species was generated independently by the reaction of the phosphonium anhydride reagent, $[O(P(NC_4H_8)_3)_2][OTf]_2$, with trimetaphosphate as shown in FIG. 11. This was successful in showing that the persistent species so generated has the same $^{31}P$ NMR signals as the intermediate observed when using PyAOP. By generating $[P_3O_9P(NC_4H_8)_3]^-$ in this independent fashion, with HOAt not present in the reaction mixture, it may be possible to isolate and fully characterize this interesting species and to investigate its potential as an alternative phosphorylating agent. That it reacts with $^-OAt$ to generate an already active phosphorylating agent in $[P_3O_9At]^{2-}$ strongly suggests that the new species $[P_3O_9P(NC_4H_8)_3]^-$ may be the most active actor for triphosphorylation yet in the possession. Armed with this information, a similar strategy will be pursued for tetraphosphorylation.

Reactions of triphosphorylating agent $[P_3O_9At]^{2-}$

Preliminary studies show that the novel triphosphorylating agent $[P_3O_9At]^{2-}$ reacts, either after isolation or in a one-pot procedure, with organic and inorganic protic nucleophiles to generate the targeted coupled products. This reactivity highlights a rarely considered structural similarity between phosphates and carboxylates and appears to hold major potential as a fast and mild route to triphosphate functionalized molecules.

Figure 12:
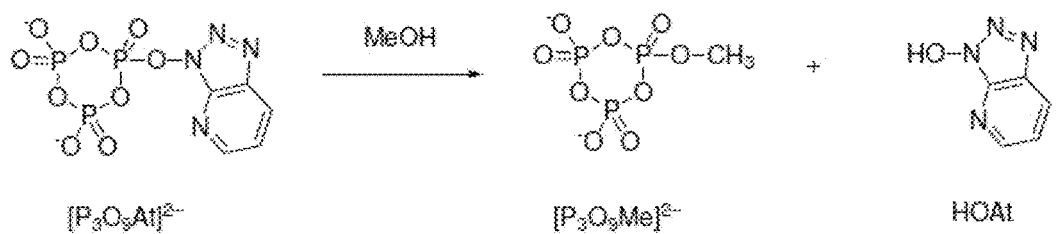
FIG. 12 shows a first synthesis of the trimetaphosphate methyl ester, $[P_3O_9Me]^{2-}$.
Figure 13:
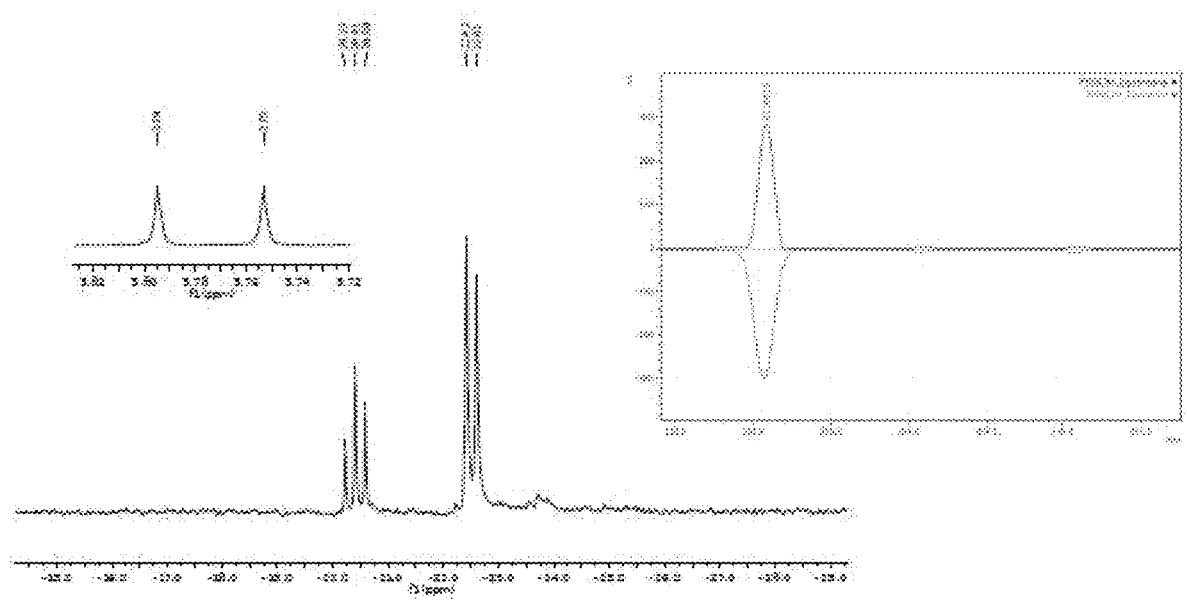
FIG. 13 shows a diagnostic $^{31}P\{^1H\}$ NMR spectrum for $[P_3O_9Me]^{2-}$ with $^1H$ NMR spectrum at upper left (methyl doublet due to $^{31}P$ splitting), and ESI-MS at upper right.

As an initial example, the reaction of in situ generated $[PPN]_2[P_3O_9At]$ with methanol gave rapid and clean conversion to the methyl ester of trimetaphosphate (FIG. 12). The new dianion $[P_3O_9Me]^{2-}$ is characterized by a diagnostic doublet and triplet in its $^{31}P$ NMR spectrum, a methyl doublet in the $^1H$ NMR spectrum, and by its mass spectrum (FIG. 13). The salt $[PPN]_2[P_3O_9Me]$ is obtained as a colorless crystalline solid.

Figure 14:
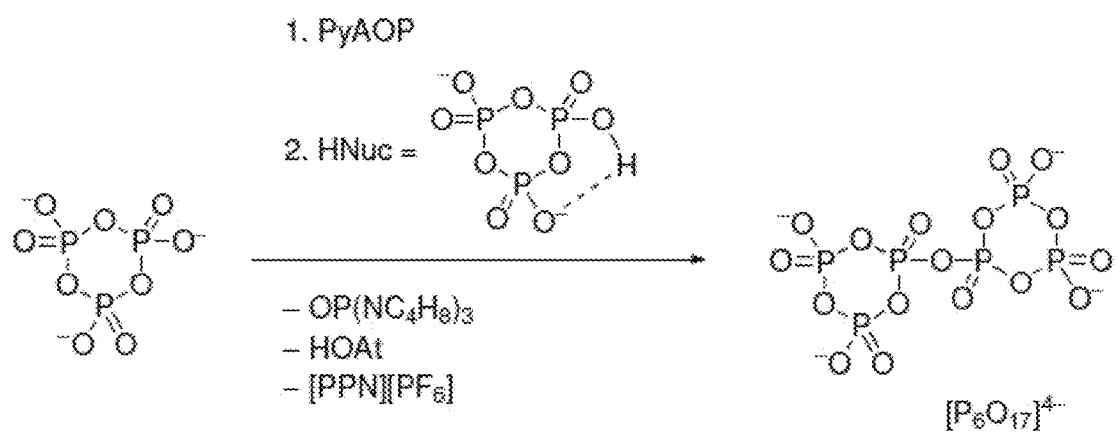
FIG. 14 shows a synthesis of [PPN]4[P6O17] illustrating triphosphorylation of a phosphate.

Initial studies demonstrate the ability of the active trimetaphosphate ester to react with a variety of protic nucleophiles, including $[PPN]_2[P_3O_9H]$ to give the product mentioned above, $[PPN]_4[P_6O_{17}]$, resulting from dehydrative coupling of two trimetaphosphate rings (FIG. 14). Trimetaphosphate is both a weak nucleophile and a weak electrophile; therefore, the ability to efficiently couple two trimetaphosphates demonstrates the power of the synthetic methodology. The use of peptide coupling reagents has also never been demonstrated for monophosphorylation, and this protocol is potentially applicable to a broad range of phosphate substrates. The strategy outlined here (FIG. 3) is applicable generally to a wide variety of synthetic and biochemical substrates, including nucleosides, amino acids, sugars, and fatty acids.

Initial interest in trimetaphosphate functionalization focused on coupling two trimetaphosphates to generate $[PPN]_4[P_6O_{17}]$, a salt containing a novel anion (depicted at right in FIG. 14) which has not previously been isolated. The activated phosphoester $[P_3O_9At]^{2-}$ (At=7-azabenzotriazolyl, see FIG. 9) was found to react instantly and quantitatively with $[PPN]_2[P_3O_9H]$ to give the desired coupled product, $[PPN]_4[P_6O_{17}]$. However, PyAOP is most commonly used as a peptide coupling reagent to generate active carboxylic esters primed for reaction with protic nucleophiles, usually amines. The ease and rapidity with which this reagent coupled two relatively unreactive phosphates excited us for its potential to activate trimetaphosphate towards attack by a wide variety of protic nucleophiles.

The general phosphorylation procedure is nicely illustrated by the case of diethylamine. The procedure involves addition of PyAOP to a solution of $[PPN]_3[P_3O_9]$ and diethylamine in dry acetonitrile, eliciting a color change to yellow is likely due to production of the $^-OAt$ anion. Clean and complete conversion to $[P_3O_8NEt_2]^{2-}$ is complete within minutes according to $^{31}P$ NMR spectroscopic monitoring. After 15 min the product separates from the reaction mixture as a yellow oil, from which the majority of the acetonitrile is removed by decantation.

Figure 16:
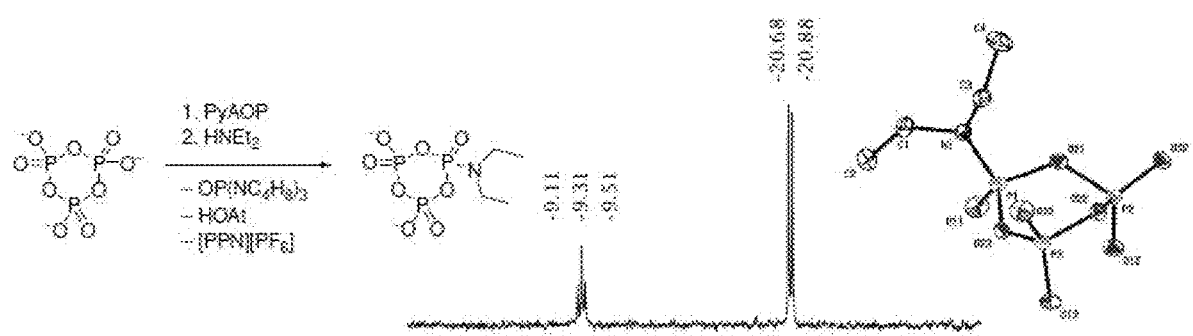
FIG. 16 shows a triphosphorylation of diethylamine with $^-P$ NMR spectrum and crystal structure (hydrogens and cations omitted for clarity.

Drying under vacuum provides a solid material, subsequently obtained as colorless needles upon crystallization from a mixture of acetone and diethyl ether. The structure shown in FIG. 16 was obtained by X-ray crystallography.

A Variety of Triphosphorylation Agents and Substrates

Figure 15:
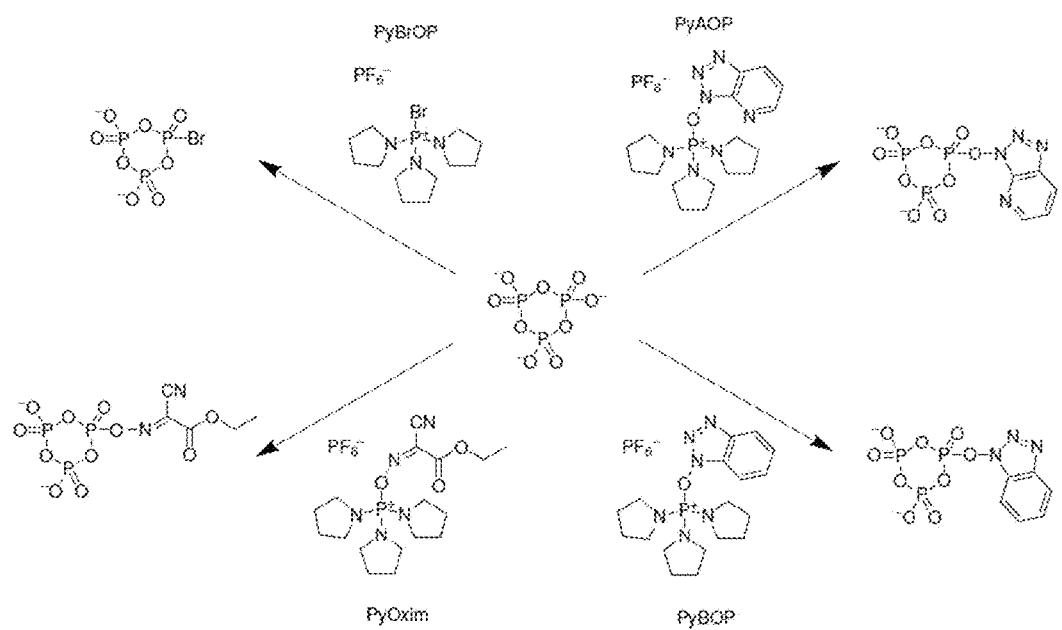
FIG. 15 shows a phosphonium peptide coupling reagents to canvass for application in polyphosphorylation.

A potential wide variety of related molecules is envisioned to synthesize and test as phosphorylation reagents. Of the uronium class of peptide coupling reagents, HATU was effective in the synthesis of $[PPN]_4[P_6O_{17}]$, but the yield were lower than when using PyAOP. Different phosphonium based reagents such as PyBOP, PyBrOP, and PyOxim can yield superior phosphorylation reagents (FIG. 15). Additionally, in the case of PyBrOP and PyOxim, the explosive potential of the benzotriazole unit of PyBOP and PyAOP is avoided. Additionally, these other phosphonium reagents are synthesized by reaction of PyBrOP with the corresponding hydroxylamine in the presence of a tertiary amine base. See, Hoffmann, F.; Jäger, L.; Griehl, C., Synthesis and chemical constitution of diphenoxyphosphoryl derivatives and phosphonium salts as coupling reagents for peptide segment condensation. *Phosphorus, Sulfur, and Silicon and the Related Elements* 2003, 178, 299-309, which is incorporated by reference in its entirety. It may be able to synthesize functionalized trimetaphosphates by first generating the corresponding phosphonium coupling reagents in an analogous manner with PyBrOP and the desired substrate.

The ability of this PyAOP mediated phosphorylation procedure on unprotected nucleosides can be tested. The active phosphoester should react with the most acidic and least sterically hindered nucleophilic site, thus phosphorylation should proceed selectively at the 5' position. The degree of selectivity as partial phosphorylation of 2', 3', or even amine positions are possible in theory can be investigated. The products of reactions that proceed cleanly will be facilely worked up by filtration to remove insoluble material and addition of diethyl ether to precipitate the products. Repeated crystallizations or purification by reverse phase chromatography may be necessary, but phosphorylation protocols can minimize the use of excess reagents and by which pure products can be isolated with a minimum of subsequent manipulation. Reactions will be monitored by $^1$H and $^{31}$P NMR spectroscopy, and products will be characterized analogously to the previously mentioned phosphoesters. It will be of interest to characterize the initial products of phosphorylation, those that contain intact cyclophosphate rings, and then subsequently determine the stability of these initial products and the conditions under which they will undergo hydrolytic ring-opening to provide the corresponding linear forms. The PPN counterions of the initial phosphorylated products may easily be exchanged for biologically relevant counterions, such as sodium and ammonium, by addition of the corresponding triflate salt to an acetonitrile solution of the product, resulting in immediate precipitation of the desired compound; the [PPN][OTf] generated in the process of cation exchange is soluble in acetonitrile and thus easily separated.

Figure 17:
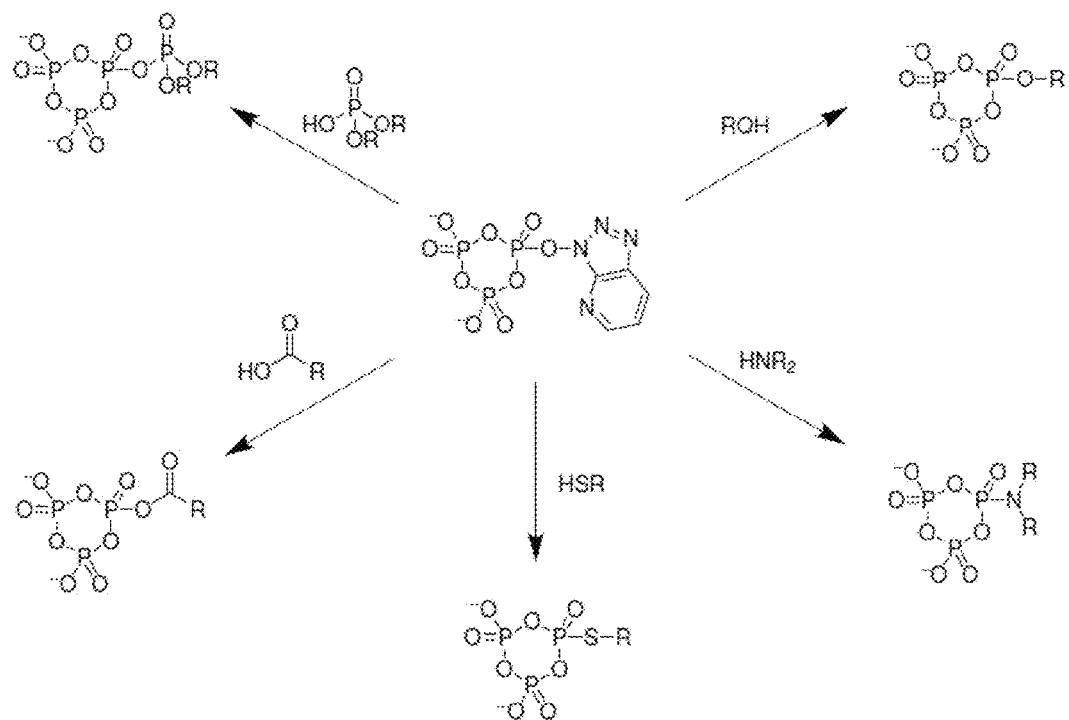
FIG. 17 shows a functional groups to be canvassed for direct polyphosphorylation.

PyAOP mediated phosphorylation (FIG. 3) can extend beyond improved synthesis of nucleoside triphosphates, as a variety of protic nucleophiles are likely suitable substrates (FIG. 17). Some relevant protic nucleophiles include amines, thiols, carboxylic, phosphoric, and phosphonic acids. Initial studies will utilize small test molecules bearing the functional groups of interest so that the selectivity of the procedure can be confirmed and analyzed. These reactions will be studied by a combination of NMR spectroscopy and mass spectrometry, and products will be isolated and characterized as described previously. If these reactions are successful, the procedure may be utilized to phosphorylate a wide variety of biomolecules including sugars, fatty acids, amino acids, peptides, proteins, metabolites, and steroids. Many biomolecules have never been polyphosphorylated and studied, but the simple phosphorylation procedures will allow access to such constructs. In collaboration with chemical biology, biochemical, and biology groups these new molecules can be studied as enzymatic inhibitors and therapeutic drugs. Furthermore, peptide coupling reagents may react with other phosphates such as orthophosphate, pyrophosphate, and tetrametaphosphate, potentially facilitating the synthesis of any desired phosphate chain length.

Tetraphosphorylation

Direct tetraphosphorylation can be achieved by "tet1", distinct from the method above (FIG. 3) to be used for direct triphosphorylation, while the second, "tet2" is completely analogous.

Figure 18:
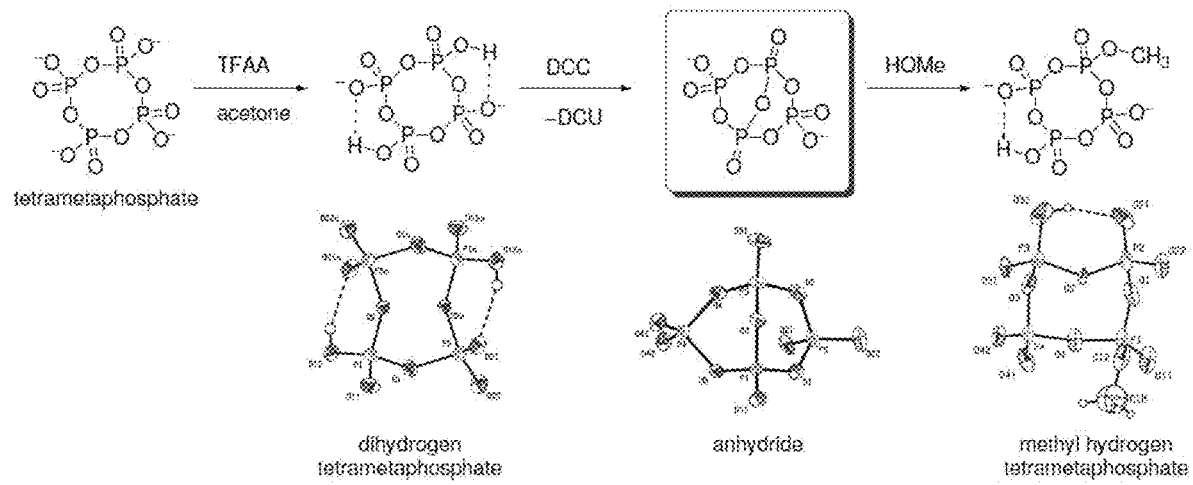
FIG. 18 shows a synthesis of tetraphosphorylating agent anhydride $[P_4O_{11}]^{2-}$ (see box), obtained as its crystalline PPN salt, and tetraphosphorylation of methanol.

Tetraphosphorylation using anhydride $[P_4O_{11}]^{2-}$, "tet1" approach $[PPN]_2[P_4O_{11}]$ can be obtained as a pure crystalline salt that is soluble in polar aprotic organic media by virtue of the lipophilic cations, that is a reagent for direct tetraphosphorylation. The synthesis of $[PPN]_2[P_4O_{11}]$ is accomplished in a two-step procedure beginning from the PPN salt of tetrametaphosphate (FIG. 18). The first step is treatment with TFAA in acetone, on the benchtop in air, leading to the high yield precipitation of dihydrogen tetrametaphosphate as its PPN salt, $[PPN]_2[P_4O_{12}H_2]$; the salt so obtained was fully characterized including a single-crystal X-ray diffraction study revealing a pair of intramolecular hydrogen bonds in the anion. The second step, carried out under anhydrous conditions, is the dehydration of the anion using DCC. The product of the dehydration reaction, the anhydride of dihydrogen tetrametaphosphate, $[P_4O_{11}]^{2-}$, was similarly obtained as its PPN salt in high yield as a crystalline compound and fully characterized including X-ray analysis. The salt, $[PPN]_2[P_4O_{11}]$, was found to give direct phosphorylation of methanol via cleavage of its reactive central P—O—P anhydride linkage under mild conditions. The product of the methanol reaction, HNuc=HOMe, is the methyl ester of monohydrogen tetrametaphosphate, which was isolated as its crystalline PPN salt $[PPN]_2[P_4O_{12}HMe]$, and fully characterized including an X-ray diffraction study (FIG. 18). This sequence illustrates the synthesis and characterization of a new reagent for direct tetraphosphorylation of protic nucleophiles, HNuc. An advantage of this strategy for tetraphosphorylation is that the reaction with HNuc proceeds atom economically with no formation of byproducts. There is no need for using a peptide coupling reagent in this approach because the anhydride $[P_4O_{11}]^{2-}$ essentially contains its own internal phosphate leaving group at the location of the central reactive P—O—P linkage.

Figure 19:
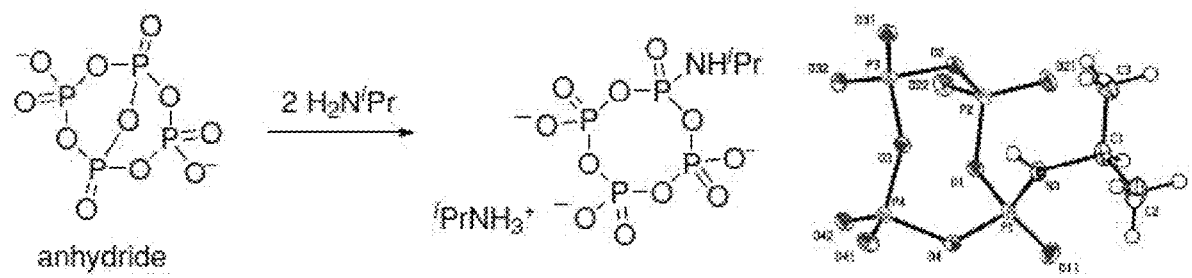
FIG. 19 shows a tetraphosphorylation of isopropyl amine. The two [PPN]$^-$ counter ions are not shown and the H-bonded [$^i$PrNH$_3$]$^+$ ion is omitted from the thermal ellipsoid plot.

Demonstrating that the anhydride $[P_4O_{11}]^{2-}$ can be used to tetraphosphorylate primary amines is the example involving isopropyl amine (FIG. 19). Two equivalents of iPrNH$_2$ react at 25° C. within minutes to provide the new trianion $[P_4O_{11}NH^iPr]^{3-}$, which crystallized from MeCN/Et$_2$O together with the two [PPN]$^-$ and one [iPrNH$_3$]$^+$ counter ions. This example shows that when a basic nucleophile, in this case HNuc=H$_2$N$^i$Pr, is utilized, a second equivalent of HNuc can be used to neutralize the acidic protonated tetraphosphate moiety that is otherwise produced.

It will be important to determine the capacity of the tri and tetraphosphorylating agents to react selectively with nucleophiles that contain more than one potential site for phosphorylation. The expectation is that stronger nucleophiles will react preferentially, and that less sterically crowded nucleophiles will be preferred as well.

Figure 20:
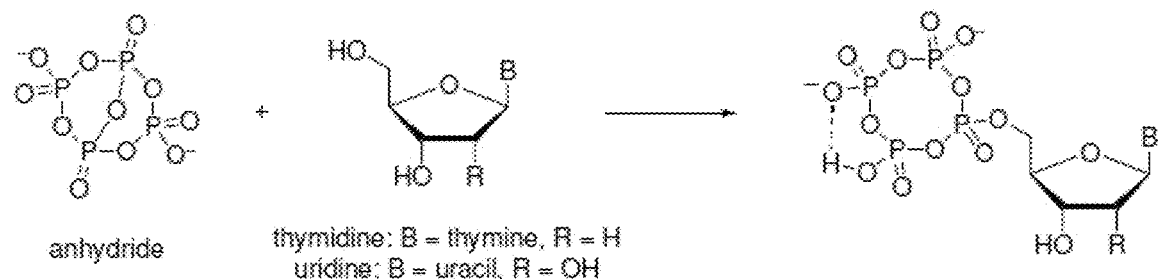
FIG. 20 shows a tetraphosphorylation of thymidine and uridine.

As an initial test case, the reactions of unprotected thymidine and uridine were investigated with the $[P_4O_{11}]^{2-}$ anhydride. While the reactions were sluggish at 25° C., at 39° C. they appeared to be complete after 4 h. Monitoring by $^{31}$P NMR spectroscopy indicated conversion to one major product in both cases with a pattern of signals consistent with the expectation for tetraphosphorylation at the 5' position (FIG. 20). Analysis by ESI-MS showed a strong signal at m/z corresponding to [M+H]$^-$ for the products of thymidine and uridine tetraphosphorylation. The products have been isolated as white powders and are undergoing further characterization.

Nucleosides are expected to be selectively phosphorylated at the 5' position, as it is the most sterically accessible and nucleophilic. The characterization will allow us to determine if this is the case and determine if any side products are present in which other sites are phosphorylated. The next step will be to expand this synthetic scheme to a variety of nucleosides and related substrates and develop efficient syntheses and purification protocols for these species as well. Nucleosides that contain an amine functional group may require protecting group chemistry.

The innovative approach described in the present section is simpler and distinct from all previous strategies for tetraphosphorylation in that it is direct and results initially in phosphorylated products which are isolated as crystalline salts with their tetrametaphosphate rings intact. These rings are expected to convert to the linear forms upon applying appropriate hydrolysis conditions (to be determined).

Figure 4:
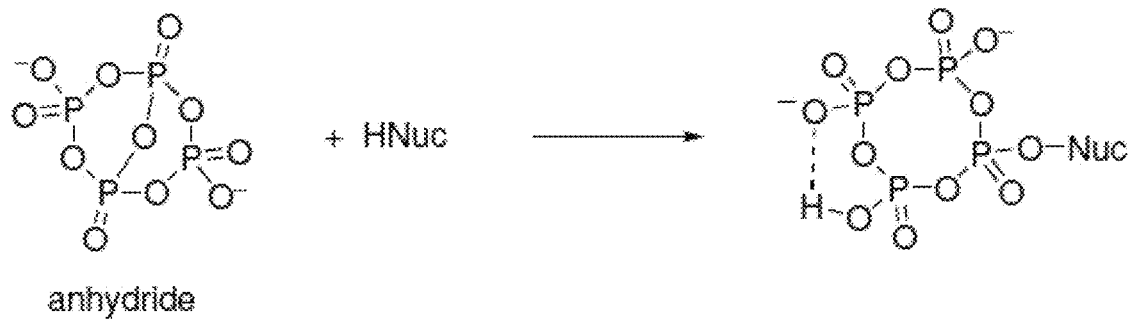
FIG. 4 shows a generalized strategy "tet1" for direct tetraphosphorylation of protic nucleophiles.
Figure 5:
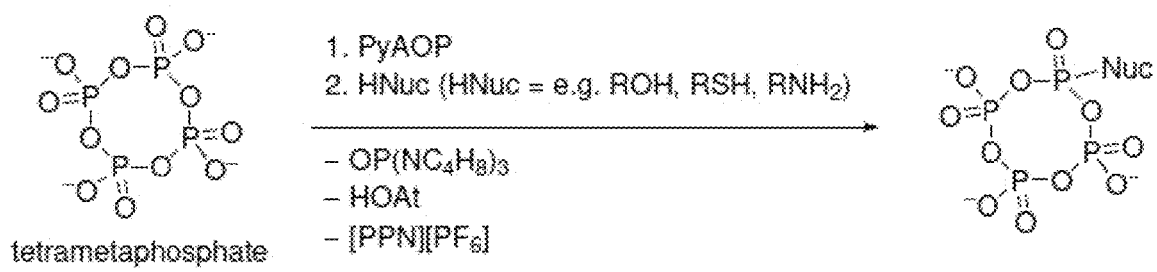
FIG. 5 shows a generalized strategy "tet2" for direct tetraphosphorylation of protic nucleophiles.

Our initial results show that anhydride $[P_4O_{11}]^{2-}$ reacts with a variety of protic nucleophiles (FIG. 4). The library of reactions can be expanded to include a variety of alcohols, amines, thiols, carboxylic acids, and inorganic acids of varying steric profiles and electronic environments. Exploring the synthetic reaction scope in this manner will allow extension of the methodology to a wider variety of biomolecules including amino acids and lipids.

Tetraphosphorylation Using Peptide Coupling Agents, "tet2" Approach

The second innovative approach anticipated for direct tetraphosphorylation mirrors the use of peptide coupling reagents as described above for triphosphorylation. Multiple routes are envisioned for generating novel active tetraphosphorylating agents in this case, the first being reaction of HOAt with the anhydride $[P_4O_{11}]^{2-}$ as in the general strategy "tet1" for direct phosphorylation using the anhydride (FIG. 4). This may be done in combination with a base to absorb the acidic proton absorbed upon addition of HOAt to $[P_4O_{11}]^{2-}$ in forming $[P_4O_{12}HAt]^{2-}$.

Additionally, with the "tet2" strategy (FIG. 5), one can expand the PyAOP mediated phosphorylation procedure that is proposed for trimetaphosphorylation to tetrametaphosphate. Tetrametaphosphate can be tested with a variety of different peptide coupling reagents such as PyAOP, PyBOP, PyBrOP, PyOxim, and HATU to generate active phosphoesters. The resulting species will be fully characterized, and the phosphorylation activity and selectivity of these reagents can be investigated compared to anhydride $[P_4O_{11}]^{2-}$.

With new tetrametaphosphorylated species in hand, their hydrolysis to linear tetraphosphate can be an improved synthesis of these compounds. In addition, at neutral pH tetrametaphosphate does not readily hydrolyze in water. See, Montag, M.; Clough, C. R.; Müller, P.; Cummins, C. C., Cyclophosphates as ligands for cobalt(III) in water. *Chem. Commun.* 2011, 47, 662-664, which is incorporated by reference in its entirety. Therefore, tetrametaphosphorylated biomolecules may have interesting biological properties. Longer term, in collaboration with chemical biology, biochemical, and biology researchers can investigate the potential of these molecules as enzymatic substrates, inhibitors, and therapeutic agents.

When using PyAOP and related phosphonium based peptide coupling reagents, the isolable active ester species is usually the HOAt ester. See, Castro, B.; Dormoy, J.; Evin, G.; Selve, C. *Tetrahedron Letters* 1975, 16, 1219-1222, which is incorporated by reference in its entirety. However, a reasonable mechanism for PyAOP mediated peptide coupling involves nucleophilic attack on the backside of the phosphonium moiety, resulting in a phosphonium ester as the kinetic product, in analogy with 2. Subsequent attack by the OAt anion would give the anticipated OAt ester as the thermodynamic product. See, Hoeg-Jensen, T.; Holm, A.; Sorensen, H. *Synthesis* 1996, 1996, 383-387, which is incorporated by reference in its entirety. This carboxylate phosphonium ester intermediate has been reported for bulky substrates such as 2,4,6-trimethylbenzoic acid. See, Coste, J.; Frerot, E.; Jouin, P. *The Journal of Organic Chemistry* 1994, 59, 2437-2446, which is incorporated by reference in its entirety.

Single crystal X-ray diffraction revealed that 2 contains two waters of crystallization hydrogen bonded to a phosphate oxygen. This phosphonium species is mildly water sensitive in solution and hydrolyzes over the course of approximately 24 hours to give trimetaphosphoric acid. However, the reaction of $[PPN]_3[P_3O_9]$ $H_2O$ and PyAOP in acetone proceeds in less than thirty minutes and precipitates 2 as a pure tan powder. However, hydrolysis or decomposition in the solid state at room temperature was not observed, and this species is stable for at least two weeks in open air conditions.

Figure 24:
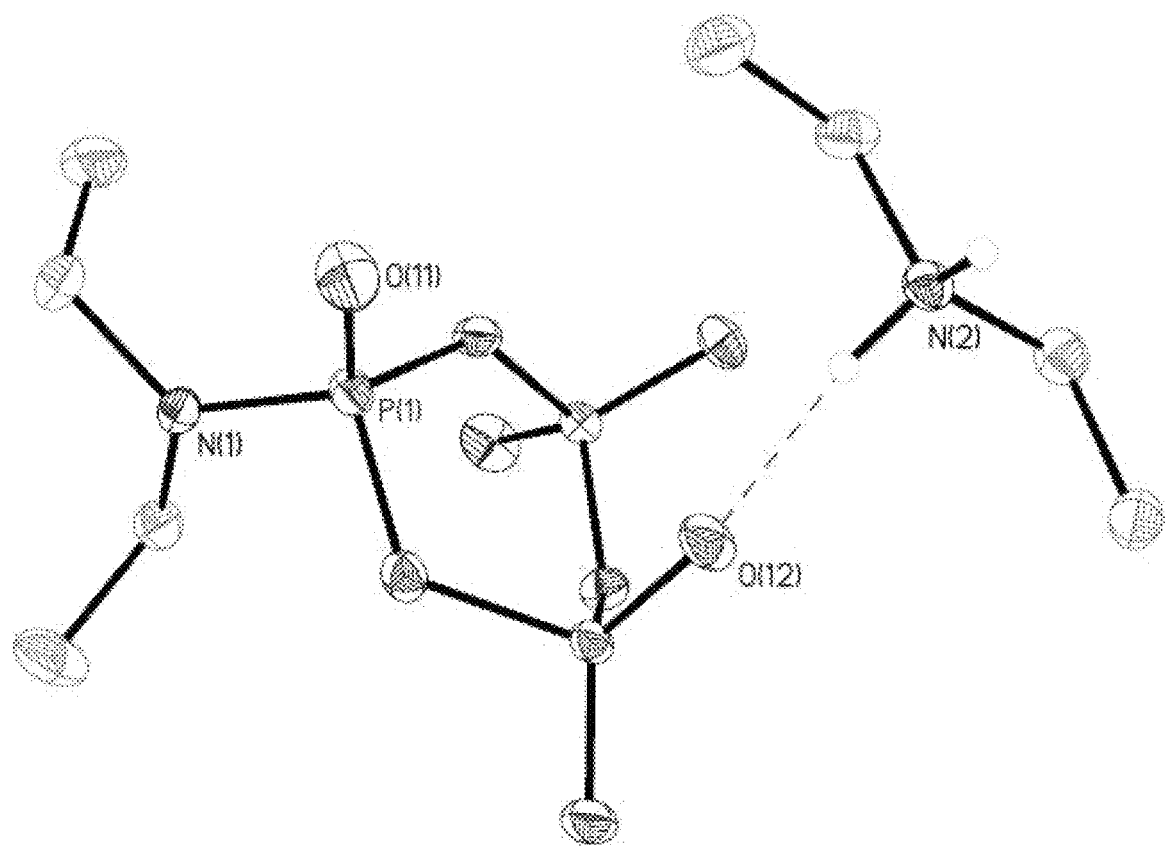
FIG. 24 shows a single Crystal X-ray Structure of 3a with Thermal Ellipsoids set at 50% and the PPN Counterion and Most Hydrogens Omitted for Clarity.
Figure 25:
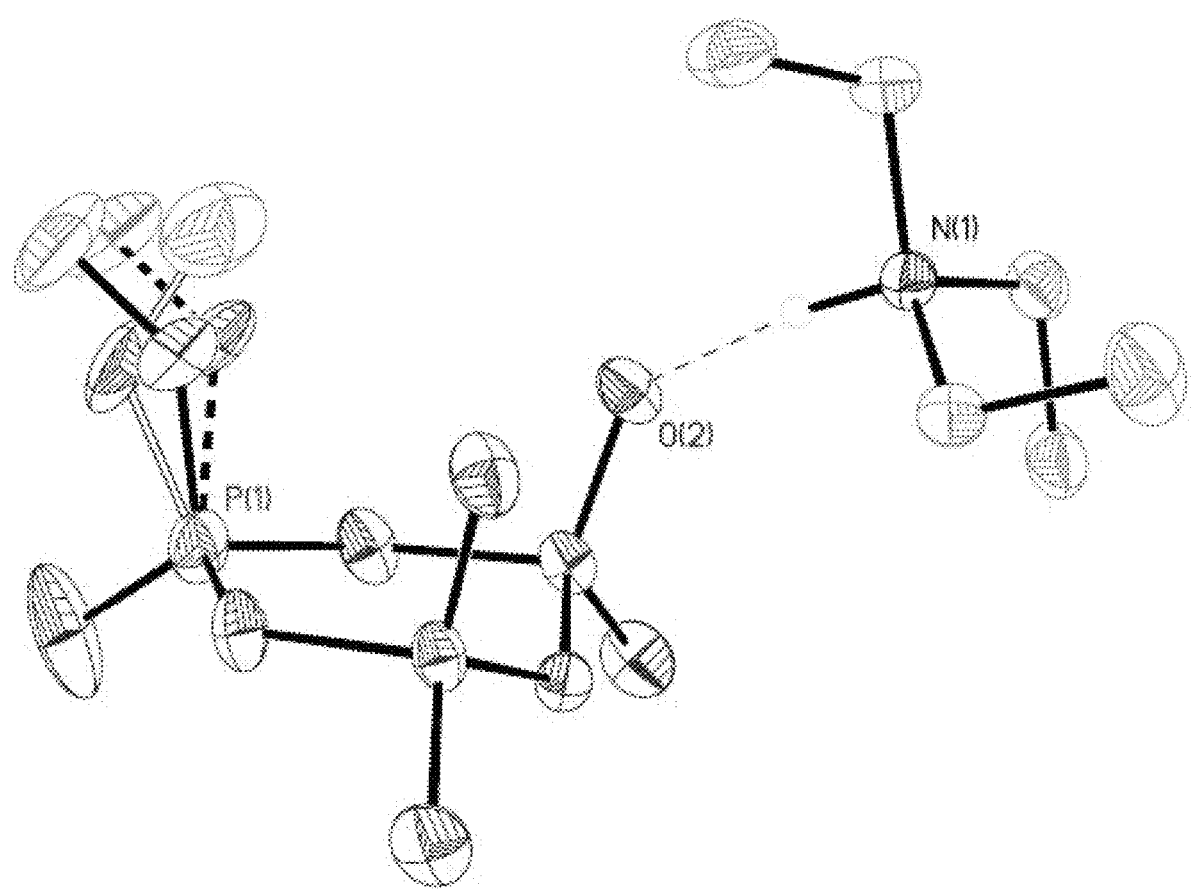
FIG. 25 shows a single Crystal X-ray Structure of 3a with Thermal Ellipsoids set at 50% and the PPN Counterion and Most Hydrogens Omitted for Clarity.
Figure 26:
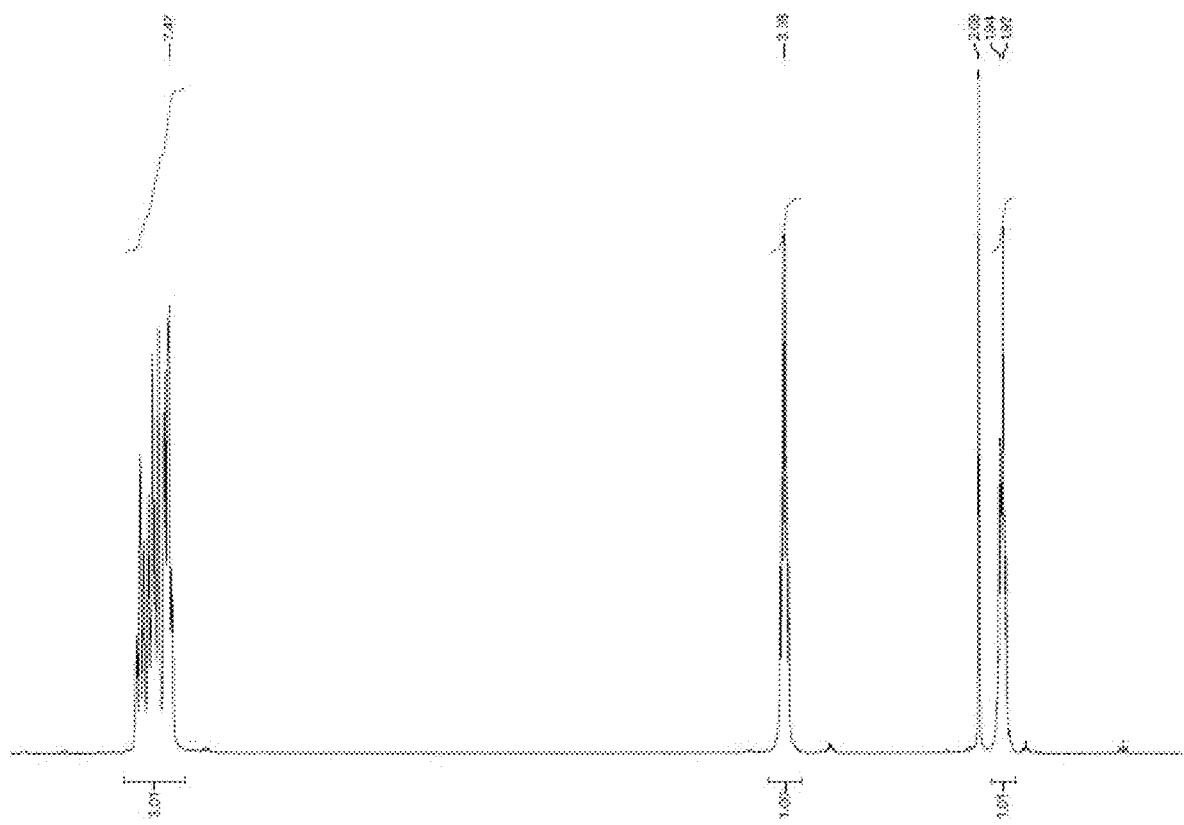
FIG. 26 shows a $^1H$ NMR spectrum of 2 (acetonitrile-d$_3$, 300 MHz).
Figure 27:
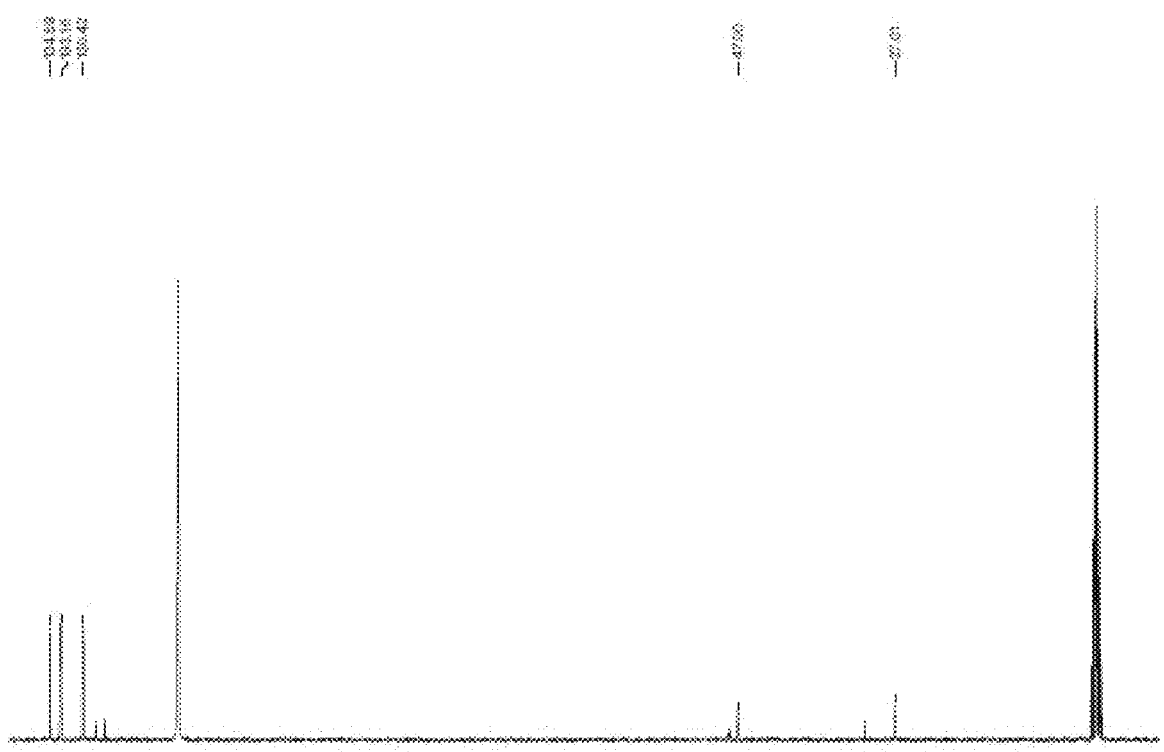
FIG. 27 shows a $^{13}C\{^1H\}$ NMR spectrum of 2 (acetonitrile-d$_3$, 100.6 MHz).
Figure 28:
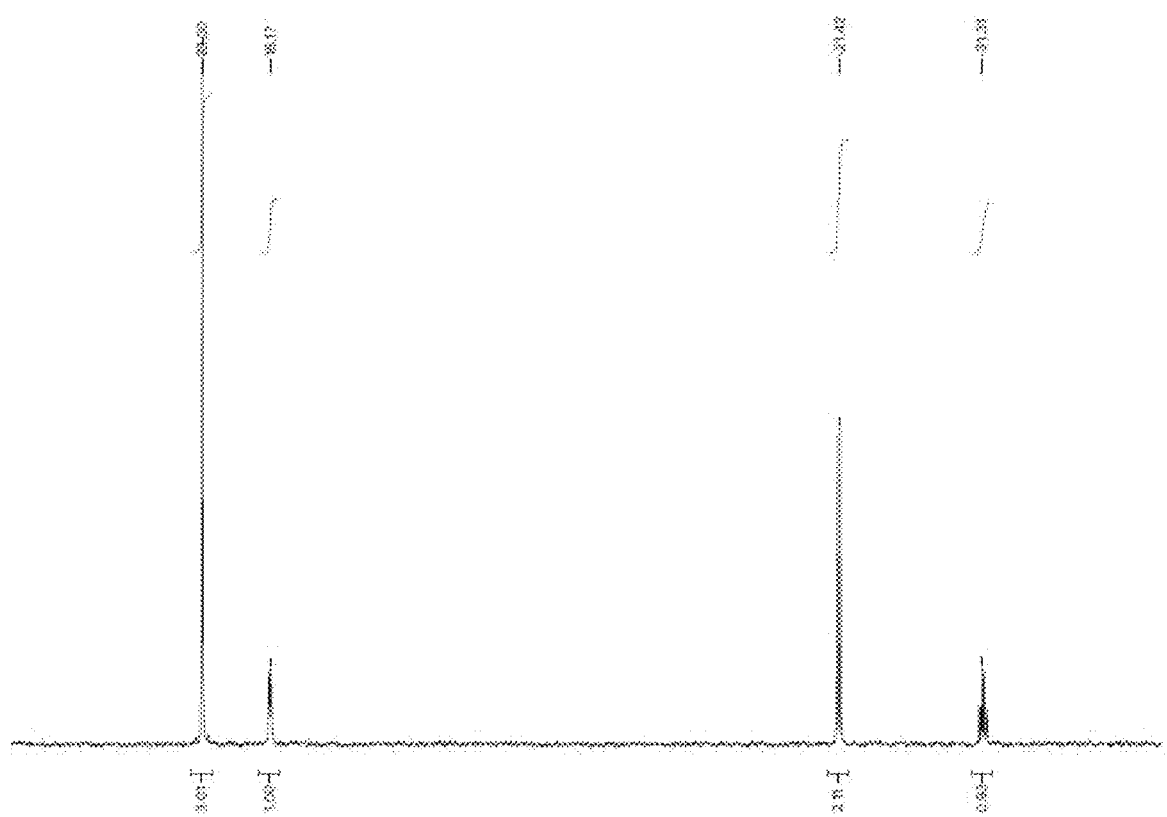
FIG. 28 shows a $^{31}P\{^1H\}$ NMR spectrum of 2 (acetonitrile, 121.4 MHz).
Figure 29:
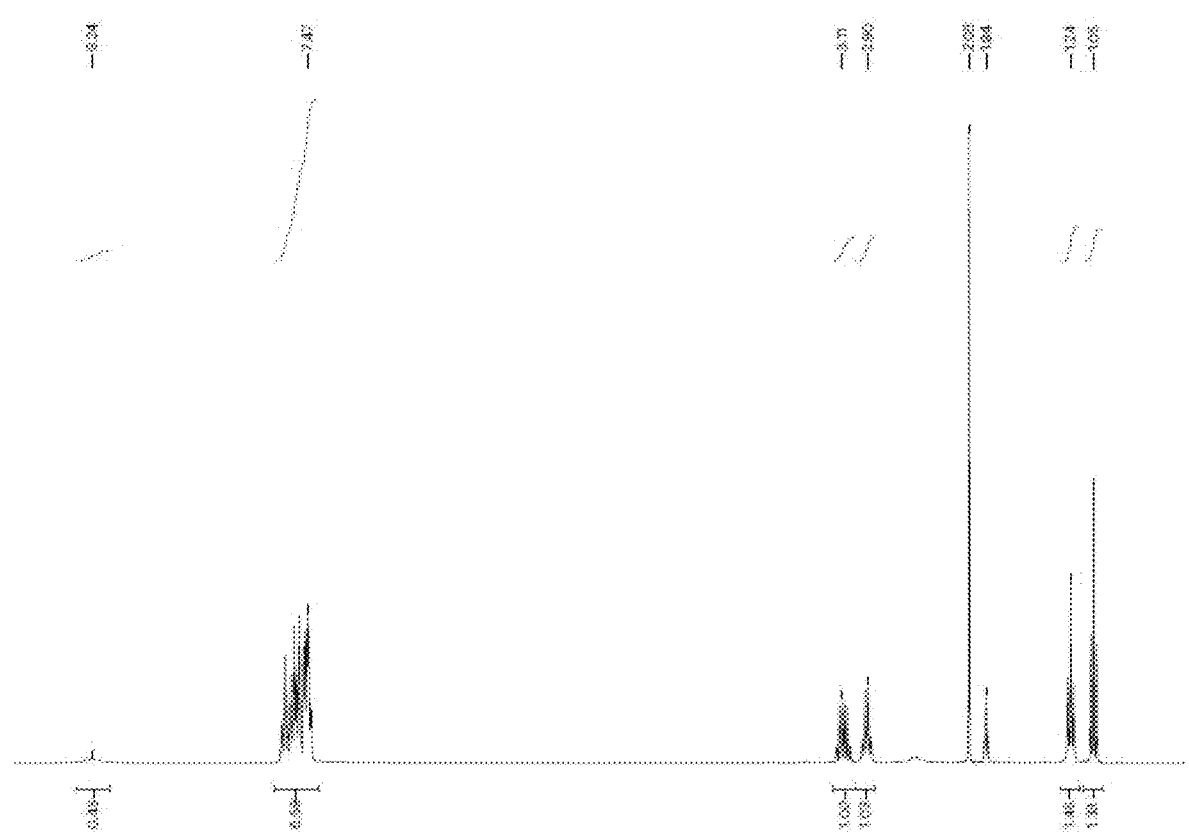
FIG. 29 shows a $^1H$ NMR spectrum of 3a [3b] (acetonitrile-d$_3$, 300 MHz).
Figure 30:
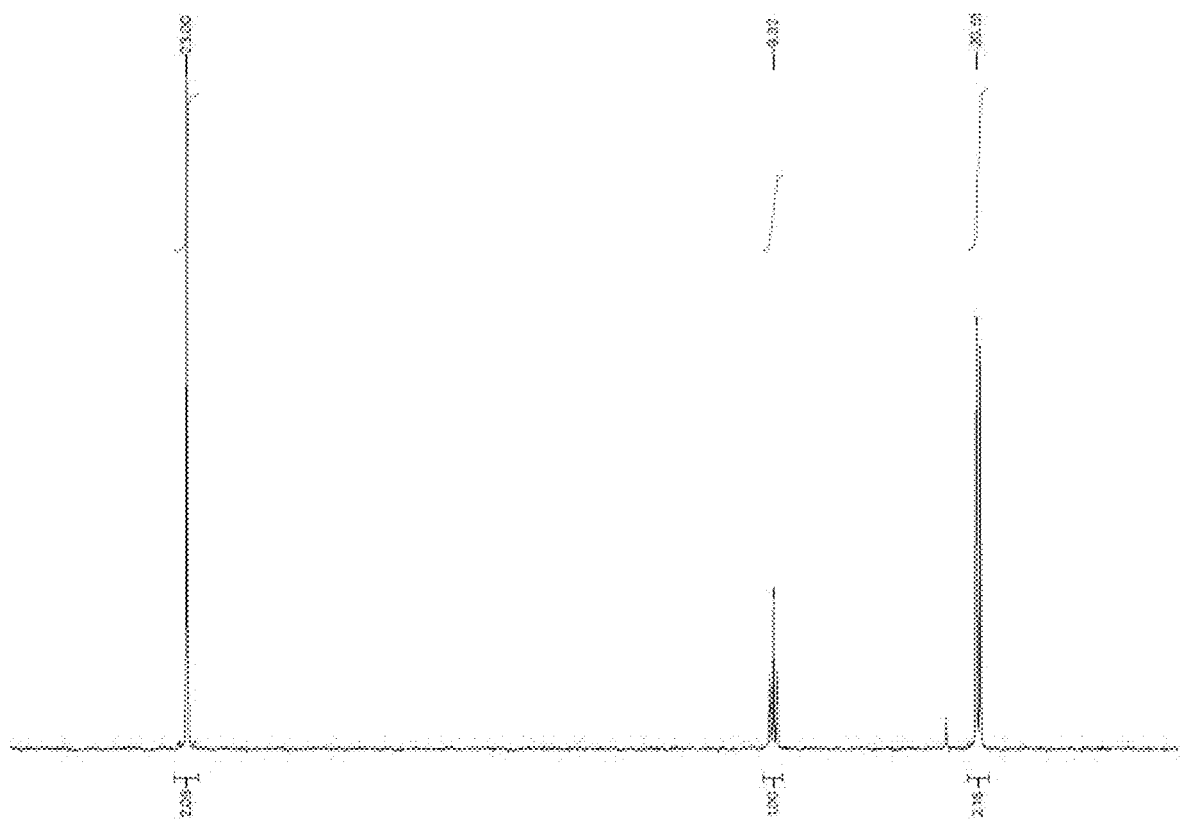
FIG. 30 shows a $^{31}P\{^1H\}$ NMR spectrum of 3a (acetonitrile, 121.4 MHz).
Figure 31:
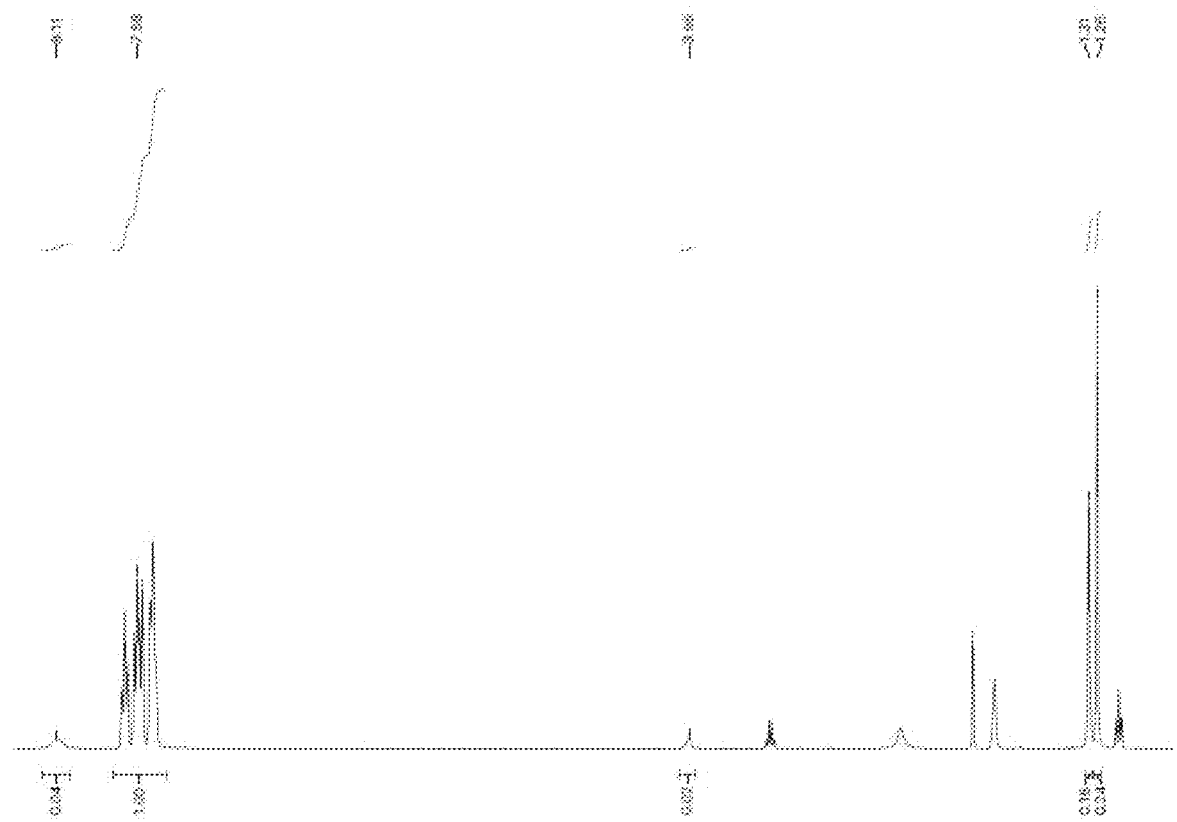
FIG. 31 shows a $^1H$ NMR spectrum of 3b (acetonitrile-d$_3$, 400 MHz).
Figure 32:
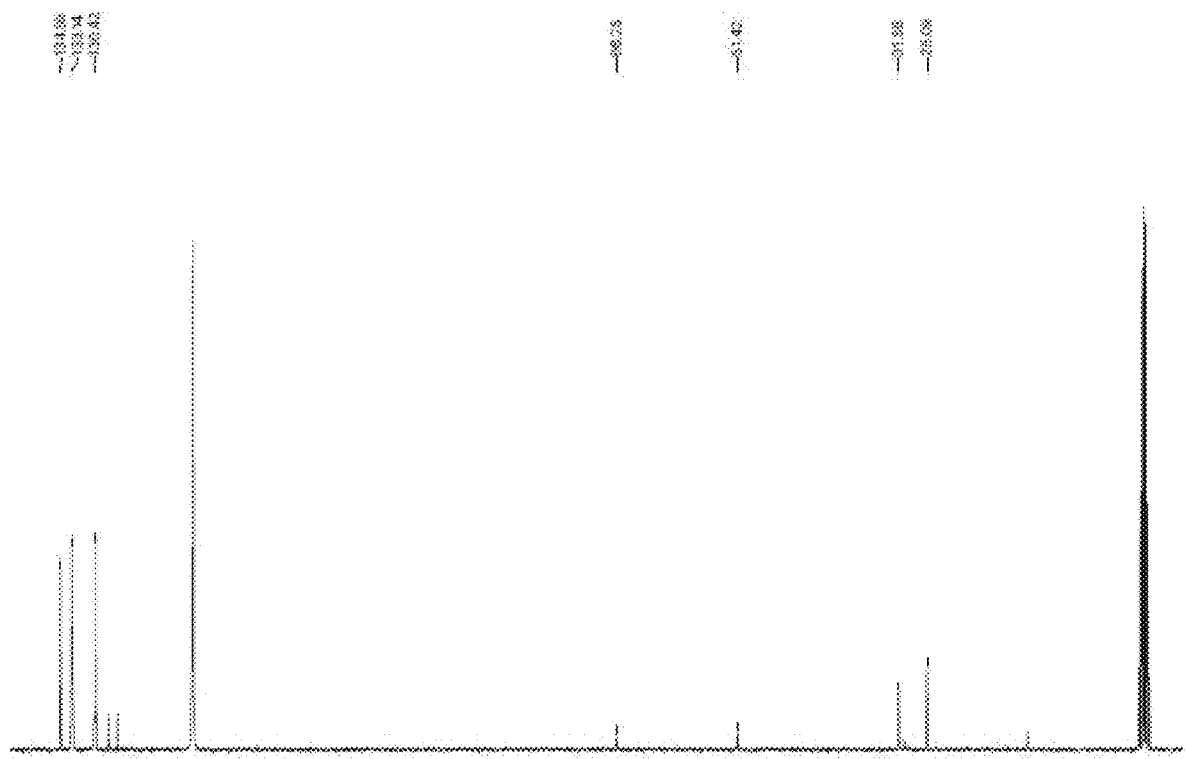
FIG. 32 shows a $^{13}C\{^1H\}$ NMR spectrum of 3b (acetonitrile-d$_3$, 100.6 MHz).
Figure 33:
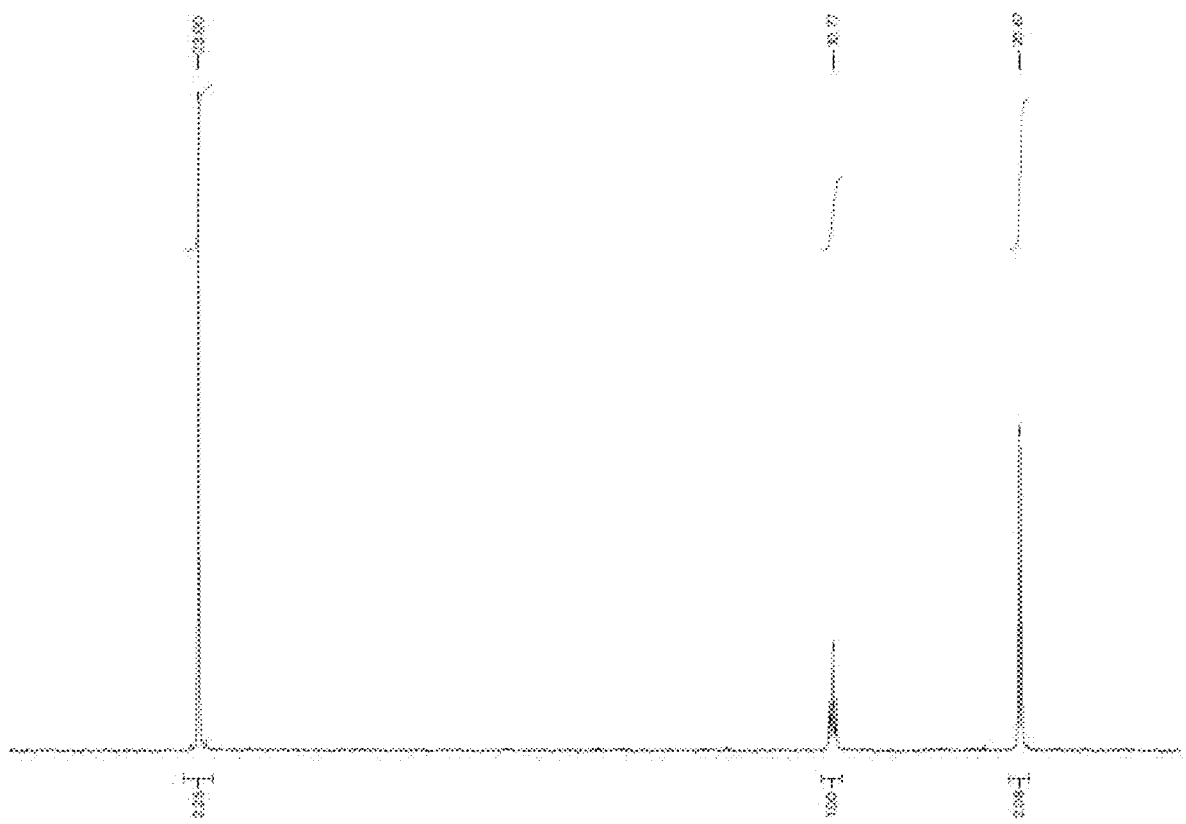
FIG. 33 shows a $^{31}P\{^1H\}$ NMR spectrum of 3b (acetonitrile, 121.4 MHz).
Figure 34:
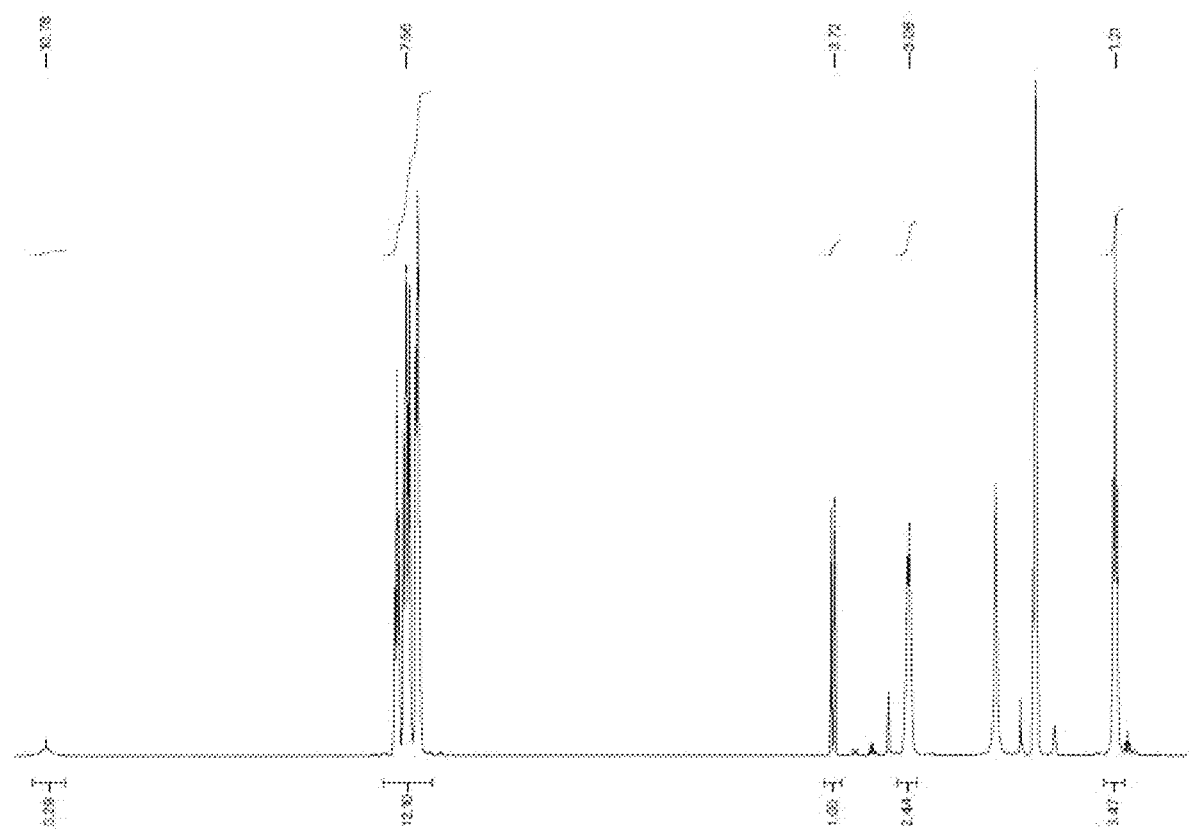
FIG. 34 shows a $^1H$ NMR spectrum of 4a (acetonitrile-d$_3$, 400 MHz) (3a).
Figure 35:
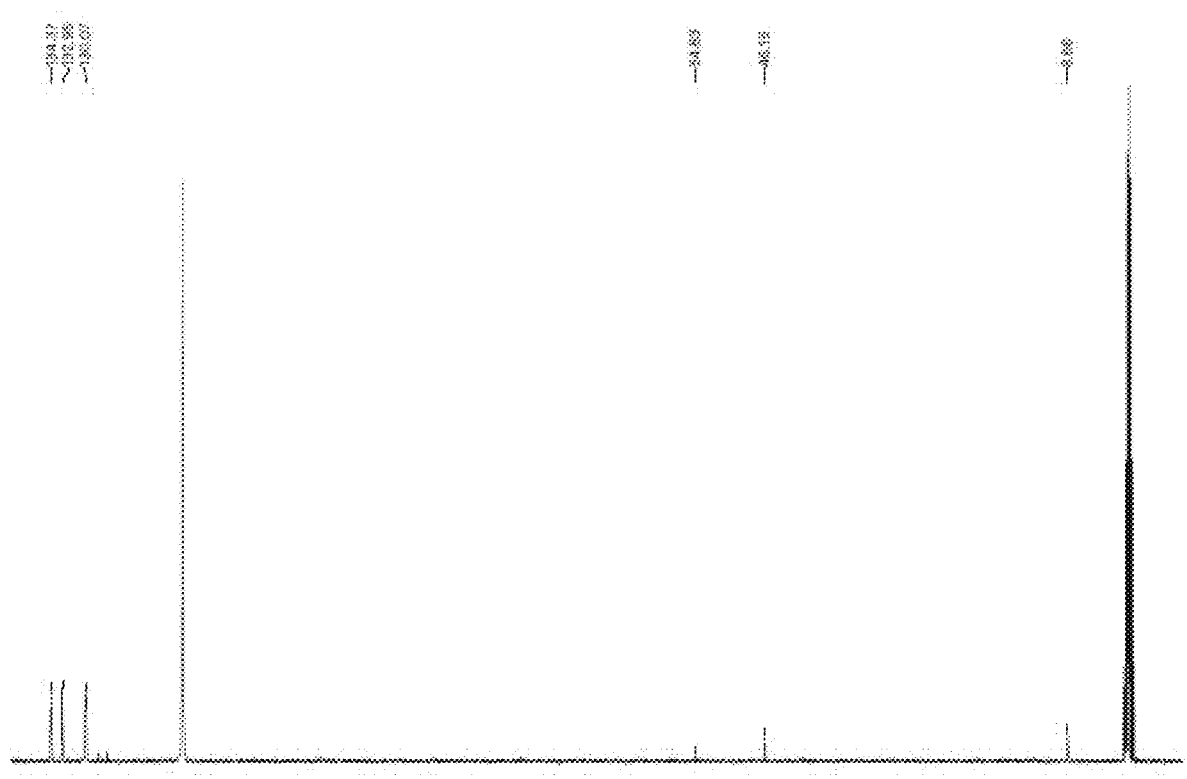
FIG. 35 shows a $^{13}C\{^1H\}$ NMR spectrum of 4a (acetonitrile-d$_3$, 100.6 MHz).
Figure 36:
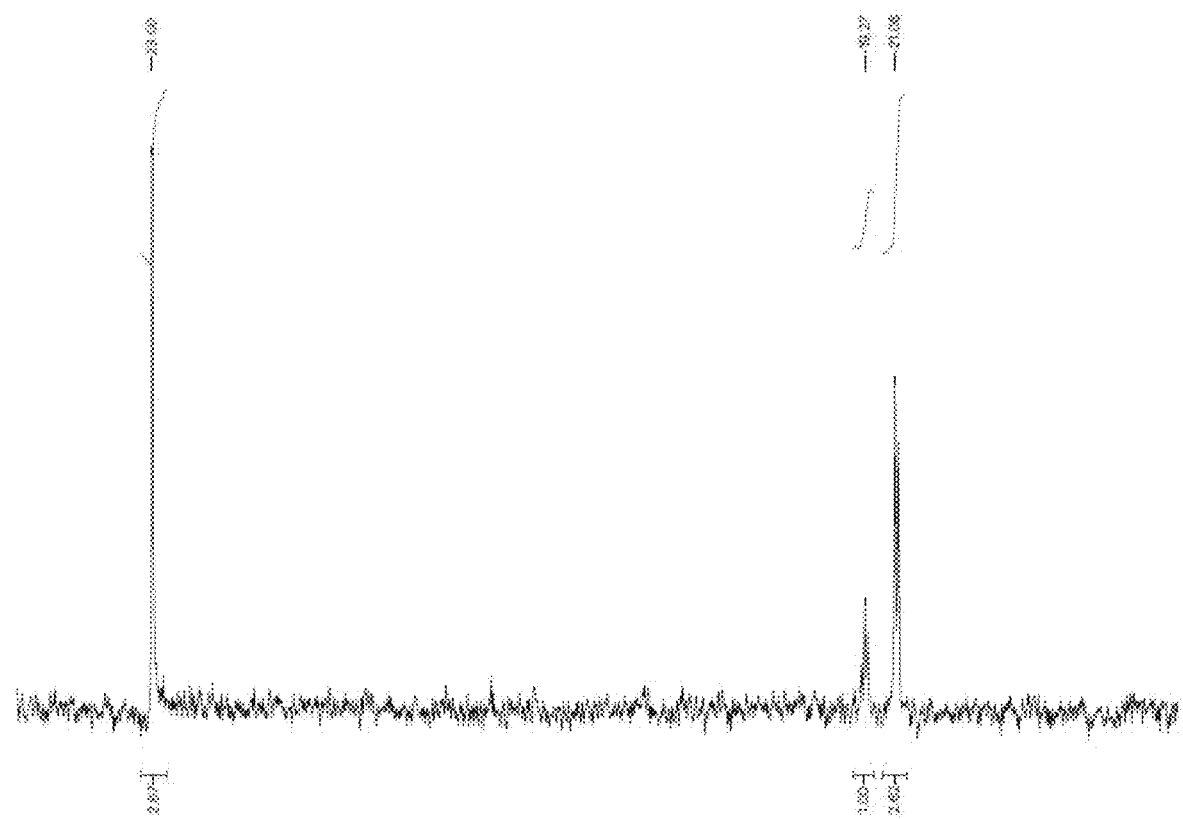
FIG. 36 shows a $^{31}P\{^1H\}$ NMR spectrum of 4a (acetonitrile, 121.4 MHz).
Figure 37:
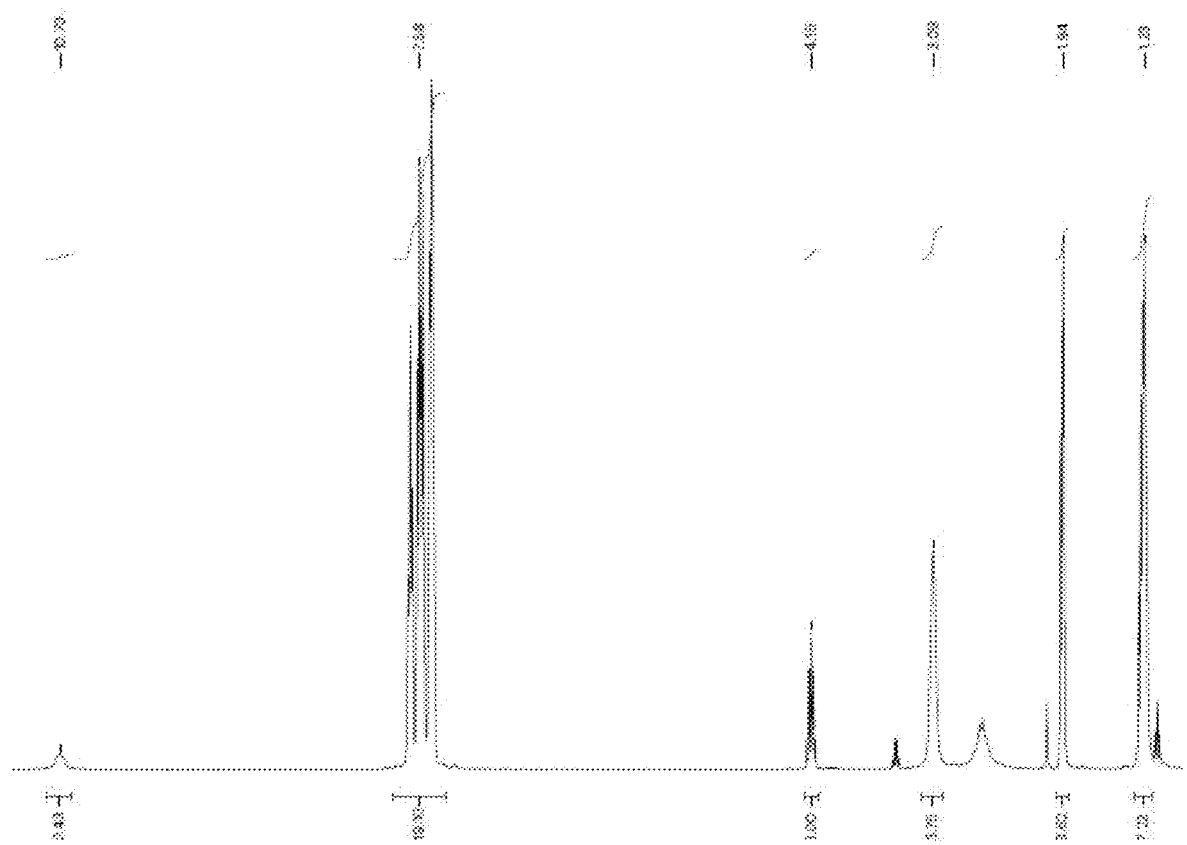
FIG. 37 shows a $^1H$ NMR spectrum of 4b (acetonitrile-d$_3$, 400 MHz).
Figure 38:
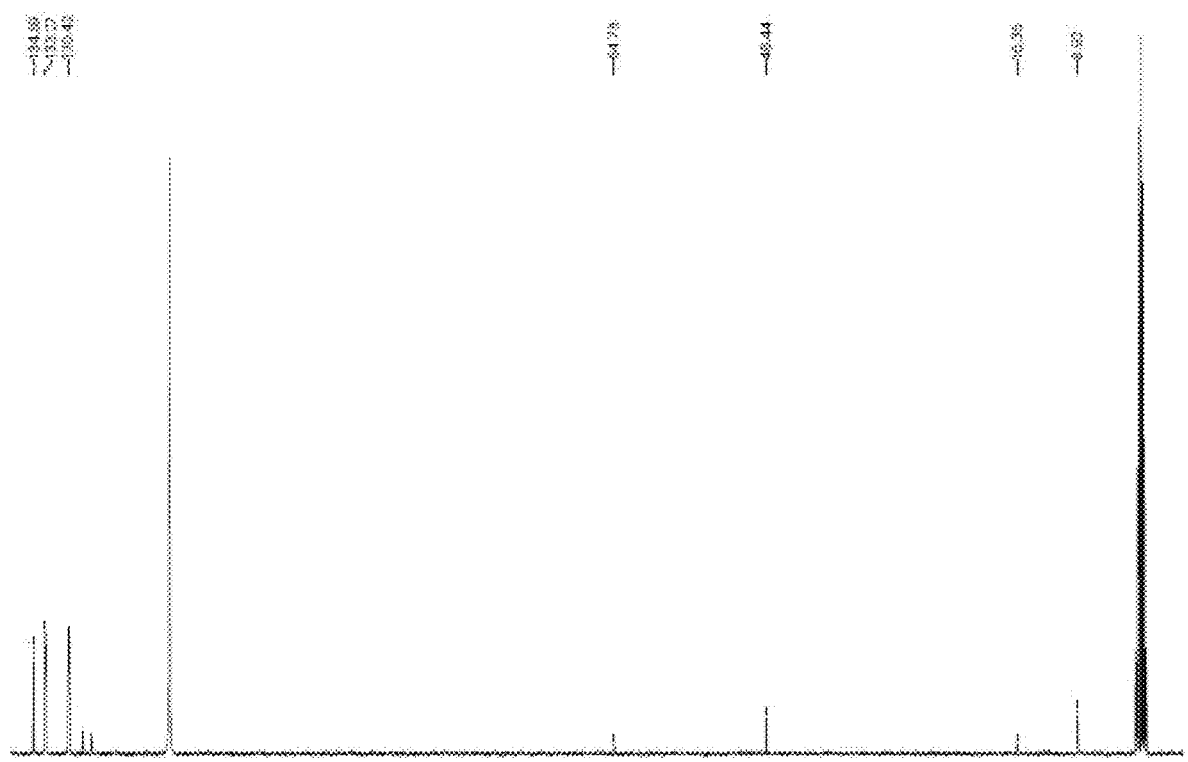
FIG. 38 shows a $^{13}C\{^1H\}$ NMR spectrum of 4b (acetonitrile-d$_3$, 100.6 MHz).
Figure 39:
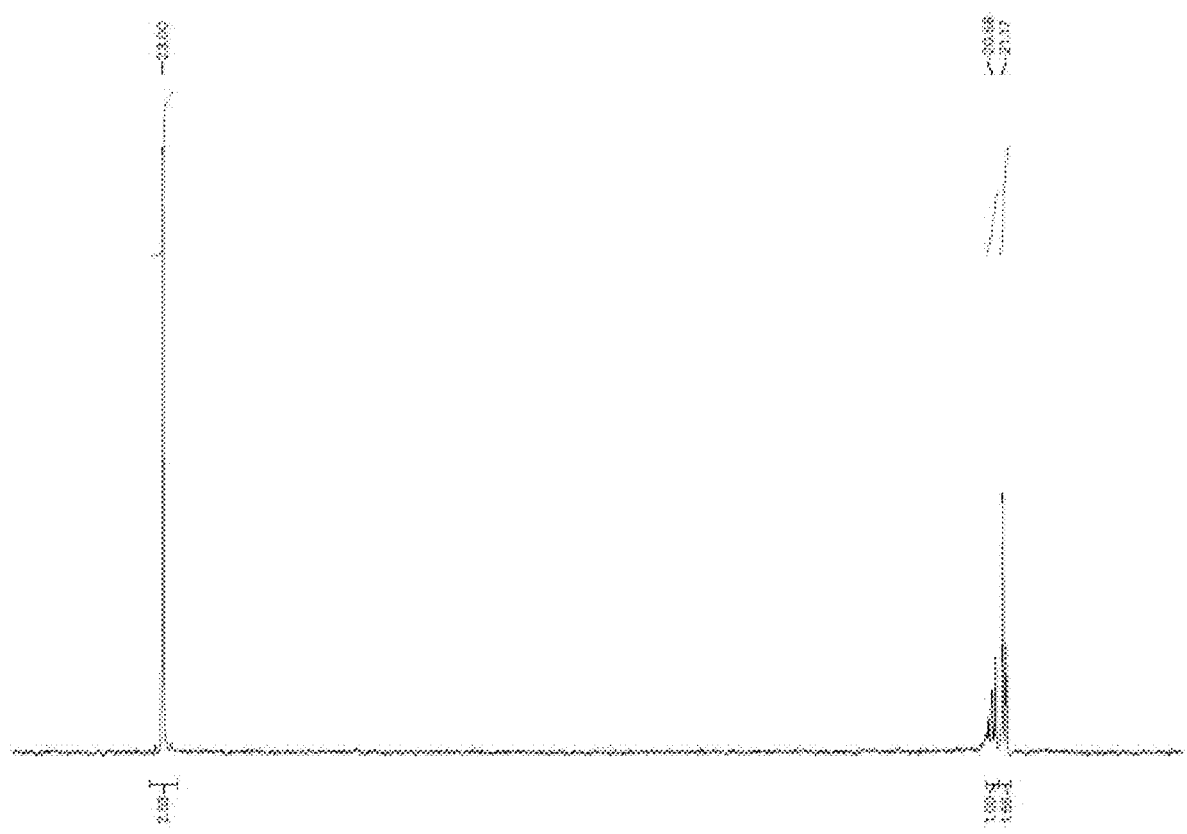
FIG. 39 shows a $^{31}P\{^1H\}$ NMR spectrum of 4b (acetonitrile, 121.4 MHz).
Figure 40:
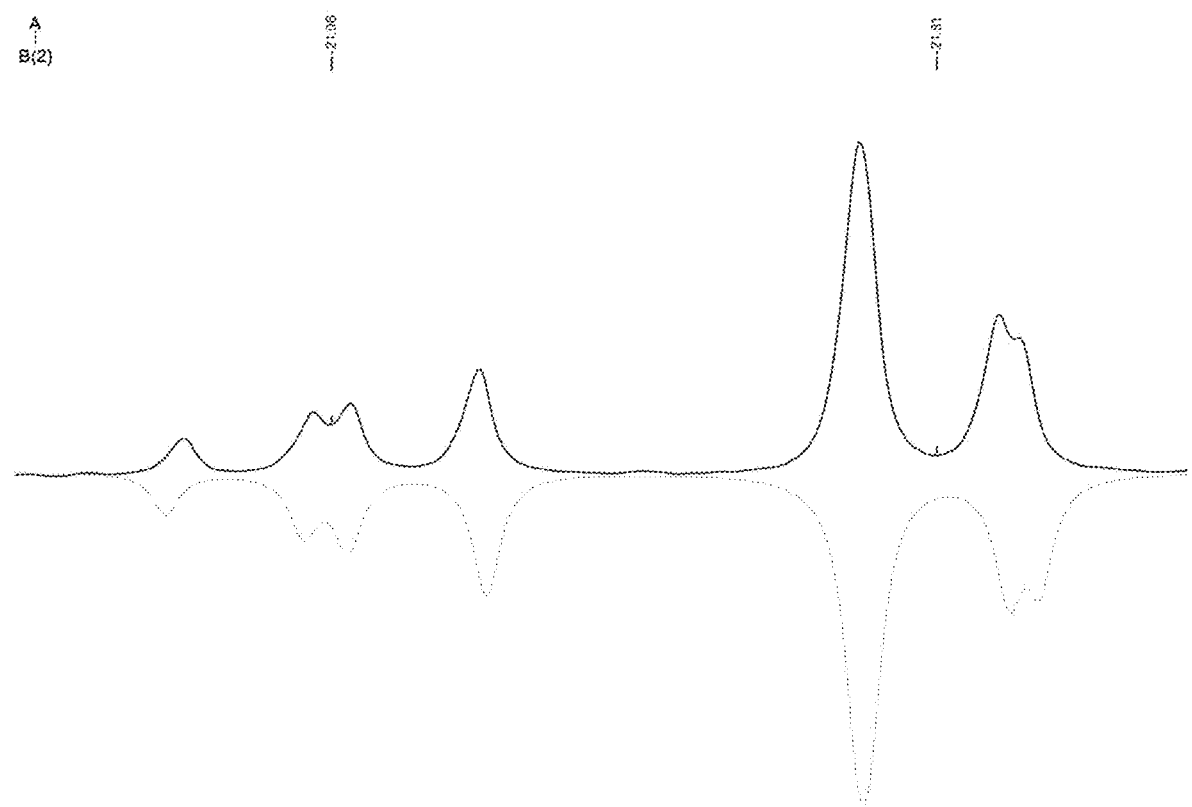
FIG. 40 shows a simulated $^{31}P\{^1H\}$ NMR spectrum of 4b (acetonitrile, 121.4 MH.

Addition of a nucleophile to 2 generates a phosphine oxide as an extremely good leaving group. Therefore, 2 is a potent phosphorylation reagent, and its chemistry and substrate scope is being explored. 2 reacts instantly and quantitatively by NMR with both tbutyl amine and diethyl amine to give the corresponding phosphoramidate species, 7a and 7b. The former was characterized by single crystal X-ray diffraction (FIG. 24). The resulting species are surprisingly robust, as heating them to 80° C. in the presence of methanol or benzoic acid in acetonitrile for 24 hours does not result in any reaction or decomposition. In contrast, phosphoramidates of ortho phosphate typically react with alcohols under mild conditions to give the resulting phosphoester. See, Oney, I.; Caplow, M. *Journal of the American Chemical Society* 1967, 89, 6972-6980, which is incorporated by reference in its entirety. The chemistry of these trimetaphosphate based phosphoramidates as ligands for transition metals is being explored.

As alcohols are poorer nucleophiles than amines, the reaction between 2 and alcohols is less rapid and more prone to hydrolysis. However, the reaction with methanol and ethanol proceed in greater than 50% yield by phosphorus NMR and reasonable isolated yields over the course of several hours depending on conditions. 3a was also characterized by single crystal X-ray diffraction (FIG. 3). Notably, no product of the reaction between 2 and either isopropanol nor t-butanol have ever been observed, indicating a strong selectivity for primary alcohols. Furthermore, these reactions were attempted under rigorously anhydrous conditions conditions inside a glovebox. However, even in the presence of 4A molecular sieves or calcium hydride similar rates of hydrolysis are observed. It is possible to rationalize this observation by noting the two water molecules hydrogen bonded to 2, and all experiments were performed under open air conditions with benchtop solvents.

The reaction of 2 with alcohols necessarily generates an acidic proton, which unlike in the case of amines is not inherently scavenged by substrate. The presence and choice of exogenuous base has a strong impact on selectivity. With no added base, the phosphonium reagent is consumed in less than an hour. However, the expected trimetaphosphate ester is simultaneously consumed by ring opening with another equivalent of alcohol to give the linear diester in addition to hydrolysis products. Addition of triethylamine completely inhibits ring-opening but extends the reaction time to approximately 4 hours in the case of methanol and 16 hours in the case of ethanol. As a result, as much as 50% of 2 is consumed by hydrolysis. Pyridine, a weaker base, reduces hydrolysis and speeds reaction time to approximately one hour. However, the resulting products do not crystallize under the same conditions, giving only oils instead. Subsequent addition of triethylamine exchanges the pyridinium counterion for triethylammonium, generating 3a or 3b.

Figure 22:
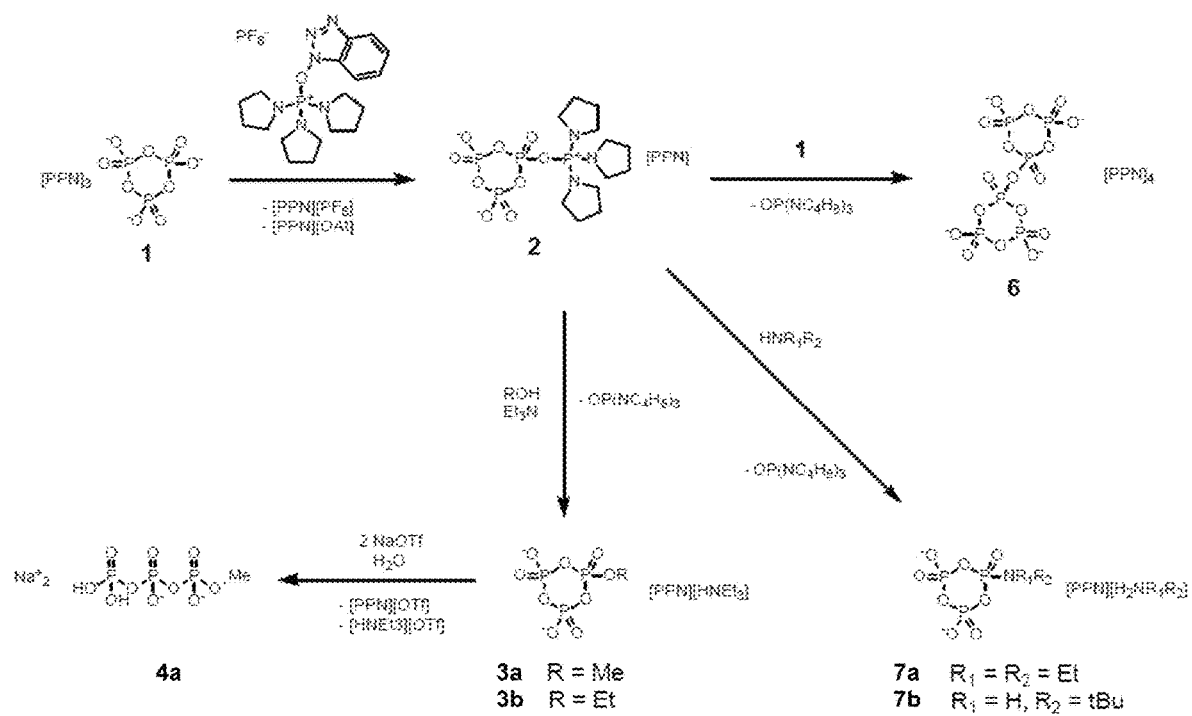
FIG. 22 shows synthesis of Phosphorylating Reagent 2 and Representative Phosphorylation Reactions.

Functionalized trimetaphosphates are almost unknown, and these molecules can be of interest both as new ligands as well as for their potential novel behavior in biological systems. However, if the linear triphosphate species are desired, they can be synthesized in only one additional simple step from the cyclic metaphosphate species. Treating an acetonitrile solution of 3a with sodium triflate results in immediate precipitation of the sodium salt, a process which should be general to both a variety of triflate salts such as magnesium or ammonium triflate and any PPN trimetaphosphate salt (FIG. 22). Filtration to collect the product and subsequent dissolution in neutral water gives quantitative conversion to 4a by $^{31}P$ NMR in less than an hour. The dependence on pH and counterion on the stability of these trimetaphosphate derivatives in aqueous solutions can be investigated.

The high activity of the phosphorylation reagent inspires exciting possibilities for new phosphate architectures. As an initial foray, it has been demonstrated that 2 species reacts with an additional equivalent of 1 over approximately 24 hours to give [PPN]$_4$[P$_6$O$_{17}$], 6, which has been observed by NMR but never before isolated. See, Glonek, T.; Van Wazer, J. R.; Kleps, R. A.; Myers, T. C. *Inorganic Chemistry* 1974, 13, 2337-2345, which is incorporated by reference in its entirety. The success of this reaction is significant as trimetaphosphate is a very weak nucleophile. Not only is 6 very promising ligand, but it also provides a proof of concept for a range of PyAOP mediated phosphate couplings. This strategy can be utilized to synthesize a variety of novel extended phosphate architectures.

Here the reaction between trimetaphosphate and the peptide coupling reagent PyAOP as well as the preliminary studies of the resulting species as a phosphorylating agent has been reported. This new reagent provides convenient access to a previously unstudied class of molecules, mono substituted trimetaphosphate esters and phosphoramidates, as well as their linear analogs. Study of these molecules is underway as well as extending this strategy to more complex biomolecules including nucleosides, amino acids, carbohydrates, and peptides. Furthermore, it is possible to extend the use of PyAOP, a reagent usually used for peptide coupling, to a range of phosphate substrates including orthophosphate, pyrophosphate, and tetrametaphosphate. This will allow for the synthesis of complex new phosphate architectures to explore as ligands for transition metal complexes.

DESCRIPTION OF THE INVENTION

Our invention effects triphosphorylation of suitable nucleophilic substrates, such as alcohols, amines, and phosphates, in one step. Trimetaphosphate is utilized as the source of phosphate, and PyAOP is utilized as a coupling reagent to achieve the transformation. Trimetaphosphate solubilized in organic solvents as the bis(triphenylphosphine)iminium (PPN) salt, [PPN]$_3$[P$_3$O$_9$]·H$_2$O, 1, is activated towards nucleophilic attack by treatment with PyAOP. The resulting activated species, [PPN][P$_3$O$_9$P(NC$_4$H$_8$)$_3$]·2H$_2$O, 2, can be isolated and purified or used directly in one pot. This activated species reacts with nucleophilic substrates to produce functionalized trimetaphosphate derivatives. These compounds are facilely isolated and purified by crystallization. The PPN cation can be exchanged for simple water soluble cations such as sodium and ammonium by addition of the corresponding triflate salt. Dissolution of the sodium or ammonium salts in water gives rapid hydrolysis to the desired linear triphosphate derivatives.

Activation of Phosphates with PyAOP and Related Reagents
Synthesis of 2

The activated trimetaphosphate derivative, [PPN][P$_3$O$_9$P(NC$_4$H$_8$)$_3$]·2H$_2$O, 2, is formed immediately upon mixing [PPN]$_3$[P$_3$O$_9$]·H$_2$O, 1, and PyAOP in a suitable solvent such as acetonitrile, acetone, dichloromethane, dimethylsulfoxide, or dimethylformamide at room temperature. This compound is moderately stable in solution with a half-life of approximately 12 hours and can be used directly in solution. Alternatively, mixing the reagents in acetone immediately precipitates [PPN][P$_3$O$_9$P(NC$_4$H$_8$)$_3$]·2H$_2$O, 2, as a fine, pure powder. This reaction can be performed on multi-gram scales and the product isolated by filtration. When dry, the powder is air and moisture stable for at least several weeks. Additionally, a variety of related phosphonium based peptide coupling reagents may be used in place of PyAOP, such as PyBrOP, PyClOP, and PyBOP. Instead using any of the closely related peptide coupling reagents AOP, BrOP, ClOP, and BOP would yield a similar species but with diethylamino groups instead of pyrrolidines.

Synthesis of Other Activated Phosphates

Other phosphate substrates may similarly be activated towards nucleophilic attack by addition of PyAOP. Possible phosphate substrates include orthophosphate, pyrophosphate, triphosphate, tetrametaphosphate, hexametaphosphate, and others. The resulting species can be used in solution or isolated and purified prior to use. Stability and isolation conditions will vary with substrates. Additionally, a variety of counterions other than PPN may be utilized, such as tetrabutylammonium and tetraphenylphosphonium.

Synthesis of Trimetaphosphate Alkyl Esters

Treatment of [PPN][P$_3$O$_9$P(NC$_4$H$_8$)$_3$]·2H$_2$O, 2, with primary alcohols leads to the corresponding phosphoesters. Reaction conditions and selectivity are dependent on the choice of tertiary amine base. Addition of pyridine generally leads to faster rates of reaction than addition of triethylamine. However, only crystalline products have been obtained with triethylammonium counterions. Triethylamine can be added after the reaction has reached completion to substitute pyridinium counterions for more crystalline triethylammonium counterions. In the absence of an amine base, the product formed reacts with an additional equivalent of alcohol to form linear triphosphate diesters. Additionally, reactions with diols lead to bridged trimetaphosphate esters. These transformations are amenable to a variety of primary alcohols with varying reaction times and isolation conditions. The corresponding reaction with secondary and tertiary alcohols is slower than the rate of hydrolysis of 2 but in totally anhydrous conditions the product of secondary and tertiary alcohols may be isolated as well.

Synthesis of 3a and 3b

Combining 2, pyridine, and methanol in a suitable solvent such as acetonitrile gives formation of [PPN][HNEt$_3$][P$_3$O$_9$Me], 3a, in less than one hour. Addition of triethylamine followed by diethyl ether induces precipitation of the product as colorless crystals. The crystals are separated and purified by decanting and rinsing with acetone. Analogous conditions are suitable for the synthesis of [PPN][HNEt$_3$][P$_3$O$_9$Et], 3b, and this procedure should be amenable to a variety of larger alcohol substrates as well.

Synthesis of Linear Triphosphate Diesters, 4a and 4b

Combining 2 and methanol in a suitable solvent such as acetonitrile gives formation of [PPN][P$_3$O$_{10}$H$_2$Me$_2$], 4a, in approximately 12 hours. Addition of triethylamine followed by addition of ether leads to the precipitation of the product as crystals. The crystals are separated and purified by decanting and rinsing with acetone. The analogous reaction with ethanol requires a longer reaction time, up to 24 hours. This procedure should be amenable to a variety of larger alcohol substrates with increased reaction times.

Synthesis of Bridged Trimetaphosphate Esters, 5

Combining 2, pyridine, and ethylene glycol in a suitable solvent such as acetonitrile gives formation of [PPN][HNEt$_3$][P$_3$O$_9$C$_2$H$_4$OH] in less than 30 minutes.

Addition of triethylamine followed by diethyl ether leads to precipitation of the product as colorless crystals. The crystals can be separated and purified by decanting and rinsing with acetone. This material may then be redissolved in a suitable solvent such as acetonitrile with more 2 and pyridine to give $[PPN]_2[HNEt_3]_2[(P_3O_9)_2C_2H_4]$, 5, in approximately 24 hours. This material is also purified by addition of triethylamine and diethyl ether to precipitate the product as crystals. These crystals are purified by decanting and rinsing with acetone. This procedure should be amenable to a variety of diol substrates to make bridging phosphates with a variety of organic linkers.

Hydrolysis of Trimetaphosphate Alkyl Esters to Linear Triphosphate Esters

Central to this invention is the hydrolysis of functionalized trimetaphosphates to functionalized linear triphosphates. The PPN cations of the phosphate products here may be exchanged for a variety of cations such as alkali metals, alkali earth metals, and ammonium cations. Addition of an acetonitrile solution of the desired cation as a triflate salt to a solution of a PPN phosphate induces immediate precipitation of the phosphate salt of the desired cation. This material is isolated by filtration. Dissolution of these salts in neutral water gives immediate hydrolysis to the corresponding linear triphosphate alkyl ester. This has been demonstrated for 6 and should be amenable to a variety of alkyl trimetaphosphate esters.

Synthesis of Trimetaphosphate Phosphoramidates

Additionally, $[PPN][P_3O_9P(NC_4H_8)_3]\cdot 2H_2O$, 2, reacts with a variety of other nucleophilic substrates including primary and secondary amines. The acidic proton generated in these reactions is scavenged by excess amine substrate to product an ammonium counterion. Crystalline products are obtained and purified in analogous manner to trimetaphosphate alkyl esters. The resulting phosphoramidates are tolerant to alcohols and organic acids even at 80° C. Exchange of PPN cations for water soluble cations with these phosphoramidates and subsequent dissolution in neutral water induces slow (24 hours) hydrolysis to trimetaphosphate.

Synthesis of 7a

Addition of diethylamine to an acetonitrile solution of 2 leads to immediate formation of $[PPN][H_2NEt_2][P_3O_8NEt_2]$, 7a. Addition of diethyl ether precipitates the product as an oil. Decanting this oil and dissolution in acetone induces precipitation of the product as pure crystals, which can be decanted and further rinsed with acetone.

Synthesis of 7b

Addition of tert-butylamine to an acetonitrile solution of 2 leads to immediate formation of $[PPN][H_3NtBu][P_3O_8NHtBu]$, 7b. Addition of diethyl ether precipitates the product as an oil. Decanting this oil and dissolution in acetone induces precipitation of the product as pure crystals, which can be decanted and further rinsed with acetone.

Synthesis of Extended Polyphosphates $[PPN][P_3O_9P(NC_4H_8)_3]\cdot 2H_2O$, 2, additionally reacts with suitably nucleophilic phosphates to give a new phosphate linkage. So far this methodology has been demonstrated for the synthesis of an extended polyphosphate, $[PPN]_4[P_6O_{17}]$, 8. Additionally, it may be used with a variety of organic and inorganic phosphates to generate larger linear, branched, and cyclic phosphates.

Synthesis of 8

Addition of $[PPN]_3[P_3O_9]\cdot H_2O$, 1, to an acetonitrile solution of $[PPN][P_3O_9P(NC_4H_8)_3]\cdot 2H_2O$, 2, produces $[PPN]_4[P_6O_{17}]$, 8, as well as some hydrolysis products in approximately 12 hours. Addition of diethyl ether to this solution precipitates the mixture of products as an oil. Decanting this oil and rinsing with acetone removes the hydrolysis to products to give 8 as a remaining oil. Drying the product oil under vacuum gives solid material.

Commercial Applications

Utilizing $[PPN][P_3O_9P(NC_4H_8)_3]\cdot 2H_2O$, 2, as a source of triphosphate is a much more direct method to triphosphorylated molecules than traditional synthetic procedures. Additionally, 2 can be quickly and cheaply produced on large scales. Therefore, this species is suitable for immediate commercialization as a reagent to triphosphorylate nucleophilic substrates. Being able to purchase 2 from a chemical supplier would allow much easier access to triphosphorylated molecules for the biochemistry and pharmacological communities, thus supporting and stimulating research in this area. Triphosphorylation could therefore be a significant addition to combinatorial chemistry libraries for drug development.

2 additionally could be used in lieu of existing commercial methods for the production of triphosphorylated molecules. For example, the cost of guanosine triphosphate could be significantly reduced by synthesis from cheap guanosine and 2 rather than laboriously isolated from biological sources or synthesized from guanosine by conventional routes. Trisodium trimetaphosphate is exceedingly cheap (approximately $30 for 500 g from Sigma-Aldrich). Limitations on the cost of this procedure are PyAOP, (PPN)(Cl), and sodium triflate. PyAOP can be in principle replaced with somewhat cheaper PyBrOP or BrOP, and the former have been tested and provided similar results. (PPN)(Cl) and sodium triflate are used to solubilize trimetaphosphate in organic solvents and later resolubilize the products in water, but these materials can easily be recycled. Precipitation with sodium triflate produces PPN triflate as a byproduct, which can in turn be used in place of (PPN)(Cl).

The immediate commercial applications of $[PPN][P_3O_9P(NC_4H_8)_3]\cdot 2H_2O$, 2, are easily realizable, but in addition, the overall methodology of phosphorylation using peptide coupling reagents can be applied to a variety of systems. For example, treatment of a variety of linear and cyclic organic and inorganic phosphates with PyAOP and related reagents leads to similarly activated species. Therefore, an extremely broad class of molecules can be synthesized by this approach. At the simplest end of the spectrum, mono-, di-, tri-, tetra-, or hexa-phosphorylated molecules could be synthesized directly from a nucleophilic substrate and an activated phosphate of the appropriate chain length. Additionally, these activated phosphates are reactive enough to couple to other phosphates. Therefore, organic phosphates can be coupled together such as two ATP molecules coupled together to generate diadenosine hexaphosphate. Therefore, this coupling strategy can be used to generate a wide variety of novel molecules that have never before been studied in biological systems or pharmacological studies.

Therefore, a series of reagents related to 2 may be commercialized with each installing a phosphate chain of a specific length. This would further advance the role of phosphorylation in combinatorial drug discovery. Similarly these reagents could also be utilized in industry to cheaply produce polyphosphorylated chemicals in an analogous manner to 2.

Summary

Alcohol, amine, and phosphate substrates can be triphosphorylated in one step with trimetaphosphate and peptide coupling reagents such as PyAOP. Additionally, the active phosphorylating agent, 2, is facilely synthesized, isolated, and purified. Choice of substrate leads to a wide variety of possible organic and inorganic polyphosphates, and the resulting species are easily isolated and purified by crystallization. This methodology may furthermore be extended to a variety of phosphate substrates to generate extended polyphosphorylated molecules of any desired chain length with ease and low cost.

LIST OF ABBREVIATIONS USED

Figure 41:
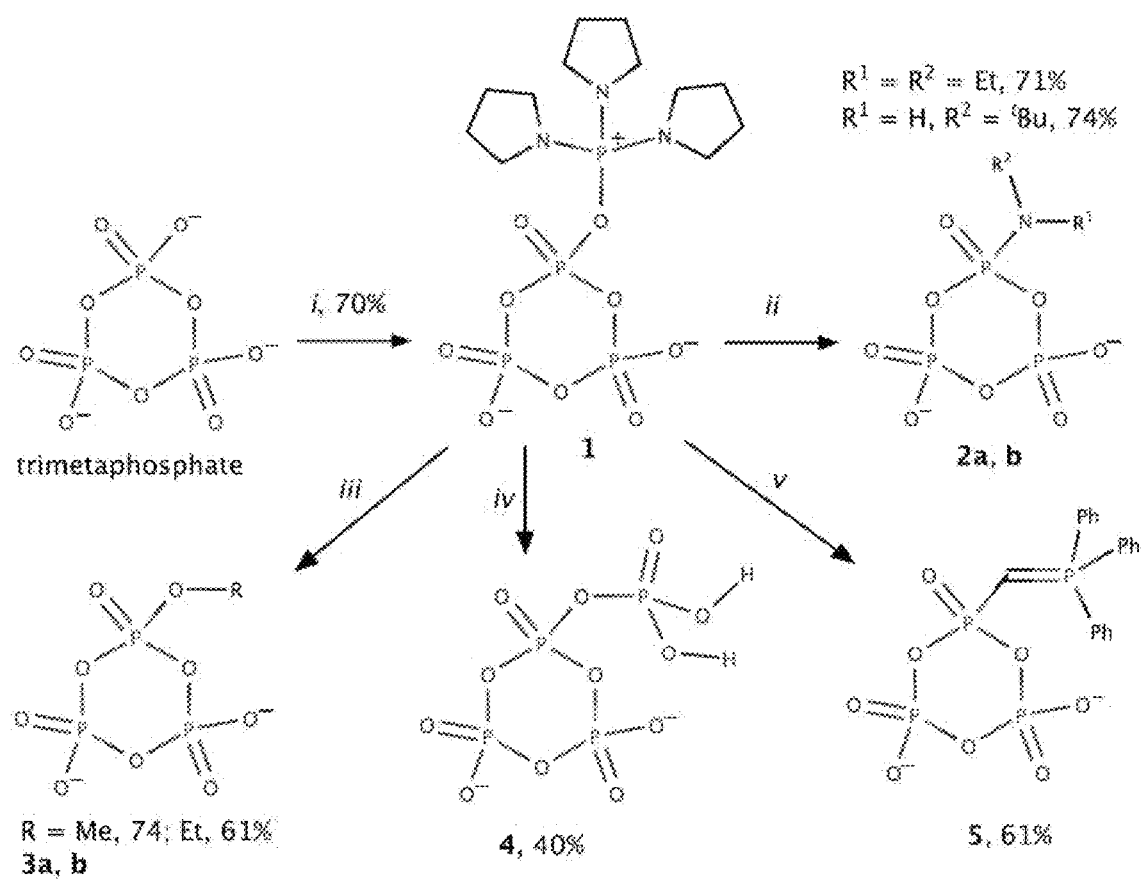
FIG. 41 shows the synthesis of anions 1 through 5 as their PPN salts: i, one equivalent (equiv) of PyAOP in acetone for 30 min at 25° C.; ii, 5 equiv of amine in acetonitrile for 15 min at 25° C.; iii, 5 equiv of alcohol, 2 equiv of pyridine, and 2 equiv of triethylamine in acetonitrile for 2 h at 25° C.; iv, one equiv of [PPN][H$_2$PO$_4$] in acetonitrile for 15 min at 25° C.; v, 4 equiv of H$_2$CPPh$_3$ in acetonitrile for 24 h under an inert atmosphere at 25° C.

PyAOPP=(7-azabenzotriazol-1-yloxy)tripyrrolidinophosphonium hexafluorophosphate
ATP=adenosine Triphosphate
PPN=bis(triphenylphosphine)iminium
PyBrOP=bromotripyrrolidinophosphonium hexafluorophosphate
PyClOP=chlorotripyrrolidinophosphonium hexafluorophosphate
PyBOP=benzotriazol-1-yl-oxytripyrrolidinophosphonium hexafluorophosphate)
AOP=(7-azabenzotriazol-1-yloxy)tris(dimethylamino)phosphoniumhexafluorophosphate
BrOP=bromotris(dimethylamino)phosphonium hexafluorophosphate
ClOP=chlorotris(dimethylamino)phosphonium hexafluorophosphate
BOP=(benzotriazol-1-yloxytris(dimethylamino)phosphonium hexafluorophosphate Referring to FIG. 41, the Wittig reagent $H_2CPPh_3$ as a C-nucleophile reacts with 1 presumably generating the unobserved intermediate anion $[P_3O_8CH_2PPh_3]^-$, which is deprotonated in turn by a second equivalent of the Wittig reagent. This results in anion 5, itself a phosphorus ylide, delivering a powerful synthetic handle for the synthesis of phosphonates (FIG. 41) in the unusual context of a singly functionalized, intact cyclic triphosphate. Due to the synthesis method, novel anion 5 is obtained as a mixed PPN and methyltriphenylphosphonium salt, which has proved difficult to crystallize. This mixed salt of anion 5 is obtained in reasonable purity and is well-characterized by NMR spectroscopy and MS methods.

Figure 42:
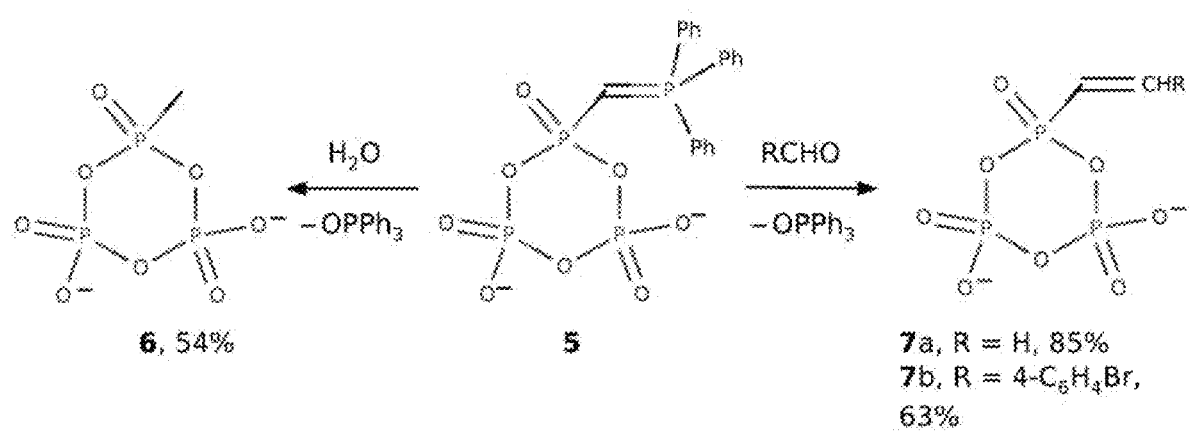
FIG. 42 shows the treatment of 5 with Water or Aldehydes To Generate Phosphonates 6, 7a, and 7b.

Reaction of 5 with water gives methyl phosphonate 6 (FIG. 42). As a phosphorus ylide, 5 undergoes the Wittig reaction with aldehydes to form alkenyl phosphonates 7; the olefins generated from $4\text{-BrC}_6H_4CHO$ are a mixture of E and Z isomers (FIG. 42). Anion 5 is unreactive toward acetone and similar ketones at room temperature, a result that is typical for stabilized phosphorus ylides. Phosphorus ylides stabilized by an adjacent phosphonate group are well known and have been employed previously in the synthesis of simple alkenyl monophosphonates. The closest reported analogue to 5, $Ph_3PCHP(O)(OPh)_2$, has been utilized in the synthesis of 6'-deoxyhomonucleoside-6'-phosphonic acids from 5'-nucleoside aldehydes.

Figure 43:
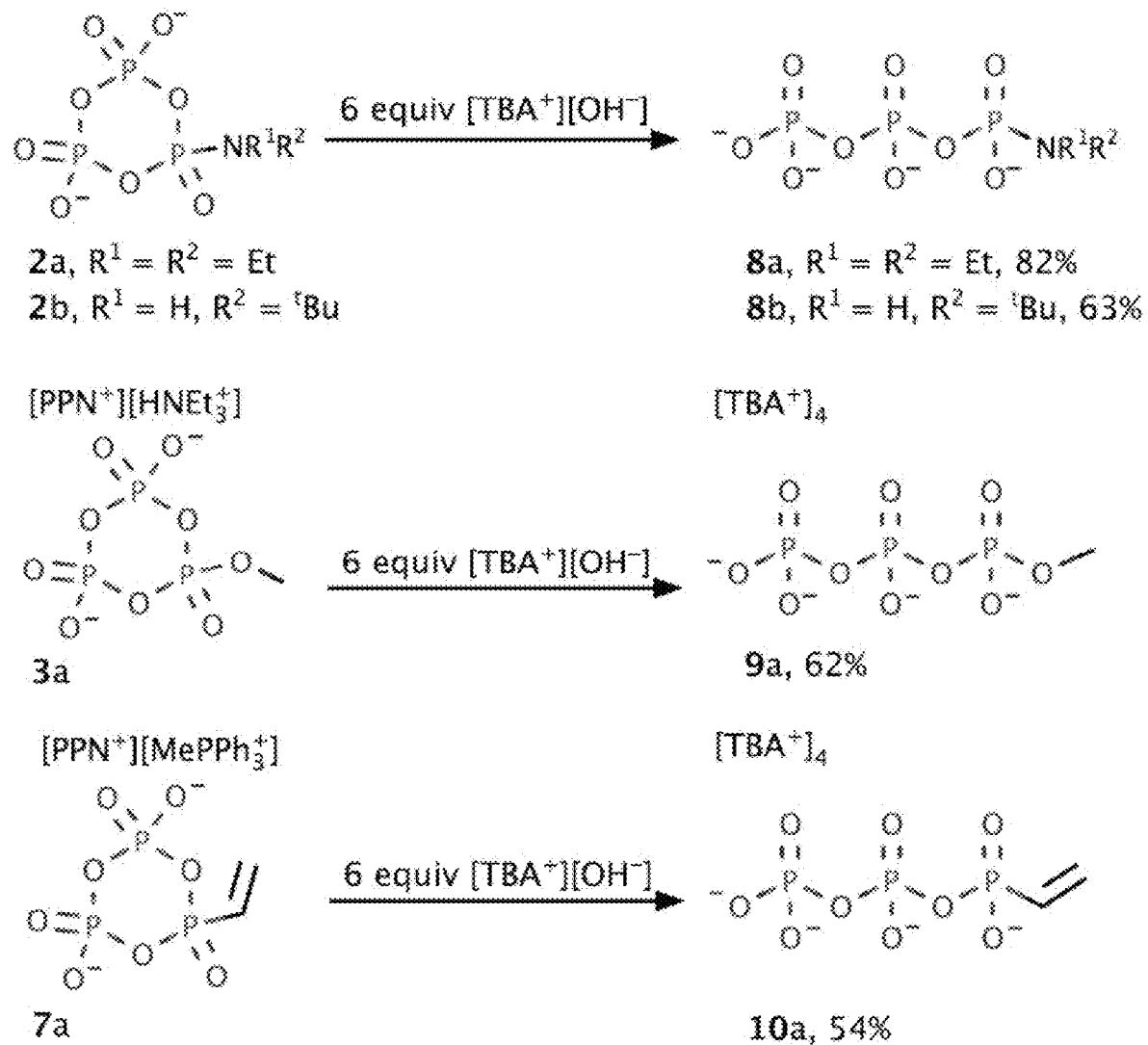
FIG. 43 shows ring Opening of Anions 2a, 2b, 3a, and 7a by treatment with aqueous tetrabutylammonium hydroxide.

Selected examples of the isolated phosphoramidate (2a and 2b), organophosphate (3a), and phosphonate (7a) trimetaphosphate derivatives were converted to linear forms by treatment with aqueous tetrabutylammonium hydroxide in acetonitrile (FIG. 43). Although excess hydroxide reacted with the phosphorus-containing cations to give side products, these were easily separated by extraction with dichloromethane. Accordingly, tetra-anionic linear triphosphate derivatives 8a, 8b, 9a, and 10a were isolated as water-soluble TBA salts in good purity without the need for chromatographic separation.

Experimental Details

General Considerations

All manipulations were performed in a fumehood, open to ambient atmosphere. All solvents were stored over activated 4A sieves but otherwise used as received. 1 was synthesized according to the literature procedure. All other reagents were purchased and used as received. Deuterated solvents were purchased from Cambridge Isotope Labs and used as received. NMR spectra were obtained on a Varian Inova 300 instrument equipped with an Oxford Instruments superconducting magnet or on a Bruker Avance 400 instrument equipped with a Magnet Scientific superconducting magnet. $^1H$ and $^{13}C$ NMR spectra were referenced internally to residual solvent signals. $^{31}P$ NMR spectra were referenced internally to PPN. Electrospray ionization mass spectra (ESI-MS(−)) were acquired on a Micromass Q-TOF ESI spectrometer. Samples were prepared in acetonitrile, and a source temperature of 100° C. and desolvation gas temperature of 150° C. were used. Elemental analyses were performed by Midwest Microlab.

Synthesis of 2

1 (6.13 g, 3.22 mmol) was suspended in 25 mL of acetone. To this stirring suspension was added slowly a solution of PyAOP (1.68 g, 3.22 mmol). Upon addition the mixture immediately becomes bright yellow and briefly homogeneous. After approximately 5 minutes, the product forms as a tan precipitate. The mixture was left to stir for an additional 25 minutes, after which it was filtered and the product collected on a buchner funnel. The solid product was rinsed with acetone until the filtrate ran clear. Drying the resulting solids under vacuum at room temperature for several hours afforded the final product as a tan powder (2.37 g, 2.25 mmol, 69.9% yield). Elem. Anal. Found (Calc'd) for $C_{48}H_{58}N_4O_{11}P_6$: C 54.80 (54.76), H 5.57 (5.55), N 4.99 (5.32). $^1H$ NMR (acetonitrile-$d_3$, 300 MHz) δ 7.69-7.45 (m, 30H), 3.38 (m, 12H), 1.92 (m, 12H). $^{13}C\{^1H\}$ NMR (acetonitrile-$d_3$, 100.6 MHz) δ 135 (s), 133 (m), 130 (m), 47, (d), 27 (d). $^{31}P\{^1H\}$ NMR(acetonitrile, 121.4 MHz) δ 23.0 (s), 18.2 (d, $J_{pp}$=15.0 Hz), −21.4 (d, $J_{pp}$=25.5 Hz), −31.3 (dt, $J_{pp}$=−15.0, 25.5 Hz).

Synthesis of 3a 2 (0.36 g, 0.35 mmol) was dissolved in 3 mL of acetonitrile. To this solution was added triethylamine (0.10 mL, 0.70 mmol) followed by methanol (0.07 mL, 1.76 mmol). The reaction was monitored by $^{31}P$ NMR and all starting material was consumed after approximately five hour. The solution was then filtered through celite to remove any insoluble impurities. To this solution was added 10 mL of diethyl ether resulting in a cloudy white suspension. After sitting for two hours, this mixture formed colorless crystals and some tan oil. The solids were decanted, and the oil rinsed away with acetone. The resulting crystals of the product were dried under vacuum (0.23 g, 0.26 mmol, 74% yield). Elem. Anal. Found (Calc'd) for $C_{43}H_{49}N_2O_9P_5$: C 57.58 (57.85), H 5.55 (5.60), N 3.37 (3.14). $^1H$ NMR (acetonitrile-$d_3$, 400 MHz) δ 10.78 (b, 1H), 7.66-7.44 (m, 30H), 3.72 (d, 3H), 3.06 (q, 6H), 1.21 (t, 9H). $^{13}C\{^1H\}$ NMR (acetonitrile-$d_3$, 100.6 MHz) δ 134 (s), 133 (m), 130 (m), 55 (d), 46 (s), 9 (s). $^{31}P\{^1H\}$ NMR(acetonitrile, 121.4 MHz) δ

23.0 (s), −19.3 (t, $J_{pp}$=23.0 Hz), −21.0 (d, $J_{pp}$=23.0 Hz). ESI-MS(−) of [$P_3O_9$Me]H⁻(CH₃CN, m/z) 252.93 (calc'd 252.91).

Synthesis of 3b with Triethylamine 2 (0.36 g, 0.35 mmol) was dissolved in 3 mL of acetonitrile. To this solution was added triethylamine (0.10 mL, 0.70 mmol) followed by ethanol (0.10 mL, 1.75 mmol). The reaction was monitored by $^{31}$P NMR, and after approximately 16 hours, all of two had been consumed. The solution was then filtered through celite to remove any insoluble impurities. To this solution was added 10 mL of diethyl ether, resulting in a cloudy white suspension. This mixture was allowed to sit for two hours, during which time colorless crystals and a small amount of tan oil formed. The solids were decanted, and the oil was rinsed away with acetone. The crystalline product was then dried under vacuum (0.10 g, 0.11 mmol, 32% yield). Elem. Anal. Found (Calc'd) for $C_{44}H_{51}N_2O_9P$=: C 57.16 (58.28), H 5.61 (5.67), N 3.54 (3.09). $^1$H NMR (acetonitrile-$d_3$, 400 MHz) δ 10.73 (b, 1H), 7.66-7.46 (m, 30H), 4.15 (dq, 2H), 3.09 (q, 6H), 1.94 (t, 3H), 1.23 (t, 9H). $^{13}$C{$^1$H} NMR (acetonitrile-$d_3$, 100.6 MHz) δ 135 (s), 133 (m), 130 (m), 65 (d), 46 (s), 16 (d), 9 (s). $^{31}$P{$^1$H} NMR(acetonitrile, 121.4 MHz) δ 23.0 (s), −20.6 (m, $J_{pp}$=23.0 Hz), −21.2 (m, $J_{pp}$=23.0 Hz). ESI-MS(−) of [$P_3O_9$Et]H (CH₃CN, m/z) 266.91 (calc'd 266.92).

2 (0.24 g, 0.24 mmol) was dissolved in 3 mL of acetone. To this solution was added tbutylamine (0.13 mL, 1.19 mmol) at once. The mixture was allowed to stir for 15 minutes, after which it was filtered through celite to remove any insoluble impurities. Then 10 mL of diethyl ether was added, and the resulting cloudy white suspension was allowed to settle into an oil at the bottom of the reaction vessel over the course of one hour. The oil was decanted and dried under vacuum for 15 minutes to give a foamy solid. This solid was then dissolved in 3 mL of acetone. Diethyl ether was added dropwise to this solution until it became cloudy, approximately 3 mL. The resulting mixture was allowed to stand for several hours, causing the product to precipitate as a white solid. The solid product was decanted, rinsed with acetone, and dried under vacuum (0.16 g, .018 mmol, 74%). $^1$H NMR (acetonitrile-$d_3$, 400 MHz) δ 8.11 (b, 3H), 7.67-7.48 (m, 30H), 3.95 (b, 1H), 1.31 (s, 9H), 1.26 (s, 9H). $^{13}$C{$^1$H} NMR (acetonitrile-$d_3$, 100.6 MHz) δ 135 (s), 133 (m), 130 (m), 66 (s), 51 (d), 32 (d), 28 (s). $^{31}$P{$^1$H} NMR(acetonitrile, 121.4 MHz) δ 23.0 (s), −10.8 (t, Jpp=21:6 Hz), −20.7 (d, Jpp=21:6 Hz).

Synthesis of 3b with Pyridine 2 (0.10 g, 0.10 mmol) was dissolved in 0.5 mL of acetonitrile. To this solution was added pyridine (0.02 mL, 0.20 mmol) followed by ethanol (0.03 mL, 0.49 mmol). The reaction was monitored by $^{31}$P NMR, and all of two was consumed after one hour. The mixture was then filtered through celite to remove any insoluble impurities. To this mixture was added 3 mL of diethyl ether resulting in a cloudy suspension. However, after two hours the product precipitated as an oil rather than crystals. Decanting the oil, redissolving in acetonitrile, and adding triethylamine (0.03 mL, 0.20 mmol) gave the same product as when triethylamine was used instead of pyridine initially. The product was then isolated as previously discussed (0.055 g, 0.061 mmol, 61% yield). The isolated material was spectroscopically identical to that which was previously synthesized.

Synthesis of 4a 2 (0.21 g, 0.16 mmol) was dissolved in 2 mL of acetonitrile. To this solution was added methanol (0.04 mL, 0.80 mmol). After stirring for 12 hours, triethylamine (0.07 mL, 0.48 mmol) was added, and the solution was filtered through celite. To this was added 10 mL of diethyl ether, giving a cloudy suspension. After several hours this suspension settled to an oil which was decanted and dried under vacuum. Dissolution of this oil in acetone gave the product as crystals upon standing for several hours. The crystals were decanted, rinsed with acetone, and dried under vacuum (0.030 g, 0.029 mmol, 18% yield) $^{31}$P{$^1$H} NMR (acetonitrile, 121.4 MHz) δ 23.0 (s), −11.0 (d), −23.9 (t). ESI-MS(−) of [$P_3O_{10}$Me₂]H₂⁻ (CH₃CN, m/z) 285.14 (calc'd 284.93).

Synthesis of 9

2 (0.25 g, 0.24 mmol) was dissolved in 3 mL of acetonitrile. To this solution was added pyridine (0.04 mL, 0.48 mmol) followed by ethylene glycol (0.007 mL, 0.12 mmol). After thirty minutes, triethylamine (0.07 mL, 0.48 mmol) was added and the solution filtered through celite to remove any insoluble impurities. To this solution was added 10 mL of ether to give a cloudy suspension. After sitting for several hours, the suspension settled into an oil. After sitting overnight, the oil turned into tan crystals. The crystals of product were decanted, rinsed with acetone, and dried under vacuum (0.095 g, 0.10 mmol, 43% yield) $^1$H NMR (acetonitrile-$d_3$, 400 MHz) δ 10.65 (b, 1H), 7.66-7.46 (m, 30H), 4.11 (m, 2H), 3.62 (m, 2H) 3.09 (q, 6H), 2.60 (b, 1H), 1.23 (t, 9H). $^{31}$P{$^1$H} NMR (acetonitrile, 121.4 MHz) δ 23.0 (s), −18.7 (t), −21.2 (d). ESI-MS(−) of [$P_3O_9C_2H_4$OH]H⁻ (CH₃CN, m/z) 282.88 (calc'd 282.92).

Synthesis of 5

9 (0.095 g, 0.10 mmol) was suspended in 5 mL of acetonitrile. To this suspension was added pyridine (0.02 mL, 0.21 mmol) followed by 2 (0.16 g, 0.15 mmol). This suspension was stirred for 24 hours whereupon it became homogeneous. Triethylamine (0.03 mL, 0.21 mmol) was then added to the solution, and it was then filtered through celite to remove any insoluble impurities. To this solution was added 10 mL of diethyl ether resulting in a cloudy suspension. After several hours this suspension settled into an oil. The oil was decanted and dried under vacuum. Dissolution of the resulting solids in acetone induced precipitation of the product as crystals. The crystals were decanted, rinsed with acetone, and dried under vacuum. $^1$H NMR (acetonitrile-$d_3$, 400 MHz) δ 10.65 (b, 2H), 7.66-7.46 (m, 60H), 3.96 (d, 4H), 3.09 (q, 12H), 1.23 (t, 18H). $^{31}$P{$^1$H} NMR (acetonitrile, 121.4 MHz) δ 23.0 (s), −18.5 (t), −21.1 (d). ESI-MS(−) of [$(P_3O_9)_2C_2H_4$]H₃⁻ (CH₃CN, m/z) 505.10 (calc'd 504.81).

Synthesis of 6a 3a (0.27 g, 0.30 mmol) was dissolved in 3 mL of acetonitrile. To this mixture was added an acetonitrile solution of sodium triflate (0.16 g, 0.90 mmol). The mixture immediately took on a gel-like consistency. The mixture was filtered to collect the solid product which was dried under vacuum to an off-white crystalline powder. Dissolving this material in 1 mL of water gives nearly quantitative conversion to 6a by $^{31}$P NMR with less than 10% conversion to trimetaphosphate. This solution was filtered to remove insoluble impurities, and the water was evaporated at 60° C under vacuum to give the product as a solid (0.082 g, 0.27 mmol, 91% yield). $^1$H NMR (D₂O, 400 MHz) δ 3.65 (d, 3H). $^{31}$P{$^1$H} NMR (D₂O, 121.4 MHz) δ −8.67 (d), −10.02 (d), −22.40 (t).

Synthesis of 7a 2 (0.36 g, 0.36 mmol) was dissolved in 3 mL of acetonitrile. To this tan solution was added diethylamine (0.18 mL, 1.78 mmol) at once. This solution was allowed to stir for 15 minutes, after which it was filtered through celite to remove any insoluble impurities. Then 10 mL of diethyl ether was added, resulting in a cloudy white suspension. This mixture was allowed to settle for one hour, whereupon a tan oil formed in the bottom of the reaction vessel. The oil was decanted and dried under vacuum for 15 minutes to give a foamy solid. This material was then dissolved in 2 mL of acetone and left to sit. After 30 minutes, the product precipitated as colorless crystals. The crystals were decanted, rinsed with acetone, and dried under vacuum (0.24 g, 0.26 mmol, 71% yield). Elem. Anal. Found (Calc'd) for $C_{44}H_{52}N_3O_9P_5$: C 56.99 (57.33), H 6.12 (5.69), N 4.22 (4.56). $^1H$ NMR (acetonitrile-$d_3$, 400 MHz) δ 9.24 (b, 2H), 7.69-7.45 (m, 30H), 3.11 (dq, 4H), 2.90 (q, 4H), 1.24 (t, 6H), 1.05 (t, 6H). $^{31}C\{^1H\}$ NMR (acetonitrile-$d_3$, 100.6 MHz) δ 135 (s), 133 (m), 130 (m), 42 (s), 40 (d), 14 (d), 12 (s). $^{31}P\{^1H\}$ NMR(acetonitrile, 121.4 MHz) δ 23.0 (s), −9.32 (t, $J_{pp}$=24.5 Hz), −20.5 (d, $J_{pp}$=24.5 Hz). ESI-MS(−) of $[P_3O_8NEt_2]H^-$ ($CH_3CN$, m/z) 293.98 (calc'd 293.97).

Synthesis of 7b 2 (0.24 g, 0.24 mmol) was dissolved in 3 mL of acetone. To this solution was added t-butylamine (0.13 mL, 1.19 mmol) at once. The mixture was allowed to stir for 15 minutes, after which it was filtered through celite to remove any insoluble impurities. Then 10 mL of di-ethyl ether was added, and the resulting cloudy white suspension was allowed to settle into an oil at the bottom of the reaction vessel over the course of one hour. The oil was decanted and dried under vacuum for 15 minutes to give a foamy solid. This solid was then dissolved in 3 mL of acetone. Diethyl ether was added dropwise to this solution until it became cloudy, approximately 3 mL. The resulting mixture was allowed to stand for several hours, causing the product to precipitate as a white solid. The solid product was decanted, rinsed with acetone, and dried under vacuum (0.16 g, 0.018 mmol, 74% yield). Elem. Anal. Found (Calc'd) for $C_{44}H_{52}N_3O_9P_5$: C 58.95 (57.33), 5.76 (5.69), 4.18 (4.56). $^1H$ NMR (acetonitrile-$d_3$, 400 MHz) δ 8.11 (b, 3H), 7.67-7.48 (m, 30H), 3.95 (b, 1H), 1.31 (s, 9H), 1.26 (s, 9H). $^{13}C\{^1H\}$ NMR (acetonitrile-$d_3$, 100.6 MHz) δ 135 (s), 133 (m), 130 (m), 66 (s), 51 (d), 32 (d), 28 (s). $^{31}P\{^1H\}$ NMR(acetonitrile, 121.4 MHz) δ 23.0 (s), −10.8 (t, Jpp=21.6 Hz), −20.7 (d, Jpp=21.6 Hz). ESI-MS(−) of $[P_3O_8NHtBu]H^-$ ($CH_3CN$, m/z) 293.96 (calc'd 293.97).

Synthesis of 8

2 (0.14 g, 0.14 mmol) and 1 (0.26 g, 0.14 mmol) were combined in 3 mL MeCN. After stirring for approximately 12 hours, all 2 was consumed by $^{31}P$ NMR. The solution was then filtered through celite to remove any insoluble impurities. To this solution was added 10 mL of diethyl ether, giving a cloudy suspension. After several hours, the suspension settled into an oil. Decanting the oil and drying under vacuum gave a solid material. Addition of acetone caused the oil to reform. Washing the oil with several aliquots of acetone removes the hydrolysis byproducts. Decanting the oil and drying under vacuum gives the product as a solid (0.15 g, 0.056 mmol, 40% yield). $^{31}P\{^1H\}$ NMR(acetonitrile, 121.4 MHz) δ 23.0 (s), −21.6 (d), −31.4 (t). ESI-MS(−) of $[P_6O_{17}]H_3^-$ ($CH_3CN$, m/z) 461.05 (calc'd 460.78).

X-Ray Diffraction Studies

General Considerations

Crystals were mounted in hydrocarbon oil on a nylon fiber. Low-temperature (100 K) data were collected on a Bruker-AXS X8 Kappa Duo diffractometer coupled to a Smart Apex2 CCD detector (3a and 4a) or a Photon2 CPAD detector (2) with κα radiation (λ=0.71073 Å) with ω-and φ-scans. A semi-empirical absorption correction was applied to the diffraction data using SADABS. See, Sheldrick, G. M. SADABS.

1996, which is incorporated by reference in its entirety. All structures were solved by intrinsic phasing using SHELXT and refined against $F^2$ on all data by full-matrix least squares with SHELXL-2015 using established methods. See, Sheldrick, G. M. *Acta Crystallographica Section C Structural Chemistry* 2015, 71, 3-8, and Sheldrick, G. M.; Schneider, T. R. [16] *SHELXL: High-resolution refinement;* 1997; pp 319-343, each of which is incorporated by reference in its entirety. All non-hydrogen atoms were refined anisotropically. All hydrogen atoms were included in the model at geometrically calculated positions and refined using a riding model unless otherwise noted. The isotropic displacement parameters of all hydrogen atoms were fixed to 1.2 times the Ueq value of the atoms they are linked to (1.5 times for methyl groups). Descriptions of the individual refinements follow below and details of the data quality and a summary of the residual values of the refinements for all structures are given. Further details can be found in the form of .cif files available from the CCDC.

X-Ray Diffraction Study of 2

Colorless diffraction quality crystals of 2 were grown from the procedure listed above. This molecule crystallized in the triclinic space group P1 with two molecules, two PPN cations, and four water molecules per unit cell. One pyrrolidine ring was refined as disordered over two positions differing by a rotation of approximately 180° about the P—N axis. The ratio of the disordered rings refined to 0.629:0.371. The hydrogen atoms of the water molecules were located in the difference electron density map.

The following descriptions relate to FIGS. 41-43.

Synthesis of [PPN][MePPh$_3$][5]

In the glovebox, [PPN] [1] 2H$_2$O (1.33 g, 1.26 mmol) was dissolved in acetonitrile (3 mL). This solution was then added at once to a bright yellow suspension of methylidene triphenylphosphorane (1.40 g, 5.05 mmol) in acetonitrile (6 mL). Upon addition, the mixture becomes homogeneous and the yellow color darkens. This mixture was then stirred for 24 hours during which the color darkens to a deep orange/red. This solution was then filtered through Celite to remove any insoluble material, and the solution was concentrated under vacuum to a volume of 3 mL. To this solution was added diethyl ether (15 mL), resulting in precipitation of an orange oil from a yellow solution. The solution was decanted off, and the oil was dried under vacuum for 15 minutes to give a foamy solid. Diethyl ether (5 mL) and a stir bar were added and the mixture vigorously stirred to give a suspension. The solution was decanted off and the solids rinsed again with 5 mL of diethyl ether. Drying the remaining solids under vacuum for two hours gives the product as a pale orange powder (1.01 g, 0.77 mmol, 61%) Elem. Anal. Found(Calc'd) for $C_{74}H_{564}NO_8P_7$: C 62.97 (67.74), H 4.96 (4.92), N 1.23 (1.07). $^1H$ NMR (acetonitrile-$d_3$, 300 MHz) δ 7.81-7.47 (m, 45H), 3.00 (d, 3H), 1.39 (dd, 1H). $^{13}C\{^1H\}$ NMR (acetonitrile-$d_3$, 100.6 MHz) δ 136 (d), 135 (s), 134 (d), 134 (d), 133 (m), 132 (d), 131 (d), 130 (m), 129 (d), 127 (dd), 121 (d). $^{31}P\{^1H\}$ NMR(acetonitrile, 121.4 MHz) 6 24.2 (s), 23.0 (s), 22.7 (d, $J_{PP}$=48:5 Hz), 14.7 (dt, $J_{PP}$=48:5;

27:0 Hz), −19.1 (d, $J_{PP}$=27:0 Hz). ESI-MS(−) of [P$_3$O$_8$CHPPh$_3$]H$^-$(CH$_3$CN, m/z) 496.95 (calc'd 496.99)

Synthesis of [PPN][MePPh$_3$][6]

In the glovebox, orange [PPN][MePPh$_3$][5] (0.074 g, 0.056 mmol) was dissolved in acetonitrile (2 mL). This solution was then removed from the glovebox. In the fumehood, exposed to air, water (0.01 mL, 0.3 mmol) was added to this solution. After 2 hours, the yellow/orange color of the solution faded to colorless. To this solution was added diethyl ether (10 mL), resulting in a cloudy suspension. After several hours, this suspension settled into an oil. Decanting the supernatant off the oil and drying the oil under vacuum for several hours gave a foamy solid. To this was added acetone (5 mL) and a stir bar. Vigorous stirring for 30 minutes resulted in a fine white powder. Decanting the solvent and drying the powder under vacuum gives the solid product as an extremely hygroscopic powder (0.032 g, 0.031 mmol, 54%) 1H NMR (acetonitrile-d$_3$, 300 MHz) δ 7.84-7.48(m, 45H), 2.96 (d, 3H), 1.57 (d, 3H). $^{13}$C{$^1$H} NMR (acetonitrile-d$_3$, 100.6 MHz) δ 136 (d), 135 (s), 134 (d), 133 (m), 131 (d), 130 (m), 128 (dd), 12 (d), 9 (d). $^{31}$P {$^1$H} NMR(acetonitrile, 121.4 MHz) δ 24.0 (s), 23.0 (s), 12.1 (t, $J_{pp}$=48:5 Hz), −20.3 (d, $J_{PP}$=48:5 Hz). ESI-MS(−) of [P$_3$O$_8$Me]H$^-$ (CH$_3$CN, m/z) 236.91 (calc'd 236.91)

Synthesis of [PPN][MePPh$_3$][7a]

In the glovebox, orange [PPN][MePPh$_3$][5] (0.17 g, 0.13 mmol) was dissolved in acetonitrile (2 mL). This solution was added to solid paraformaldehyde (0.01 g, 0.38 mmol) suspended in acetonitrile (2 mL). This mixture was then stirred for 30 minutes, during which time the pale orange color faded to near colorless. The mixture was then filtered through Celite to remove any insoluble material, and diethyl ether (10 mL) was added, resulting in a cloudy suspension. After several hours, this suspension settled into an oil. This oil was decanted and dried under vacuum to give a foamy solid. A stir bar and diethyl ether (2 mL) were added to this solid and the mixture stirred vigorously to give a fine powder. The supernatant was decanted off and the powder dried under vacuum to give the product (0.11 g, 0.12 mmol, 85%). Elem. Anal. Found(Calc'd) for C$_{57}$H$_{51}$NO$_8$P$_6$: C 63.09 (64.33), H 5.21 (4.83), N 1.34 (1.32). $^1$H NMR (acetonitrile-d$_3$, 300 MHz) δ 7.84-7.48 (m, 45H), 6.34 (m, 1H), 6.18 (m, 1H), 5.90 (m, 1H), 2.95 (m, 3H). $^{13}$C{$^1$H} NMR (acetonitrile-d$_3$, 100.6 MHz) δ 136 (d), 135 (s), 134 (d), 133 (m), 131 (d), 130 (m), 128 (dd), 121 (d). $^{31}$P{$^1$H} NMR(acetonitrile, 121.4 MHz) δ 24.0 (s), 23.0 (s), −1.3 (t, $J_{PP}$=25:9 Hz). −20.1 (d, $J_{PP}$=25:9 Hz). ESI-MS(−) of [P$_3$O$_8$C$_2$H$_3$]H$^-$ (CH$_3$CN, m/z) 248.91 (calc'd 248.91).

Synthesis of [PPN][MePPh$_3$][7b]

In the glovebox, orange [PPN][MePPh$_3$][5] (0.14 g, 0.10 mmol) was dissolved in acetonitrile (2 mL). To this solution was added a solution of 4-bromobenzaldehyde (0.021 g, 0.12 mmol) in acetonitrile (2 mL). This mixture was then stirred for 24 hours, during which time the pale orange color faded to near colorless. The mixture was then filtered through Celite to remove any insoluble material, and diethyl ether (10 mL) was added resulting in a cloudy suspension. After several hours, this suspension settled into an oil. This oil was decanted and dried under vacuum to give a foamy solid. A stir bar and diethyl ether (2 mL) were added to this solid and the mixture stirred vigorously to give a fine powder. The supernatant was decanted off and the powder dried under vacuum to give the product (0.079 g, 0.065 mmol, 62%). Proton and phosphorus NMR spectroscopy showed the product to be a 1:2.4 mixture of the E and Z isomers respectively. Elem. Anal. Found(Calc'd) for C$_{63}$H$_{54}$BrNO$_8$P$_6$: C 61.98 (62.06), H 5.06 (4.47), N 0.95 (0.56). $^1$H NMR (acetonitrile-d$_3$, 300 MHz) δ 7.96-7.50 (m, 45H), 7.55 (dd, 1H, Z), 7.20 (dd, 1H, E), 6.81 (t, 1H, Z), 6.43 (t, 1H, E), 3.18 (d, 3H) $^{13}$C{$^1$H} NMR (acetonitrile-d$_3$, 100.6 MHz) δ 145 (d), 136 (d), 135 (s), 134 (d), 133 (m), 133 (s), 132 (s), 131 (d), 130 (m), 128 (dd), 121 (d). $^{31}$P{$^1$H} NMR(acetonitrile, 121.4 MHz) δ 24.0 (s), 23.0 (s), −0.2 (t, Z, $J_{PP}$=25:6 Hz), −3.7 (t, E, $J_{PP}$=26:2 Hz), −19.9 (d, Z, $J_{PP}$=25:6 Hz), −20.4 (d, E, $J_{PP}$=26:2 Hz). ESI-MS(−) of [P$_3$O$_8$C$_2$H$_2$PhBr]H$^-$ (CH$_3$CN, m/z) 402.83 (calc'd 402.85).

Synthesis of [TBA]$_4$[8a]

[PPN][H$_2$NEt$_2$][2a] (0.047 g, 0.050 mmol) was dissolved in acetonitrile (3 mL) in a scintillation vial in the fumehood. To this solution was added a solution of 40 wt % aqueous tetrabutylammonium hydroxide (0.12 g, 0.30 mmol) in acetonitrile (3 mL). The mixture was then stirred for 36 hours. Volatiles were then evaporated under vacuum for 30 minutes to give an oil. To this was added deionized water (3 mL) resulting in a cloudy suspension. This mixture was then extracted three times with dichloromethane (3×3 mL). The resulting aqueous phase was filtered through Celite R and volatiles removed under vacuum at 60_C for four hours, giving the product as a colorless oil (0.063 g, 82%). $^1$H NMR (D$_2$O, 400 MHz) δ 3.19 (m, 32H), 3.02 (m, 4H), 1.65 (tt, 32H), 1.37 (qt, 32H), 1.08 (t, 6H), 0.94 (t, 48H). $^{13}$C{$^1$H} NMR (D$_2$O, 100.6 MHz) δ 58.1 (t), 50.5 (d), 23.1 (s), 19.1 (s), 13.9 (d), 12.8 (s). $^{31}$P{$^1$H} NMR (D$_2$O, 162.0 MHz) δ −0.5 (d, $J_{PP}$=23:8 Hz), −6.5 (d, $J_{PP}$=20:7 Hz), −22.7 (dd, $J_{PP}$=23:8; 20:7 Hz). ESI-MS(−) of [P$_3$O$_9$NC$_4$H$_{10}$][TBA]$_2$H$^-$ (CH$_3$CN, m/z) 794.86 (calc'd 794.53).

Synthesis of [TBA]$_4$[8b]

[PPN][H$_3$NtBu][2b] (0.080 g, 0.087 mmol) was dissolved in acetonitrile (3 mL) in a scintillation vial in the fumehood. To this solution was added a solution of 40 wt % aqueous tetrabutylammonium hydroxide (0.34 g, 0.52 mmol) in acetonitrile (3 mL). The mixture was then stirred for 12 hours. Volatiles were then evaporated under vacuum to give an oil. To this was added deionized water (3 mL) resulting in a cloudy suspension. This mixture was then extracted three times with dichloromethane (3 3 mL). The resulting aqueous phase was filtered through Celite R and volatiles removed under vacuum at 60° C. for four hours giving the product as a colorless oil (0.070 g, 63%). $^1$H NMR (D$_2$O, 400 MHz) δ 3.19 (m, 32H), 1.64 (tt, 32H), 1.36 (tq, 32H), 1.26 (s, 9H), 0.94 (t, 48H). $^{13}$C{$^1$H} NMR (D$_2$O, 100.6 MHz) δ 58.1 (t), 49.6 (d), 30.7 (d), 23.1 (s), 19.1 (s), 12.8 (s). $^{31}$P{$^1$H} NMR (D$_2$O, 162.0 MHz) δ −3.40 (d, $J_{PP}$=21:1 Hz), −6.4 (d, $J_{PP}$=21:0 Hz), −22.8 (dd, $J_{PP}$=21:1; 21:0 Hz). ESI-MS(−) of [P$_3$O$_9$NC$_4$H$_{10}$][TBA]$_2$H$^-$ (CH$_3$CN, m/z) 794.83 (calc'd 794.53).

Synthesis of [TBA]$_4$[9a]

[PPN][HNEt$_3$][3a] (0.050 g, 0.056 mmol) was dissolved in acetonitrile (3 mL) in a scintillation vial in the fumehood. To this solution was added a solution of 40 wt % aqueous tetrabutylammonium hydroxide (0.22 g, 0.34 mmol) in acetonitrile (3 mL). The mixture was then stirred for 30 minutes. Volatiles were then evaporated under vacuum to give an oil. To this was added deionized water (3 mL) resulting in a cloudy suspension. This mixture was then extracted three times with dichloromethane (3×3 mL). The resulting aqueous phase was filtered through Celite R and volatiles removed under vacuum at 60° C. for four hours giving the product as a colorless oil (0.043 g, 62%). $^1$H NMR (D$_2$O, 400 MHz) δ 3.68 (d, 3H), 3.20 (m, 32H), 1.65 (tt, 32H), 1.35 (tq, 32H), 0.95 (t, 48H) $^{13}$C{$^1$H} NMR (D$_2$O, 100.6 MHz) δ 58.1 (t), 53.4 (d), 23.1 (s), 19.1 (s), 12.8 (s). $^{31}$P {$^1$H} NMR (D$_2$O, 121.4 MHz) δ −6.3 (d, $J_{PP}$=21:3 Hz), −9.6 (d, $J_{PP}$=19:9 Hz), −22.7 (dd, $J_{PP}$=23:1; 19:9 Hz). ESI-MS(−) of [P3O10CH3][TBA]2H—(CH3CN, m/z) 753.78 (calc'd 753.47).

Synthesis of [TBA]$_4$[10a]

[PPN][MePPh$_3$][7a] (0.043 g, 0.040 mmol) was dissolved in acetonitrile (3 mL) in the fumehood. To this solution was added a solution of 40 wt % aqueous tetrabutylammonium hydroxide (0.16 g, 0.24 mmol) in acetonitrile (3 mL). The mixture was then stirred for 30 minutes. Volatiles were then evaporated under vacuum to give an oil. To this was added deionized water (3 mL) resulting in a cloudy suspension. This mixture was then extracted three times with dichloromethane (3×3 mL). The resulting aqueous phase was filtered through Celite and volatiles removed under vacuum at 60° C. giving the product as a colorless oil (0.027 g, 54%). $^1$H NMR (D$_2$O, 400 MHz) δ 6.38-5.84 (m, 3H), 3.20 (m, 32H), 1.65 (tt, 32H), 1.37 (qt, 32H), 0.95 (t, 48H). $^{13}$C{$^1$H} NMR (D$_2$O, 100.6 MHz) δ 131.9 (d), 129.0 (d), 58.1 (t), 23.1 (s), 19.1 (s), 12.8 (s)$^{31}$P{$^1$H} NMR (D$_2$O, 162.0 MHz) δ −5.1 (d, $J_{PP}$=22:2 Hz), −6.3 (d, $J_{PP}$=21:5 Hz), −22.7 (dd, $J_{PP}$=22:2; 21:5 Hz). ESI-MS(−) of [P$_3$O$_9$C$_2$H$_3$][TBA]$_2$H$^-$ (CH$_3$CN, m/z) 749.71 (calc'd 749.48).

TABLE 1

Crystallographic Table for 2

| | | |
|---|---|---|
| Identification code | 2 | |
| Empirical formula | C48 H58 N4 O11 P6 | |
| Formula weight | 1052.80 | |
| Temperature | 100(2) K | |
| Wavelength | 0.71073 Å | |
| Crystal system | Triclinic | |
| Space group | P1 | |
| Unit cell dimensions | a = 10.7896(12) Å | a = 94.628(5)°. |
| | b = 14.973(2) Å | b = 97.727(6)°. |
| | c = 15.5499(18) Å | g = 92.077(5)°. |
| Volume | 2478.3(5) Å$_3$ | |
| Z | 2 | |
| Density (calculated) | 1.411 Mg/m$_3$ | |
| Absorption coefficient | 0.281 mm-$_1$ | |
| F(000) | 1104 | |
| Crystal size | 0.108 × 0.069 × 0.053 mm$_3$ | |
| Theta range for data collection | 2.398 to 28.362°. | |
| Index ranges | −14 <= h <= 14, −20 <= k <= 19, −20 <= l <= 20 | |
| Reflections collected | 169841 | |
| Independent reflections | 12323 [R(int) = 0.0679] | |
| Completeness to theta = 25.242Å° | 99.9% | |
| Absorption correction | Semi-empirical from equivalents | |
| Refinement method | Full-matrix least-squares on F$_2$ | |
| Data/restraints/parameters | 12323/747/675 | |
| Goodness-of-fit on F2 | 1.042 | |
| Final R indices [I > 2sigma(I)] | R1 = 0.0394, wR2 = 0.0930 | |
| R indices (all data) | R1 = 0.0550, wR2 = 0.1019 | |
| Extinction coefficient | n/a | |
| Largest diff. peak and hole | 0.510 and −0.587 e Å$_{−3}$ | |

X-Ray Diffraction Study of 3a

Colorless diffraction quality crystals of 3a were grown by layering an acetonitrile solution of 3a with diethyl ether. Leaving the solution to sit overnight formed diffraction quality crystals. This molecule crystallized in the monoclinic space group P2$_1$/n with four molecules, four diethylammonium counterions, and four PPN counterions in the unit cell. No disorder was modeled and the ammonium NH hydrogens was located in the difference electron density map.

TABLE 2

Crystallographic Table for 3a

| | |
|---|---|
| Identification code | 3a |
| Empirical formula | C44 H52 N3 O8 P5 |
| Formula weight | 905.74 |
| Temperature | 100(2) K |
| Wavelength | 0.71073 Å |
| Crystal system | Monoclinic |

TABLE 2-continued

| Crystallographic Table for 3a | | |
|---|---|---|
| Space group | P2$_1$/n | |
| Unit cell dimensions | a = 8.8510(6) Å | α = 90°. |
| | b = 33.631(2) Å | β = 93.551(2)°. |
| | c = 14.7539(7) Å | γ = 90°. |
| Volume | 4383.3(4) Å$^3$ | |
| Z | 4 | |
| Density (calculated) | 1.369 Mg/m$^3$ | |
| Absorption coefficient | 0.265 mm$^{-1}$ | |
| F(000) | 1896 | |
| Crystal size | 0.250 × 0.150 × 0.147 mm$^3$ | |
| Theta range for data collection | 1.211 to 30.589°. | |
| Index ranges | −12 <= h <= 12, −48 <= k <= 48, −21 <= l <= 21 | |
| Reflections collected | 170934 | |
| Independent reflections | 13451 [R(int) = 0.0351] | |
| Completeness to theta = 25.242Å | 100.0% | |
| Absorption correction | Semi-empirical from equivalents | |
| Refinement method | Full-matrix least-squares on F$_2$ | |
| Data/restraints/parameters | 13451/2/551 | |
| Goodness-of-fit on F2 | 1.061 | |
| Final R indices [I > 2sigma(I)] | R1 = 0.0346, wR2 = 0.0853 | |
| R indices (all data) | R1 = 0.0394, wR2 = 0.0886 | |
| Extinction coefficient | n/a | |
| Largest diff. peak and hole | 0.465 and −0.416 e Å$^{-3}$ | |

X-Ray Diffraction Study of 4a

Colorless diffraction quality crystals of 4a were grown by layering an acetonitrile solution of 3a with diethyl ether. Leaving the solution to sit overnight formed diffraction quality crystals. The molecule crystallized in the orthorhombic space group Pna2$_1$ with four molecules, four PPN counterions, and four triethylammonium counterions in the unit cell. The ammonium NH hydrogen was located in the difference electron density map. The structure was refined as a racemic twin with the BASF parameter refining to a final value of 0.430. The methyl position was found to be highly disordered, and the final model refines the three modeled positions to a ratio of 0.254:0.487:0.259. No additional positions could be found to improve the refinement, however even this model is not entirely satisfactory, and bond metrics for this position are unreliable.

TABLE 3

| Crystallographic Table of 4a | | |
|---|---|---|
| Identification code | 4a | |
| Empirical formula | C45 H49 N2 O9 P5 | |
| Formula weight | 916.71 | |
| Temperature | 100(2) K | |
| Wavelength | 0.71073 Å | |
| Crystal system | Orthorhombic | |
| Space group | Pna2$_1$ | |
| Unit cell dimensions | a = 32.577(2) Å | α = 90°. |
| | b = 9.1970(6) Å | β = 90°. |
| | c = 14.4155(9) Å | γ = 90°. |
| Volume | 4319.0(5) Å$^3$ | |
| Z | 4 | |
| Density (calculated) | 1.410 Mg/m$^3$ | |
| Absorption coefficient | 0.271 mm$^{-1}$ | |
| F(000) | 1920 | |
| Crystal size | 0.314 × 0.217 × 0.135 mm$^3$ | |
| Theta range for data collection | 1.250 to 26.493°. | |
| Index ranges | −40 <= h <= 40, −11 <= k <= 11, −18 <= l <= 18 | |
| Reflections collected | 118595 | |
| Independent reflections | 8913 [R(int) = 0.0700] | |
| Completeness to theta = 25.242Å | 100.0% | |
| Absorption correction | Semi-empirical from equivalents | |
| Refinement method | Full-matrix least-squares on F$_2$ | |
| Data/restraints/parameters | 8913/650/581 | |
| Goodness-of-fit on F$_2$ | 1.037 | |
| Final R indices [I > 2sigma(I)] | R1 = 0.0334, wR2 = 0.0775 | |
| R indices (all data) | R1 = 0.0373, wR2 = 0.0794 | |
| Absolute structure parameter | 0.43(7) | |
| Extinction coefficient | n/a | |
| Largest diff. peak and hole | 0.325 and −0.347 e Å$^{-3}$ | |

The following lists possible cations for use with the compounds described herein.

Nitrogen-Based Cations

| | | |
|---|---|---|
| 1 | 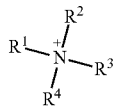 | $R^1$ to $R^4$ are independently hydrogen; or straight or branched, saturated or unsaturated, alkyl containing 1 to 60 carbon atoms and optionally containing a linkage of the formula —O—, —S—, —NH—, —C(O)—, —C(O)O—, —OC(O)—, —C(O)NH— or —NHC(O)—, and optionally substituted with —CN, —Cl, —Br, —F, aryl, aryloxy, heterocyclic, or cyclo-$C_3$-$C_8$-alkyl; or $R^1$ to $R^4$ are independently selected from the group consisting of bicyclic, tricyclic and polycyclic alkyl, cyclo-$C_3$-$C_8$-alkyl, aryl, and heterocyclic, any of which is optionally substituted with —CN, —Cl, —Br, —F, or with phenyl, benzyl, or straight or branched, saturated or unsaturated, alkyl or alkoxy containing up to 12 carbon atoms, the optional phenyl, benzyl, alkyl and alkoxy substituents being optionally substituted with —CN, —Cl, —Br, —F, or $C_1$-$C_6$ alkyl |
| 2 | 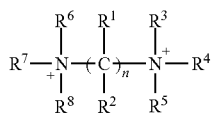 | $R^1$ to $R^8$ are the same as the R claimed in entry 1. <br> n > 0 |
| 3 | 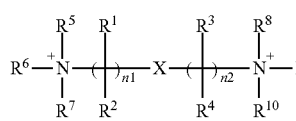 | $R^1$ to $R^{10}$ are the same as the R claimed in entry 1. <br> n1, n2 > 0 <br> X = O, S, NR ( R = H, alkyl, aryl) |
| 4 | 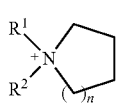 | $R^1$ to $R^2$ are the same as the R claimed in entry 1. <br> n > 0 |
| 5 | 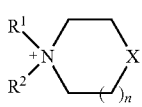 | $R^1$ to $R^2$ are the same as the R claimed in entry 1. <br> n > 0 <br> X = O, S |
| 6 | 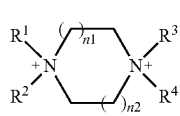 | $R^1$ to $R^4$ are the same as the R claimed in entry 1. <br> n1, n2 > 0 |
| 7 | 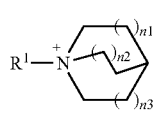 | $R^1$ is the same as the R claimed in entry 1. <br> n1, n2, n3 > 0 |
| 8 | 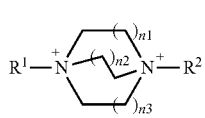 | $R^1$ to $R^2$ are the same as the R claimed in entry 1. <br> n1, n2, n3 > 0 |
| 9 | 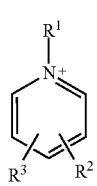 | $R^1$ to $R^3$ are the same as the R claimed in entry 1. |
| 10 | 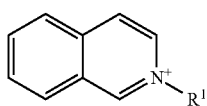 | $R^1$ is the same as the R claimed in entry 1. |

-continued

| | Structure | Description |
|---|---|---|
| 11 | [structure with R¹, R², R³ on N⁺, R⁴, R⁵, R⁶ on N⁺, linked through (CH₂)n1–X–(CH₂)n2 to aromatic ring bearing R⁷] | R¹ to R⁷ are the same as the R claimed in entry 1.<br>X = C, N<br>n1, n2 ≥ 0 |
| 12 | [naphthalene with N⁺R¹R²R³ and N⁺R⁴R⁵R⁶ substituents, and R⁷, R⁸ on rings] | R¹ to R⁸ are the same as the R claimed in entry 1. |
| 13 | [guanidinium: (R¹R²)N⁺=C(N(R³)R⁴)(N(R⁵)R⁶)] | R¹ to R⁶ are the same as the R claimed in entry 1. |
| 14 | [2H-pyrrolium ring with R², R³, R⁴, R⁵ and N⁺–R¹] | R¹ to R⁵ are the same as the R claimed in entry 1. |
| 15 | [imidazolium ring with R³, R⁴, R⁵ and N⁺R¹, N–R²] | R¹ to R⁵ are the same as the R claimed in entry 1. |
| 16 | [bicyclic pyrimidinium fused with (CH₂)n ring, substituents R¹, R², R³] | R¹ to R³ are the same as the R claimed in entry 1.<br>n > 0 |
| 17 | [HOOC–C(R¹)(R²)–N⁺(R³)(R⁴)(R⁵)] | R¹ to R⁵ are the same as the R claimed in entry 1. |

Phosphorus-Based Cations

| | Structure | Description |
|---|---|---|
| 18 | [P⁺(R¹)(R²)(R³)(R⁴)] | R¹ to R⁴ are the same as the R claimed in entry 1. |
| 19 | [R⁷R⁸(R⁶)P⁺–(C(R¹)(R²))n–P⁺(R³)(R⁴)(R⁵)] | R¹ to R⁸ are the same as the R claimed in entry 1.<br>n > 0 |

| | | |
|---|---|---|
| 20 | 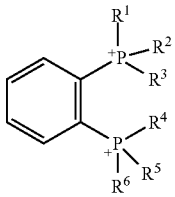 | $R^1$ to $R^6$ are the same as the R claimed in entry 1. |
| 21 | 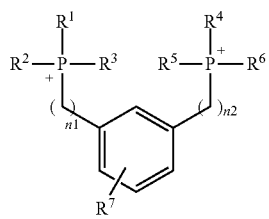 | $R^1$ to $R^7$ are the same as the R claimed in entry 1. n1, n2 > 0 |
| 22 | 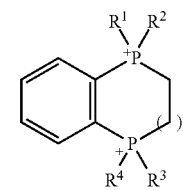 | $R^1$ to $R^4$ are the same as the R claimed in entry 1. n > 0 |
| 23 | 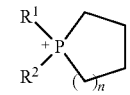 | $R^1$ to $R^2$ are the same as the R claimed in entry 1. n > 0 |

Alkali and Alkali-Earth Metal Cations
Na(15-crown-5)
Na(benzo-15-crown-5)
K(18-crown-6)
K(benzo-18-crown-6)
K(dibenzo-18-crown-6)
K(dicyclohexyl-18-crown-6)
K(kryptofix 222)
K(diaza-18-crown-6)
Li(12-crown-4)
Ca(kryptofix 221)
Ionic Liquid Cations
1,1-dimethyl-pyrrolidinium
1,1-dimethyl-pyrrolidinium
1-butyl-1-ethyl-pyrrolidinium
1-butyl-1-methyl-pyrrolidinium
1-ethyl-1-methyl-pyrrolidinium
1-hexyl-1-methyl-pyrrolidinium
1,3-methyl-imidazolium
1-ethyl-2-3-methyl-imidazolium
1-propyl-2-3-methyl-imidazolium
1-pentyl-3-methyl-imidazolium
1-decyl-3-methyl-imidazolium
1-dodecyl-3-methyl-imidazolium
1-benzyl-3-methyl-imidazolium
1-ethyl-3-methyl-imidazolium
1-hexyl-2-3-methyl-imidazolium
1-hexadecyl-2-3-methyl-imidazolium
1-hexadecyl-3-methyl-imidazolium
1-hexyl-3-methyl-imidazolium
1-methyl-3-(3-phenyl-propyl)-imidazolium
1-octyl-3-methyl-imidazolium
1-octadecyl-3-methyl-imidazolium
1-tetradecyl-3-methyl-imidazolium
3-methyl-imidazolium
1-ethyl-pyridinium
1-butyl-pyridinium
1-hexyl-pyridinium
4-methyl-n-butylpyridinium
1-hexyl-4-methyl-pyridinium
1-octyl-1-methyl-pyrrolidinium
1-octyl-pyridinium
4-methyl-1-octyl-pyridinium
trihexyl-tetradecyl-phosphonium
triisobutyl-methyl-phosphonium
tetrabutyl-phosphonium
benzyl-triphenyl-phosphonium
guanidinium
N,N,N,N-tetramethyl-N-ethylguanidinium
N,N,N,N-pentamethyl-N-propyl-guanidinium
N-butyl-isoquinolinium
O-ethyl-N,N,N,N-tetramethylisouronium
O-methyl-N,N,N,N-tetramethylisouronium
S-ethyl-N,N,N,N-tetramethylisothiouronium Other embodiments are within the scope of the following claims.

What is claimed is:

1. A method of polyphosphorylating a compound comprising contacting the compound with an activated triphosphate including a phosphonium moiety, wherein the compound includes a nucleophilic group and is polyphosphoryled in a single step; and the phosphonium moiety consists of tripyrrolidinophosphonium.

2. The method of claim 1, wherein the activated triphosphate is a cyclic phosphate.

3. The method of claim 1, wherein an intermediate of the activated triphosphate is a trimetaphosphate 7-azabenzotriazole phosphoester or a trimetaphosphate benzotriazol-1-yloxy phosphoester.

4. The method of claim 1, wherein the compound is a protic nucleophile (HNuc), wherein the HNuc includes an alcohol, an amine, or a thio compound.

5. The method of claim 1, wherein the compound is a biochemical substrate, including a nucleoside, an amino acid, a sugar, or a fatty acid.

6. The method of claim 1, wherein the compound is a carbonyl-containing compound.

\* \* \* \* \*